(12) United States Patent
Fenteany et al.

(10) Patent No.: US 6,458,825 B1
(45) Date of Patent: Oct. 1, 2002

(54) LACTACYSTIN ANALOGS

(75) Inventors: Gabriel Fenteany; Timothy F. Jamison, both of Cambridge; Stuart L. Schreiber, Boston; Robert F. Standaert, Arlington, all of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/639,242

(22) Filed: Aug. 15, 2000

Related U.S. Application Data

(63) Continuation of application No. 08/421,583, filed on Apr. 12, 1995, now Pat. No. 6,335,358.

(51) Int. Cl.$^7$ .................. A61K 31/40; A61K 31/38; A61K 31/34
(52) U.S. Cl. .................. 514/421; 514/444; 514/470
(58) Field of Search .................. 514/421, 444, 514/470

(56) References Cited

U.S. PATENT DOCUMENTS

| | | | |
|---|---|---|---|
| 4,962,204 A | 10/1990 | Wambach | 548/408 |
| 5,266,588 A | 11/1993 | Toda et al. | 514/423 |
| 5,340,736 A | 8/1994 | Goldberg | 435/226 |
| 5,453,502 A | 9/1995 | Aikins et al. | 540/203 |

FOREIGN PATENT DOCUMENTS

JP 60/135469 7/1985

OTHER PUBLICATIONS

Belen'kii, W., "Methods of Desulfurization and Their Use in Organic Synthesis", *Chemistry of Organosulfur Compounds*, pp. 193–228 (1990).

Evans, D.A., et al., "Enantioselective Aldol Condensations, 2. Erythro–Selective Chiral Aldol Condensations via Boron Enolates", *J. Am. Chem. Soc.*, vol. 103, pp. 2127–2129 (1981).

Schrock, R.R., "Multiple Metal–Carbon Bonds. 5. The Reaction of Niobium and Tantalum Neopentylidene Complexes with the Carbonyl Function", *J. Am. Chem. Soc.*, pp. 5399–5400 (1976).

Steliou and Mrani, "Tin–Assisted Sulfuration: A Highly Potent New Method For the Conversion of Carbonyl Units into Their Corresponding Thiocarbonyl Analogues" *J. Am. Chem. Soc.*, vol. 104, pp. 3104–3106 (1982).

Jurczak J et al., "Highly stereoselective synthesis of cis (2R, 3S)–3–Hydroxyproline" Tetrahedron Letters 1993 34(44): 7107–7110.

Fenteany G. et al., "A beta–lactone related to lactacystin induces neurite outgrowth in a neuroblastoma cell line and inhibits cell cycle progression in an osteosarcoma cell line" Proc Natl Acad Sci U S A. 1994 91(8): 3358–62.

Kametani T et al., "Studies on the synthesis of carbapenem antibiotics. Stereoselective synthesis of a potential intermediate for 6–amidocarbapenem antibiotics" Heterocycles 20(12): 2355–2358.

Herdeis C and Hubmann HP, "Chiral pool synthesis of trans–(2S,3S)–3–Hydroxyproline and castanodiol from S–Pyroglutamic acid", Tetrahedron: Assymmetry 1994 5(1):119–128.

Sundram H et al., "Chemoenzymatic Synthesis of (2R, 3S)–3–Hydroxyproline from cyclopentadiene" 1994 35(38): 6975–6976.

Kumatori A et al., "Abnormally high expression of proteasomes in human leukemic cells" Proc Natl Acad Sci U S A. 1990 87(18): 7071–5.

Traenckner EB et al., "A proteasome inhibitor prevents activation of NF–kappa B and stabilizes a newly phosphorylated form of I kappa B–alpha that is still bound to NF–kappa B" EMBO J. 1994 13(22): 5433–41.

Ciechanover A, "The ubiquitin–proteasome proteolytic pathway" Cell 1994 79(1):13–21 Review.

Beg AA et al., "Tumor necrosis factor and interleukin–1 lead to phosphorylation and loss of I kappa B alpha: a mechanism for NF–kappa B activation" Mol Cell Biol. 1993 13(6):3301–10.

Miyamoto S et al., "Tumor necrosis factor alpha–induced phosphorylation of I kappa B alpha is a signal for its degradation but not dissociation from NF–kappa B" Proc Natl Acad Sci U S A. 1994 91(26): 12740–4.

Lin YC et al., "Activation of NF–kappa B requires proteolysis of the inhibitor I kappa B–alpha: signal–induced phosphorylation of I kappa B–alpha alone does not release active NF–kappa B" Proc Natl Acad Sci U S A. 1995 92(2): 552–6.

DiDonato JA et al.,"Phosphorylation of I kappa B alpha precedes but is not sufficient for its dissociation from NF–kappa B" Mol Cell Biol. 1995 15(3): 1302–11.

Alkalay I et al., "In vivo stimulation of I kappa B phosphorylation is not sufficient to activate NF–kappa B" Mol Cell Biol. 1995 15(3): 1294–301.

Thanos D and Maniatis T "NF–kappa B: a lesson in family values" Cell. 1995 80(4): 529–32.

Kojima S and Omori M "Two–way cleavage of beta–amyloid protein precursor by multicatalytic proteinase" FEBS Lett. 1992 304(1): 57–60.

Corey EJ et al., "Studies on the total synthesis of lactacystin, and improved aldol coupling reaction and a β–Lactone intermediate in thiol ester formation" 1993 34(44): 6977–6980.

Kogoori et al., (CA 119:117095), 1993.
Katsura et al., (CA 117:131063), 1992.
Thaning et al., (CA 117:7757), 1992.

(List continued on next page.)

*Primary Examiner*—Russell Travers
(74) *Attorney, Agent, or Firm*—Hale and Dorr LLP

(57) ABSTRACT

Compounds related to lactacystin and lactacystin lactone, pharmaceutical compositions containing the compounds, and methods of use.

15 Claims, No Drawings

OTHER PUBLICATIONS

Yu et al., (CA 115:189747), 1991.
Nozoe et al., (CA 112:36460), 1990.
Purvis et al., (CA 111:53899), 1989.
Novales–Li et al., (CA 108:72570), 1988.
Hoerrman, (CA 105:120768), 1986.
Brown et al., (CA 99:105027), 1983.
Haeusler, (CA 95:151123), 1981.
Griffith et al., (CA 87:163362), 1977.
Philip et al., (CA 87:102614), 1977.
Shewry et al., (CA 86:86180), 1977.
Griffith et al., (CA 85:30000), 1976.
Van der Werf et al., (CA 83:174482), 1975.
Deroanne et al., (CA 82:13209), 1975.
Feil et al., (CA 80:71067), 1974.
Gallina et al., (CA 76:139654), 1972.
Kamitani et al., (CA 72:90874), 1970.
Gallina et al., (CA 71:113238), 1969.
Iwasaki et al., (CA 71:61270), 1969.
Ito et al., (CA 68:40037), 1968.
Khomutov et al., (CA 66:76280), 1967.
El Achqar et al., (CA 110:193343), 1989.
Lee et al., (CA 105:24600), 1986.
Lubec et al., (CA 120:124626, 1994.
Kawaguchi et al., (CA 104:10651), 1986.

LACTACYSTIN ANALOGS

CROSS-REFERENCE TO RELATED APPLICATIONS

This application is a continuation of U.S. patent application Ser. No. 08/421,583, filed on Apr. 12, 1995 now U.S. Pat. No. 6,335,358.

STATEMENT AS TO FEDERALLY SPONSORED RESEARCH

This invention was made with support from the National Institute of General Medical Sciences (Grant No. GM38627). Accordingly, the U.S. government may have certain rights in the invention.

BACKGROUND OF THE INVENTION

The invention relates generally to lactacystin and analogues thereof.

Eukaryotic cells contain multiple proteolytic systems, including lysosomal proteases, calpains, ATP-ubiquitin-proteasome dependent pathway, and an ATP-independent nonlysosomal process. The major neutral proteolytic activity in the cytosol and nucleus is the proteasome, a 20S (700 kDa) particle with multiple peptidase activities. The 20S complex is the proteolytic core of a 26S (1500 kDa) complex that degrades or processes ubiquitin-conjugated proteins. Ubquitination marks a protein for hydrolysis by the 26S proteasome complex. Many abnormal or short-lived normal polypeptides are degraded by the ubiquitin-proteasome-dependent pathway. Abnormal peptides include oxidant-damaged proteins (e.g., those having oxidized disulfide bonds), products of premature translational termination (e.g., those having exposed hydrophobic groups which are recognized by the proteasome), and stress-induced denatured or damaged proteins (where stress is induced by, e.g., changes in pH or temperature, or exposure to metals). In addition, some proteins, such as casein, do not required ubquitination to be hydrolyzed by the proteasome.

The proteasome has chymotryptic, tryptic, and peptidyl-glutamyl peptide hydrolizing activities, i.e., the proteasome can cleave peptides on the carboxyl side of hydrophobic, basic, and acidic residues, respectively.

SUMMARY OF THE INVENTION

The invention relates to novel compounds structurally related to lactacystin and lactacystin β-lactone. The invention also relates to pharmaceutical compositions including lactacystin and lactacystin analogs.

One aspect of the invention is a pharmaceutical composition containing a compound having the formula

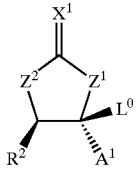

wherein $Z^1$ is O, S, $SO_2$, NH, or $NR_a$, $R_a$ being $C_{1-6}$ alkyl; $X^1$ is O, S, $CH_2$, two singly bonded H, $CH(R_b)$ in the E or Z configuration, or $C(R_b)(R_c)$ in the E or Z configuration, each of $R_b$ and R , independently, being $C_{1-6}$ alkyl, $C_{6-12}$ aryl, $C_{3-8}$ cycloalkyl, $C_{3-8}$ heteroaryl, $C_{3-8}$ heterocyclic radical, or halogen, $X^1$ being two singly bonded H when $Z^1$ is $SO_2$; $Z^2$ is O, S, NH, $NR_d$, or $CHR^1$ in the (R) or (S) configuration, wherein $R_d$ is $C_{1-6}$ alkyl and $R^1$ is H, halogen, $C_{1-6}$ alkyl, $C_{1-6}$ haloalkyl, $C_{2-6}$ alkenyl, $C_{2-6}$ alkynyl, $NR_dR_e$, or the side chain of any naturally occurring α-amino acid, or $R^1$ and $R^2$ taken together are a bivalent moiety, provided that when $R^1$ and $R^2$ are taken together, $Z^1$ is NH or $NR_a$ and $Z^2$ is $CHR^1$; $R^e$ being H, $C_{1-6}$ alkyl, $C_{1-6}$ haloalkyl, $C_{2-6}$ alkenyl, or $C_{2-6}$ alkynyl, and the bivalent moiety forming a $C_{3-8}$ cycloalkyl, $C_{3-8}$ heteroaryl, $C_{3-8}$ heterocyclic radical, or $C_{6-12}$ aryl, where the H in $CHR^1$ is deleted when $R_1$ and $R_2$ taken together form a $C_{3-8}$ heteroaryl or $C_{6-12}$ aryl; $R^2$ is $C_{1-6}$ alkyl, $C_{1-6}$ haloalkyl, $C_{2-6}$ alkenyl, azido, $C_{2-6}$ alkynyl, halogen, $OR_f$, $SR_f$, $NR_fR_g$, $—ONR_fR_g$, $—NR_g(OR_f)$, or $—NR_g(SR_f)$ (each of $R_f$ and $R_g$, independently, being H, $C_{1-6}$ alkyl, $C_{1-6}$ haloalkyl, $C_{2-6}$ alkenyl, or $C_{2-6}$ alkynyl), or $R^1$ and $R^2$ taken together are a bivalent moiety, the bivalent moiety forming a $C_{3-8}$ cycloalkyl, $C_{3-8}$ heteroaryl, $C_{3-8}$ heterocyclic radical, or $C_{6-12}$ aryl, where the H in $CHR^1$ is deleted when $R_1$ and $R_2$ taken together form a $C_{3-8}$ heteroaryl or $C_{6-12}$ aryl; $A^1$ is H, the side chain of any naturally occurring α-amino acid, or is of the following formula,

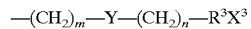

$$—(CH_2)_m—Y—(CH_2)_n—R^3X^3$$

wherein Y is O, S, C=O, C=S, —(CH=CH)—, vinylidene, —C=$NOR_h$, —C=$NNR_iR_{i'}$, sulfonyl, methylene, $CHX^4$ in the (R) or (S) configuration, or deleted, $X^4$ being halogen, methyl, halomethyl, $OR_h$, $SR_h$, $NR_iR_i$, $—NR_i(OR_h)$, or $—NR_i(NR_iR_{i'})$, wherein $R_h$ is selected from H, $C_{1-6}$ alkyl, $C_{1-6}$ haloalkyl, $C_{2-6}$ alkenyl, and $C_{2-6}$ alkynyl, and each of $R_i$ and $R_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and $R^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and $X^3$ is H, hydroxyl, thiol, carboxyl, amino, halogen, ($C_{1-6}$ alkyl)oxycarbonyl, ($C_{7-14}$ arylalkyl)-oxycarbonyl, or $C_{6-14}$ aryl; or $R^3$ and $X^3$ taken together are the side chain of any naturally occurring α-amino acid; $X^2$ is O or S; and $L^o$ is an organic moiety having 1 to 25 carbon atoms, 0 to 10 heteroatoms, and 0 to 6 halogen atoms; and a pharmaceutically acceptable carrier.

A second aspect is a pharmaceutical composition comprising a compound having the following formula

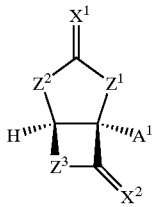

wherein $Z^1$ is O, S, $SO_2$, NH, or $NR_a$, $R_a$ being $C_{1-6}$ alkyl; $X^1$ is O, S, $CH_{21}$ two singly bonded H, $CH(R_b)$ in the E or Z configuration, or $C(R_b)(R_c)$ in the E or Z configuration, each of $R_b$ and $R_c$, independently, being $C_{1-6}$ alkyl, $C_{6-12}$ aryl, $C_{3-8}$ cycloalkyl, $C_{3-8}$ heteroaryl, $C_{3-8}$ heterocyclic radical, or halogen, provided that when $Z^1$ is $SO_2$, $X^1$ is two singly bonded H; $Z^2$ is $CHR^1$ in the (R) or (S) configuration, $R^1$ being H, $C_{1-6}$ alkyl, $C_{1-6}$ haloalkyl, $C_{2-6}$ alkenyl, $C_{2-6}$ alkynyl, hydroxyl, halogen, a side chain of a naturally occuring α-amino acid, $OR_d$, $SR_d$, or $NR_dR_e$ (each of $R_d$ and $R^e$, independently, being H, $C_{1-6}$ alkyl, $C_{1-6}$ haloalkyl, $C_{2-6}$ alkenyl, or $C_{2-5}$ alkynyl); $Z^3$ is O, S, NH, or $NR_j$, wherein $R_j$ is $C_{1-6}$ alkyl; $X^2$ is O or S; and $A^1$ is H, the side chain of any naturally occurring α-amino acid, or is of the following formula,

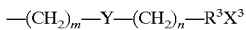

wherein Y is O, S, C=O, C=S, —(CH=CH)—, vinylidene, —C=NOR$_h$, —C=NNR$_i$R$_{i'}$, sulfonyl, methylene, CHX$^4$ in the (R) or (S) configuration, or deleted, X$^4$ being halogen, methyl, halomethyl, OR$_h$, SR$_h$, NR$_i$R$_{i'}$, —NR$_i$(OR$_h$), or —NR$_i$(NR$_i$R$_{i'}$), wherein R$_h$ is selected from H, $C_{1-6}$ alkyl, $C_{1-6}$ haloalkyl, $C_{2-6}$ alkenyl, and $C_{2-6}$ alkynyl, and each of R$_i$ and R$_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and R$^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and X$^3$ is H, hydroxyl, thiol, carboxyl, amino, halogen, ($C_{1-6}$ alkyl)oxycarbonyl, ($C_{7-14}$ arylalkyl)-oxycarbonyl, or $C_{6-14}$ aryl; or R$^3$ and X$^3$ taken together are the side chain of any naturally occurring α-amino acid; and a pharmaceutically acceptable carrier.

A third aspect is a pharmaceutical composition comprising a compound having one of the following formulae

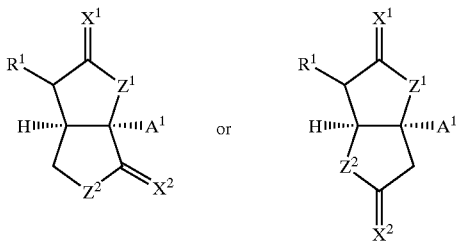

wherein $Z^1$ is NH or NR$_a$, R$_a$ being $C_{1-6}$ alkyl; $X^1$ is O, S, CH$_2$, two singly bonded H, CH(R$_b$) in the E or Z configuration, or C(R$_b$)(R$_c$) in the E or Z configuration, each of R$_b$ and R$_c$, independently, being $C_{1-6}$ alkyl, $C_{6-2}$ aryl, $C_{3-8}$ cycloalkyl, $C_{3-8}$ heteroaryl, $C_{3-8}$ heterocyclic radical, or halogen; $Z^2$ is O, S, NH, or NR$_j$, wherein R$_j$ is $C_{1-6}$ alkyl; R$^1$ is in the (R) or (S) configuration, and is H, $C_{1-6}$ alkyl, $C_{1-6}$ haloalkyl, $C_{2-6}$ alkenyl, $C_{2-6}$ alkynyl, hydroxyl, halogen, a side chain of a naturally occuring α-amino acid, OR$_d$, SR$_d$, or NR$_d$R$_e$ (each of R$_d$ and R$_e$, independently, being H, $C_{1-6}$ alkyl, $C_{1-6}$ haloalkyl, $C_{6-12}$ aryl, $C_{3-8}$ cycloalkyl, $C_{3-8}$ heteroaryl, $C_{3-8}$ heterocyclic radical, or halogen); $X^2$ is O or S; and $A^1$ is H, the side chain of any naturally occurring α-amino acid, or is of the following formula,

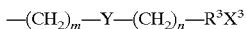

wherein Y is O, S, C=O, C=S, —(CH=CH)—, vinylidene, —C=NOR$_h$, —C=NNR$_i$R$_{i'}$, sulfonyl, methylene, CHX$^4$ in the (R) or (S) configuration, or deleted, X$^4$ being halogen, methyl, halomethyl, OR$_h$, SR$_h$, NR$_i$R$_{i'}$, —NR$_i$(OR$_h$), or —NR$_i$(NR$_i$R$_{i'}$), wherein R$_h$ is selected from H, $C_{1-6}$ alkyl, $C_{1-6}$ haloalkyl, $C_{2-6}$ alkenyl, and $C_{2-6}$ alkynyl, and each of R$_i$ and R$_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and R$^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and X$^3$ is H, hydroxyl, thiol, carboxyl, amino, halogen, ($C_{1-6}$ alkyl)oxycarbonyl, ($C_{7-14}$ arylalkyl)-oxycarbonyl, or $C_{6-14}$ aryl; or R$^3$ and X$^3$ taken together are the side chain of any naturally occurring α-amino acid; and a pharmaceutically acceptable carrier.

A fourth aspect is a pharmaceutical composition containing a compound having the following formula

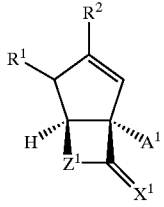

wherein $Z^1$ is O, S, NH or NR$_j$, R$_j$ being $C_{1-6}$ alkyl; $X^1$ is O or S; R$^1$ is in the (R) or (S) configuration, and is H, $C_{1-6}$ alkyl, $C_{1-6}$ haloalkyl, $C_{2-6}$ alkenyl, $C_{2-6}$ alkynyl, hydroxyl, halogen, a side chain of a naturally occuring α-amino acid, OR$_d$, SR$_d$, or NR$_d$R$_e$ (each of R$_d$ and R$_e$, independently, being H, $C_{1-6}$ alkyl, $C_{1-6}$ haloalkyl, $C_{2-6}$ alkenyl, or $C_{2-5}$ alkynyl); R$^2$ is H, $C_{1-6}$ alkyl, $C_{1-6}$ haloalkyl, $C_{2-6}$ alkenyl, $C_{2-6}$ alkynyl, $C_{6-12}$ aryl, $C_{3-8}$ heteroaryl, or halogen; $X^2$ is O or S; and $A^1$ is H, the side chain of any naturally occurring α-amino acid, or is of the following formula,

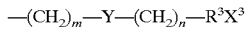

wherein Y is O, S, C=O, C=S, —(CH=CH)—, vinylidene, —C=NOR$_h$, —C=NNR$_i$R$_{i'}$, sulfonyl, methylene, CHX$^4$ in the (R) or (S) configuration, or deleted, X$^4$ being halogen, methyl, halomethyl, OR$_h$, SR$_h$, NR$_i$R$_{i'}$, —NR$_i$(OR$_h$) or —NR$_i$(NR$_i$R$_{i'}$), wherein R$_h$ is selected from H, $C_{1-6}$ alkyl, $C_{1-6}$ haloalkyl, $C_{2-6}$ alkenyl, and $C_{2-6}$ alkynyl, and each of R$_i$ and R$_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and R$^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and X$^3$ is H, hydroxyl, thiol, carboxyl, amino, halogen, ($C_{1-6}$ alkyl)oxycarbonyl, ($C_{7-14}$ arylalkyl)-oxycarbonyl, or $C_{6-14}$ aryl; or R$^3$ and X$^3$ taken together are the side chain of any naturally occurring α-amino acid; and a pharmaceutically acceptable carrier.

A fifth aspect is a pharmaceutical composition comprising a compound having the following formula

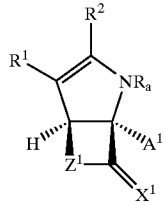

wherein $Z^1$ is O, S, NH or NR$_j$, R$_j$ being $C_{1-6}$ alkyl; $X^1$ is O or S; R$^1$ is H, $C_{1-6}$ alkyl, $C_{1-6}$ haloalkyl, $C_{2-6}$ alkenyl, $C_{2-6}$ alkynyl, hydroxyl, halogen, a side chain of a naturally occuring α-amino acid, OR$_d$, SR$_d$, or NR$_d$R$_e$ (each of R$_d$ and R$_e$, independently, being $C_{1-6}$ alkyl, $C_{1-6}$ haloalkyl, $C_{6-12}$ aryl, $C_{3-8}$ cycloalkyl, $C_{3-8}$ heteroaryl, $C_{3-8}$ heterocyclic radical, or halogen); R$^2$ is H, $C_{1-6}$ alkyl, $C_{1-6}$ haloalkyl, $C_{2-6}$ alkenyl, $C_{2-6}$ alkynyl, $C_{6-12}$ aryl, $C_{3-8}$ heteroaryl, or halogen; $R_a$ is $C_{1-6}$ alkyl; and $A^1$ is H, the side chain of any naturally occurring α-amino acid, or is of the following formula,

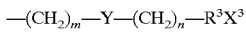

wherein Y is O, S, C=O, C=S, —(CH=CH)—, vinylidene, —C=NOR$_h$, —C=NNR$_i$R$_{i'}$, sulfonyl, methylene, CHX$^4$ in the (R) or (S) configuration, or deleted, X$^4$ being halogen, methyl, halomethyl, OR$_h$, SR$_h$, NR$_i$R$_{i'}$, —NR$_i$(OR$_h$), or —NR$_i$(NR$_i$R$_{i'}$), wherein R$_h$ is selected from H, $C_{1-6}$ alkyl, $C_{1-6}$ haloalkyl, $C_{2-6}$ alkenyl, and $C_{2-6}$ alkynyl, and each of R$_i$ and R$_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and R$^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and X$^3$ is H, hydroxyl, thiol, carboxyl, amino, halogen, ($C_{1-6}$ alkyl)oxycarbonyl, ($C_{7-14}$ arylalkyl)-oxycarbonyl, or $C_{6-14}$ aryl; or R$^3$ and X$^3$ taken together are the side chain of any naturally occurring α-amino acid; and a pharmaceutically acceptable carrier.

A sixth aspect is a pharmaceutical composition containing a compound having the formula

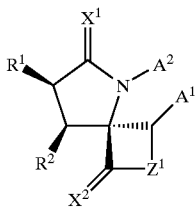

wherein X$^1$ is O, S, CH$_2$, two singly bonded H, CH(R$_b$) in the E or Z configuration, or C(R$_b$) (R$_c$) in the E or Z configuration, each of R$_b$ and R$_c$, independently, being $C_{1-6}$ alkyl, $C_{6-12}$ aryl, $C_{3-8}$ cycloalkyl, $C_{3-8}$ heteroaryl, $C_{3-8}$ heterocyclic radical, or halogen; Z$^1$ is O, S, NH, or NR$_a$, R$_a$ being $C_{1-6}$ alkyl; R$^1$ is H, $C_{1-6}$ alkyl, $C_{1-6}$ haloalkyl, $C_{2-6}$ alkenyl, $C_{2-6}$ alkynyl, hydroxyl, halogen, a side chain of any naturally occuring α-amino acid, OR$_d$, SR$_d$, or NR$_d$R$_e$ (each of R$_d$ and R$_e$, independently, being H, $C_{1-6}$ alkyl, $C_{1-6}$ halo-alkyl, $C_{6-12}$ aryl, $C_{3-8}$ cycloalkyl, $C_{3-8}$ heteroaryl, $C_{3-8}$ heterocyclic radical, or halogen); or R$^1$ and R$^2$ taken together are a bivalent moiety which forms a $C_{3-8}$ cycloalkyl, $C_{3-8}$ heteroaryl, $C_{3-8}$ heterocyclic radical, or $C_{6-12}$ aryl; R$^2$ is H, $C_{1-6}$ alkyl, $C_{1-6}$ haloalkyl, $C_{2-6}$ alkenyl, azido, $C_{2-6}$ alkynyl, halogen, OR$_f$, SR$_f$, NR$_f$R$_g$, —ONR$_f$R$_g$, —NR$_g$(OR$_f$), or NR$_g$(SR$_f$) (each of R$_f$ and R$_g$, independently, being H, $C_{1-6}$ alkyl, $C_{1-6}$ haloalkyl, $C_{2-6}$ alkenyl, or $C_{2-6}$ alkynyl), or R$^1$ and R$^2$ taken together are a bivalent moiety, the bivalent moiety forming a $C_{3-8}$ cycloalkyl, $C_{3-8}$ heteroaryl, $C_{3-8}$ heterocyclic radical, or $C_{6-12}$ aryl;

X$^2$ is O or S; and A$^1$ is in the (R) or (S) configuration, and each of A$^1$ and A$^2$ is independently H, the side chain of any naturally occurring amino a-acid, or is of the following formula,

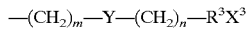

wherein Y is O, S, C=O, C=S, —(CH=CH)—, vinylidene, —C=NOR$_h$, —C=NNR$_i$R$_{i'}$, sulfonyl, methylene, CHX$^4$ in the (R) or (S) configuration, or deleted, X$^4$ being halogen, methyl, halomethyl, OR$_h$, SR$_h$, NR$_i$R$_{i'}$, —NR$_i$(OR$_h$), or —NR$_i$(NR$_i$R$_{i'}$), wherein R$_h$ is selected from H, $C_{1-6}$ alkyl, $C_{1-6}$ haloalkyl, $C_{2-6}$ alkenyl, and $C_{2-6}$ alkynyl, and each of R$_i$ and R$_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and R$^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and X$^3$ is H, hydroxyl, thiol, carboxyl, amino, halogen, ($C_{1-6}$ alkyl)oxycarbonyl, ($C_{7-14}$ arylalkyl)oxycarbonyl, or $C_{6-14}$ aryl; or R$^3$ and X$^3$ taken together are the side chain of any naturally occurring α-amino acid; and a pharmaceutically acceptable carrier.

A seventh aspect is a pharmaceutical composition containing a compound having the following formula

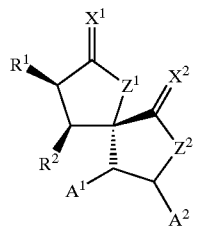

wherein Z$^1$ is NH or NR$_a$, NR$_a$ being $C_{1-6}$ alkyl;

X$^1$ is O, S, CH$_2$, two singly bonded H, CH(R$_b$) in the E or Z configuration, or C(R$_b$) (R$_c$) in the E or Z configuration, each of R$_b$ and R$_c$, independently, being $C_{1-6}$ alkyl, $C_{6-12}$ aryl, $C_{3-8}$ cycloalkyl, $C_{3-8}$ heteroaryl, $C_{3-8}$ heterocyclic radical, or halogen;

Z$^2$ is O, S, NH, or NR$_j$, R$_j$ being $C_{1-6}$ alkyl;

R$^1$ is in the (R) or (S) configuration, and is H, $C_{1-6}$ alkyl, $C_{1-6}$ haloalkyl, $C_{2-6}$ alkenyl, $C_{2-6}$ alkynyl, hydroxyl, halogen, a side chain of any naturally occuring amino acid, OR$_d$, SR$_d$, or NR$_d$R$_e$ (each of R$_d$ and R$_e$, independently, being H, $C_{1-6}$ alkyl, $C_{1-6}$ haloalkyl, $C_{6-12}$ aryl, $C_{3-8}$ cycloalkyl, $C_{3-8}$ heteroaryl, $C_{3-8}$ heterocyclic radical, or halogen); or R$^1$ and R$^2$ taken together are a bivalent moiety which forms a $C_{3-8}$ cycloalkyl, $C_{3-8}$ heteroaryl, $C_{3-8}$ heterocyclic radical, or $C_{6-12}$ aryl; R$^2$ is H, $C_{1-6}$ alkyl, $C_{1-6}$ haloalkyl, $C_{2-6}$ alkenyl, azido, $C_{2-6}$ alkynyl, halogen, OR$_f$, SR$_f$, NR$_f$R$_g$, —ONR$_f$R$_g$, —NR$_g$(OR$_f$), or —NR$_g$(SR$_f$) (each of R$_f$ and R$_g$, independently, being H, $C_{1-6}$ alkyl, $C_{1-6}$ haloalkyl, $C_{2-6}$ alkenyl, or $C_{2-6}$ alkynyl), or R$^1$ and R$^2$ taken together are a bivalent moiety, the bivalent moiety forming a $C_{3-8}$ cycloalkyl, $C_{3-8}$ heteroaryl, $C_{3-8}$ heterocyclic radical, or $C_{6-12}$ aryl; X$^2$ is O or S; and each of A$^1$ and A$^2$ is independently in the (R) or (S) configuration, and is independently H, the side chain of any naturally occurring α-amino acid, or is of the following formula,

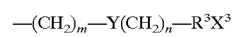

wherein Y is O, S, C=O, C=S, —(CH=CH)—, vinylidene, —C=NOR$_h$, —C=NNR$_i$R$_{i'}$, sulfonyl, methylene, CHX$^4$ in the (R) or (S) configuration, or deleted, X$^4$ being halogen, methyl, halomethyl, OR$_h$, SR$_h$, NR$_i$R$_{i'}$, —NR$_i$(OR$_h$), or —NR$_i$(NR$_i$R$_{i'}$), wherein R$_h$ is selected from H, $C_{1-6}$ alkyl, $C_{1-6}$ haloalkyl, $C_{2-6}$ alkenyl, and $C_{2-6}$ alkynyl, and each of R$_i$ and R$_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and R$^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and $X^3$ is H, hydroxyl, thiol, carboxyl, amino, halogen, ($C_{1-6}$ alkyl)oxycarbonyl, ($C_{7-14}$ arylalkyl)oxycarbonyl, or $C_{6-14}$ aryl; or $R^3$ and $X^3$ taken together are the side chain of any naturally occurring α-amino acid; and a pharmaceutically acceptable carrier.

An eighth aspect is a pharmaceutical composition containing a compound of the formula

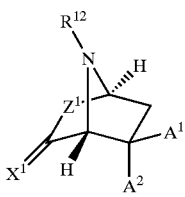

wherein $Z^1$ is O, NH, or $NR_a$, $NR_a$ being $C_{1-6}$ alkyl; $X^1$ is O, S, $CH_2$, or two singly bonded H; each of $A^1$ and $A^2$ is independently H, the side chain of any naturally occurring α-amino acid, or is of the following formula,

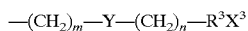

wherein Y is O, S, C=O, C=S, —(CH=CH)—, vinylidene, —C=$NOR_h$, —C=$NNR_iR_{i'}$, sulfonyl, methylene, $CHX^4$ in the (R) or (S) configuration, or deleted, $X^4$ being halogen, methyl, halomethyl, $OR_h$, $SR_h$, $NR_iR_{i'}$, —$NR_i(OR_h)$, or —$NR_i(NR_iR_{i'})$, wherein $R_h$ is selected from H, $C_{1-6}$ alkyl, $C_{1-6}$ haloalkyl, $C_{2-6}$ alkenyl, and $C_{2-6}$ alkynyl, and each of $R_i$ and $R_{i'}$, independently is selected from H, $C_{1-6}$ alkyl, $C_{1-6}$ haloalkyl, $C_{2-6}$ alkenyl, $C_{2-6}$ alkynyl, and $C_{1-6}$ acyl; m is 0, 1, 2, or 3, and n is 0, 1, 2, or 3; and $R^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and $X^3$ is H, hydroxyl, thiol, carboxyl, amino, halogen, ($C_{1-6}$ alkyl)oxycarbonyl, ($C_{7-14}$ arylalkyl)oxycarbonyl, or $C_{6-14}$ aryl; or $R^3$ and $X^3$ taken together are the side chain of any naturally occurring α-amino acid; and $R^{12}$ is H, $C_{1-6}$ alkyl, $C_{1-6}$ haloalkyl, $C_{2-6}$ alkenyl, or $C_{2-6}$ alkynyl; and a pharmaceutically acceptable carrier.

A ninth aspect is a pharmaceutical composition comprising a compound having the formula

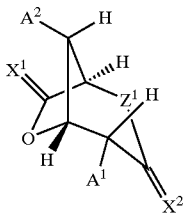

wherein $Z^1$ is NH, or $NR_a$ t $NR_a$ being $C_{1-6}$ alkyl; each of $X^1$ and $X^2$, independently, is O or S; each of $A^1$ and $A^2$ is independently in the (R) or (S) configuration, and is independently H, the side chain of any naturally occurring amino acid, or is of the following formula,

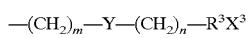

wherein Y is O, S, C=O, C=S, —(CH=CH)—, vinylidene, —C=$NOR_h$, —C=$NNR_iR_{i'}$, sulfonyl, methylene, $CHX^4$ in the (R) or (S) configuration, or deleted, $X^4$ being halogen, methyl, halomethyl, $OR_h$, $SR_h$, $NR_iR_{i'}$, —$NR_i(OR_h)$, or —$NR_i(NR_iR_{i'})$, wherein $R_h$ is selected from H, $C_{1-6}$ alkyl, $C_{1-6}$ haloalkyl, $C_{2-6}$ alkenyl, and $C_{2-6}$ alkynyl, and each of $R_i$ and $R_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and $R^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and $X^3$ is H, hydroxyl, thiol, carboxyl, amino, halogen, ($C_{1-6}$ alkyl)oxycarbonyl, ($C_{7-14}$ arylalkyl)oxycarbonyl, or $C_{6-14}$ aryl; or $R^3$ and $X^3$ taken together are the side chain of any naturally occurring α-amino acid; and a pharmaceutically acceptable carrier.

Many of the compounds described above are novel compounds; the novel compounds are also claimed. The invention also encompasses lactacystin analogues that can be made by the synthetic routes described herein, and methods of treating a subject having a condition mediated by proteins processed by the proteasome by administering an effective amount of a pharmaceutical composition containing a compound disclosed herein to the subject.

The compounds disclosed herein are highly selective for the proteasome, and do not inhibit other proteases such as trypsin, α-chymotrypsin, calpain I, calpain II, papain, and cathepsin B.

Other features or advantages of the present invention will be apparent from the following detailed description, and also from the appending claims.

DETAILED DESCRIPTION OF THE INVENTION

Terms

The term "naturally occurring amino acid" is meant to include the 20 common α-amino acids (Gly, Ala, Val, Leu, Ile, Ser, Thr, Asp, Asn, Lys, Glu, Gln, Arg, His, Phe, Cys, Trp, Tyr, Met and Pro), and other amino acids that are natural products, such as norleucine, ethylglycine, ornithine, methylbutenyl-methylthreonine, and phenylglycine. Examples of amino acid side chains include H (glycine), methyl (alanine), —$CH_2$—(C=O)—$NH_2$ (asparagine), —$CH_2$—SH (cysteine), and —CH(OH)$CH_3$ (threonine).

The term "inhibitor" is meant to describe a compound that blocks or reduces the activity of an enzyme (e.g. the proteasome, or the X/MB1 subunit or α-chain of the 20S proteasome). An inhibitor may act with competitive, uncompetitive, or noncompetitive inhibition. An inhibitor may bind reversibly or irreversibly, and therefore the term includes compounds which are suicide substrates of an enzyme. An inhibitor may modify one or more sites on or near the active site of the enzyme, or it may cause a conformational change elsewhere on the enzyme. Thus, some compounds disclosed herein (e.g., where $L^o$ is an epoxide or aldehyde group) react with the enzyme by bonding to the carbon atom corresponding to C4 of lactacystin (e.g., resulting in a C4 having a hydroxyl or thiol), while other compounds react with the enzyme to release a leaving group (e.g., $L^1$), corresponding to an acylation.

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyano, methylsulfonylamino, alkoxy, acyloxy, nitro, and lower haloalkyl. Similarly, cycloalkyl, aryl, arylalkyl, alkylaryl, heteroaryl, and heterocyclic radical groups may be subsituted with one or more of the above substituting groups. Examples of cycloalkyl groups are cyclopropyl, cyclobutyl, cyclopentyl, cyclohexyl, cycloheptyl, and cyclooctyl. An aryl group is a $C_{6-20}$ aromatic ring, wherein the ring is made of carbon atoms (e.g., $C_{6-14}$, $C_{6-10}$ aryl groups). Examples of haloalkyl include fluoromethyl, dichloromethyl, trifluoromethyl, 1,1-difluoroethyl, and 2,2-dibromoethyl.

A heterocyclic radical contains at least one ring structure which contains carbon atoms and at least one heteroatom (e.g., N, O, S, or P). A heteroaryl is an aromatic heterocyclic radical. Examples of heterocyclic radicals and heteroaryl groups include: thiazolyl, thienyl, furyl, 1-isobenzofuranyl, 2H-chromen-3-yl, 2H-pyrrolyl, N-pyrrolyl, imidazolyl, pyrazolyl, isothiazolyl, isooxazolyl, pyridyl, pyrazinyl, pyrimidinyl, pyradazinyl, indolizinyl, isoindolyl, indolyl, indazolyl, purinyl, phthalazinyl, cinnolinyl, and pteridinyl. A heterocylic radical may be attached to another moiety via a carbon atom or a heteroatom of the heterocyclic radical.

A ($C_n$ alkyl)oxycarbonyl group has the formula R—O—(C═O)—. ($C_{1-6}$ alkyl)oxycarbonyl, therefore, includes methoxycarbonyl and hexyloxycarbonyl. A $Cl_{10}$ acyl group as used herein is of the formula —(C═O)—$L_3$ and contains 1 to 10 carbon atoms and 1–5 heteratoms. Examples of such acyl groups include formyl, acetyl, benzyloxycarbonyl, tert-butoxycarbonyl, trifluoroethyloxy-carbonyl, thiobenzoyl, phenylamidocarbonyl, and 4-nitrophenoxy-carbonyl.

An alkylene is a bivalent radical derived from alkanes by removing two hydrogens from two different carbon atoms. Examples of alkylenes include —$CH_2$—CH(R)—$CH_2$ and 1,4-cyclohexylene. An alkylidene is a bivalent radical derived from alkenes by removing two hydrogens from the same carbon atom, such as 1-propanyl-3-ylidene (═CH—$CH_2$—$CH_2$—).

An aromatic carbon atom, as used herein, is a carbon atom within an aromatic system such as benzene or naphthalene or a heteroaromatic system such as quinoline. Examples of nonaromatic carbon atoms include the carbons atoms in R—(C═O)—R, —$CH_2$Cl, —$CH_2$— and R—(C═O)—O—R. A fragment formula weight is the combined atomic weight of the fragment or moiety indicated. For example, the fragment formula weight of methyl is 15 and the fragment formula weight of hydroxyl is 17.

A leaving group departs from a substrate with the pair of electrons of the covalent bond between the leaving group and the substrate; preferred leaving groups stabilize those electrons via the presence of electron withdrawing groups, aromaticity, resonance structures, or a combination thereof. Examples include halide (I and Br are preferred), mesylate, trifluoromethanesulfonate, p-toluenesulfonate, p-nitrobenzensulfonate, benzoate, p-nitrobenzoate, p-nitrobenzyl, and $C_{2-5}$ haloalkylcarbonyloxy such as trifluoroacetate.

Numerous thiol-, amino-, hydroxy- and carboxy-protecting groups are well-known to those in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the invention. Further examples and conditions are found in T. W. Greene, *Protective Groups in organic Chemistry*, (1st ed., 1981 Theodara Lorene and P. G. H. Wuts, 2nd ed., 1991).

The invention also encompasses isotopically-labelled counterparts of compounds disclosed herein. An isotopically-labelled compound of the invention has one or more atoms replaced with an isotope having a detectable particle- or x-ray-emitting (radioactive) nucleus or a magnetogyric nucleus. Examples of such nuclei include $^2H$, $^3H$, $^{13}C$, $^{15}N$, $^{19}F$, $^{29}Si$, $^{31}P$, $^{32}P$ and $^{125}I$. Isotopically-labelled compounds of the invention are particularly useful as probes or research tools for spectrometeric analyses, radioimmunoassays, binding assays based on γ- or β-scintillation, fluorography, autoradiography, and kinetic studies such as inhibition studies or determination of primary and secondary isotope effects.

The following abbreviations are used in the synthetic description:

AIBN, 2,2'-azobis(isobutyronitrile); Bn, benzyl; BOP-Cl, bis(2-oxo-3-oxazolidinyl)phosphinic chloride; $Bu_2BOTf$, dibutylboron triflate; CDI, N,N'-carbonyldiimidazole; Cp, cyclopentadienyl; DBU, 1,8-diazabicyclo[5.4.0]undec-7-ene; DCC dicyclo-hexylcarbodiimide; DDQ, 2,3-dichloro-5,6-dicyano-1,4-benzo-quinone; DEAD, diethylazodicarboxylate; DIBAL-H diisobutyl-aluminum hydride; DMF, dimethylformamide; Gilbert reagent, dimethyl diazomethylphosphonate; LDA, lithium diisopropylamide; LiHMDS, lithium hexamethyldisilazamide; mesylate, methanesulfonic acid ester; Mitsunobu reagents, (DEAD, $PPh_3$, and nucleophile); NMO, N-methylmorpholine-N-oxide; Ph, phenyl; PhFl, 9-phenyl-9-fluorenyl; $Ph_2NTf$, N-phenyltrifluoromethanesulfonimide; Swern oxidation reagents $((COCl)_2, DMSO, Et_3N)$; TBAF, tetrabutylammonium fluoride; TBS, tert-butyldimethylsilyl; TCDI, thiono-N,N'-carbonyldiimidazole; $Tf_2O$, trifluoromethanesulfonic acid anhydride; TMS, trimethylsilyl; triflate, trifluromethane sulfonate ester; and TsCl, p-toluenesulfonyl chloride.

The following reagents are also used:

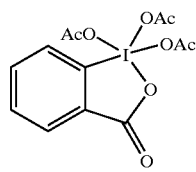

Dess-Martin periodinane

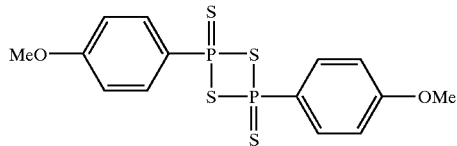

Lawesson's reagent

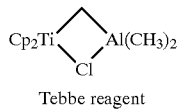

Tebbe reagent

The invention is based, in part, on the structure-function information disclosed herein which suggests the following preferred stereochemical relationships. Note that a preferred compound may have one, two, three, or more stereocenters having the indicated up-down (or β-α where β as drawn herein is above the plane of the page) or (R)-(S) relationship (i.e., it is not required that every stereocenter conform to the structures below).

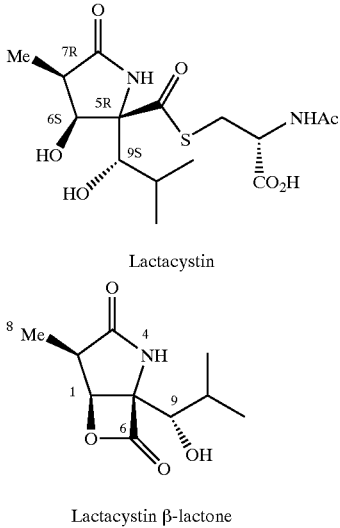

Lactacystin

Lactacystin β-lactone

A person of skill will recognize that the compounds described herein preserve certain stereochemical and electronic characteristics found in either lactacystin or lactacystin β-lactone. For example, the hydroxyisobutyl group and the configuration of the hydroxyl group on C9 are believed to be important for recognition of the target, as are the configurations of the C6 hydroxyl and the C7 methyl of the γ-lactam ring. However, the N-acetylcysteine moiety is not required for activity. Moieties such as $R^2$, $R^1$, and particularly $A^1$ (e.g., where $A^1$ is a side chain of a naturally occurring α-amino acid such as Val, Leu, Lys, and Phe) can be modified to control selectivity for the proteasome, and selectivity for a particular peptidase activity of the proteasome. In combination, these moieties simulate certain peptides or proteins processed or degraded by the proteasome (i.e., are peptidomimetics).

The invention is also based, in part, on the finding that lactacystin and lactacystin β-lactone are highly selective for the X/MB1 subunit and α-chain of the proteasome and do not inhibit the activity of proteases such as trypsin, α-chymotrypsin, calpain I, calpain II, cathepsin, and papain. Such selectivity is useful to formulate a pharmaceutical composition with fewer side effects and to evaluate basic research results involving any subunit of the proteasome in conjunction with the selective inhibition of the X/MB1 subunit and α-chain.

Turning to the novel compounds described by the formulas of compounds contained within the pharmaceutical compositions, several embodiments are next considered.

Embodiments of the first aspect include compounds wherein $L^1$ is linked by an oxygen or sulfur atom to the carbon atom bonded to $X^2$; wherein $A^1$ is $C_{5-20}$ alkyl when $L^0$ is carboxyl or ($C_{1-4}$ alkyl)oxycarbonyl and $A^1$ is alkyl; wherein only one of $A^1$ and $L^0$ is selected from carboxyl and ($C_{1-4}$ alkyl)oxycarbonyl; wherein $A^1$ cannot be H; and wherein $L^1$ has at least 3 carbon atoms when $Z^1$ and $Z^2$ are both NH, and $A^1$ is methoxy; when $R^1$ and $R^2$ are taken together, $Z^2$ is $CR^1$; and when one of $A^1$ and $L^0$ is ($C_{14}$ alkyl)oxycarbonyl or carboxyl, the other of $A^1$ and $L^0$ has a fragment formula weight of at least 20. Novel compounds of the first, fifth, and seventh aspects generally do not have $A^1$ being H.

Further embodiments of the first aspect, when $Z^1$ is NH and $Z^2$ is (R) CHR$^1$, are compounds wherein: $L^1$ has between 0 and 3 nonaromatic acyclic carbon atoms when there are 5 heteroatoms; $L^1$ has between 6 and 15 nonaromatic acyclic carbon atoms when there is only one oxygen atom; and $L^1$ has 0, 1, 3, or 5 nonaromatic carbon atoms when there are three halogen atoms.

Further embodiments of the first aspect include a compound wherein Z2 is CHR$^1$ and $Z^1$ is NH or $NR_a$; wherein $L^0$ is $C_{2-16}$ oxiranyl; $L^1$ is hydroxy, $C_{1-2}$ alkoxy, $C_{1-12}$ alkylsulfonyloxy, $C_{6-20}$ arylsulfonyloxy, $C_{7-20}$ arylalkyl, $C_{6-20}$ aryloxy, $C_{6-20}$ arylalkylcarbonyloxy, $C_{2-8}$ alkylcarbonyloxy, $C_{2-8}$ alkylcarbonylthio, $C_{1-12}$ alkylthio, $C_{6-20}$ arylalkylcarbonylthio, or $C_{6-20}$ arylthio; or $L^2$ is H, $C_{1-2}$ haloalkyl, or $C_{1-6}$ alkyl.

Further embodiments of the first aspect include compounds wherein $Z^1$ is O, S, or $SO_2$; wherein $Z^2$ is O, S, NH, or $NR_d$; wherein $X^1$ is $CH_2$, $CHR_b$, or $C(R_b)(R_c)$; wherein $R^2$ is $C_{1-6}$ alkyl, $C_{1-6}$ haloalkyl, $C_{2-6}$ alkenyl, or halogen; wherein $R^2$ is $OR_f$, $SR_f$, or $NR_fR_g$; wherein $Z^2$ is in the beta (above plane of page) configuration; wherein $CHX^4$ is in the alpha (below plane of paper) configuration; wherein $R^2$ is in the beta configuration; or combinations thereof.

Embodiments of the second aspect include compounds wherein $CHX^4$ is in the (S) configuration when $X^4$ is hydroxyl and —$(CH_2)_n$—$R^3x^3$ is isopropyl; wherein the moiety —$(CH_2)_n$—$R^3X^3$ has between 5 and 20 carbon atoms when $X^4$ is hydroxyl, m is O, and $Z^1$ is NH; wherein $Z^1$ is NH or $NR_a$; wherein $Z^1$ is O, S, or $SO_2$; wherein $Z^1$ is $NR_a$; wherein $X^1$ is $CH_2$, $CH(R_b)$, or $C(R_b)(R_c)$; wherein $Z^2$ is in the beta (above plane of page) configuration; wherein $CHX^4$ is in the alpha (below plane of paper) configuration; wherein $R^1$ is H, $C_{1-6}$ alkyl, $C_{1-6}$ haloalkyl, $C_{2-6}$ alkenyl, $C_{2-6}$ alkynyl, or halogen; wherein $R^1$ is a side chain of a naturally occuring α-amino acid, $OR_d$, $SR_d$, or $NR_dR^e$; or combinations of the above.

Embodiments of the third aspect include compounds wherein: when $X^1$ is 2 singly bonded H and $R^1$ has only one oxygen, then the fragment formula weight of $R^1$ is at least 30 atomic mass units; when $X^1$ is 2 singly bonded H and $R^1$ is 2 H, and $A^1$ is alkyl, then $A^1$ has at least 3 carbon atoms; $A^1$, $R^1$ and $X^1$ taken together have at least one carbon atom, halogen, or heteroatom; when $X^1$ is two singly bonded H, and $R^1$ is H, $X^2$ is O, and $R_h$ is alkyl, then $R_h$ is $C_{4-6}$ alkyl; and when n is 2, $R_h$ is $C_{1-6}$ haloalkyl.

Further embodiments of the third aspect include compounds wherein: $X^1$ is $CH_2$, two singly bonded H, $CH(R_b)$ or $C(R_b)(R_c)$; $Z^2$ is O or S; Z2 is NH or $NR_j$; $R^1$ is $C_{1-6}$ alkyl, $C_{1-6}$ haloalkyl, $C_{2-6}$ alkenyl, $C_{2-6}$ alkynyl, or halogen; $R^1$ is a side chain of a naturally occuring α-amino acid, $OR_d$, $SR_d$, or $NR_dR^e$; $A^1$ cannot be H; $R^1$ is in the beta configuration; $X^4$ is in the alpha configuration; or combinations thereof.

Embodiments of the fourth aspect include compounds wherein: $Z^2$ is O or S; Z2 is NH or $NR_j$; $X^1$ is O or S; $R^1$ is $C_{1-6}$ alkyl, $C_{1-6}$ haloalkyl, $C_{2-6}$ alkenyl, $C_{2-6}$ alkynyl, or halogen; $R^1$ is a side chain of a naturally occuring α-amino acid, $OR_d$, $SR_d$, or $NR_dR_e$; $R^2$ is H, $C_{1-3}$ alkyl, $C_{1-3}$ haloalkyl, $C_{2-3}$ alkenyl, $C_{2-3}$ alkynyl, $C_{6-12}$ aryl, $C_{3-8}$ heteroaryl, or halogen; $R^2$ is H, $C_{3-6}$ alkyl, $C_{3-6}$ haloalkyl, $C_{4-6}$ alkenyl, $C_{4-6}$ alkynyl, $C_{6-12}$ aryl, or $C_{3-8}$ heteroaryl; $A^1$ cannot be H; $R^1$ is in the beta configuration; $X^4$ is in the alpha configuration; or combinations of the above.

Further embodiments of the fifth aspect are compounds wherein: $Z^1$ is O or S; $Z^2$ is NH or $NR_j$; $R^1$ is H, $C_{1-3}$ alkyl, $C_{1-3}$ haloalkyl, $C_{2-3}$ alkenyl, $C_{2-3}$ alkynyl, or a side chain of a naturally occuring α-amino acid, $OR_d$, $SR_d$, or $NR_dR_e$; $R^1$ is H, $C_{4-6}$ alkyl, $C_{4-6}$ haloalkyl, $C_{4-6}$ alkenyl, $C_{4-6}$ alkynyl, halogen, or a side chain of a naturally occuring α-amino acid, $OR_d$, $SR_d$, or $NR_dR_e$; $R^2$ is H, $C_{1-3}$ alkyl, $C_{1-3}$ halo-alkyl, $C_{2-3}$ alkenyl, $C_{2-3}$ alkynyl, $C_{6-12}$ aryl, $C_{3-8}$ heteroaryl, or halogen; $R^2$ is H, $C_{4-6}$ alkyl, $C_{4-6}$ haloalkyl, $C_{4-6}$ alkenyl, $C_{4-6}$ alkynyl, $C_{6-12}$ aryl, or $C_{3-8}$ heteroaryl;n $R_a$ is $C_{1-3}$ alkyl; $A^1$ cannot be H; $X^4$ is in the alpha configuration; or combinations thereof.

Embodiments of the sixth aspect are compounds wherein: $X^1$ is O or S; $X^1$ is $CH_2$, two singly bonded H, $CH(R_b)$, or $C(R_b)(R_c)$; $Z^1$ is O or S; $Z^1$ is NH or $NR_a$; $R^1$ is $C_{1-3}$ alkyl, $C_{1-3}$ haloalkyl, $C_{2-3}$ alkenyl, $C_{2-3}$ alkynyl, halogen, or a side chain of any naturally occuring α-amino acid; $R^1$ is $OR_d$, $SR_d$, or $NR_dR_e$; $R^1$ is $C_{4-6}$ alkyl, $C_{4-6}$ haloalkyl, $C_{4-6}$ alkenyl, $C_{4-6}$ alkynyl, a side chain of any naturally occuring α-amino acid, $OR_d$, $SR_d$, or $NR_dR_e$; $R^1$ and $R^2$ taken together are a bivalent moiety; $R^1$ is in the beta configuration; $R^2$ is in the beta configuration; $R^2$ is $C_{1-3}$ alkyl, $C_{1-3}$ haloalkyl, $C_{6-12}$ aryl, $C_{3-8}$ cycloalkyl, or halogen; $R^2$ is $C_{4-6}$ alkyl, $C_{4-6}$ haloalkyl, $C_{6-12}$ aryl, $C_{3-8}$ cycloalkyl, $C_{3-8}$ heteroaryl, or $C_{3-8}$ heterocyclic radical; $A^1$ has a higher fragment formula weight than $A^2$; $A^1$ has a lower fragment formula weight than $A^2$; $A^1$ is in the (R) configuration; $A^1$ is in the (S) configuration; only one of $A^1$ and $A^2$ is H; $A^1$ is a side chain of any naturally occuring α-amino acid; or combinations thereof.

Embodiments of the seventh aspect are compounds wherein: $X^1$ is O or S; $X^1$ is $CH_2$, two singly bonded H, $CH(R_b)$ or $C(R_b)(RC)$; $Z^1$ is O or S; $z^2$ is NH or $NR_j$; $R^1$ is $C_{1-3}$ alkyl, $C_{1-3}$ haloalkyl, $C_{2-3}$ alkenyl $C_{2-3}$ alkynyl, hydroxyl, halogen, or a side chain of any naturally occuring α-amino acid; $R^1$ is $OR_d$, $SR_d$, or $NR_dR_e$; $R^1$ is $C_{4-6}$ alkyl, $C_{4-6}$ haloalkyl, $C_{4-6}$ alkenyl, $C_{4-6}$ alkynyl, a side chain of any naturally occuring α-amino acid; $R^1$ and $R^2$ taken together are a bivalent moiety; $R^2$ is $C_{1-3}$ alkyl, $C_{1-3}$ haloalkyl, $C_{2-3}$ alkenyl, azido, $C_{2-3}$ alkynyl, hydroxyl, halogen; is $OR_f$, $SR_f$, $NR_fR_g$, $ONR_fR_g$, $NR_g(OR_f)$ or $—NR_g(RS_f)$; $R^2$ is $C_{4-6}$ alkyl, $C_{4-6}$ haloalkyl, $C_{4-6}$ alkenyl, azido, $C_{4-6}$ alkynyl, $OR_f$, $SR_f$, $NR_fR_g$, $ONR_fR_g$, $NR_g(OR_f)$1 or $—NR_g(RS_f)$; $R^1$ and $R^2$ taken together are a bivalent moiety; $R^1$ is in the alpha configuration; $R^1$ is in the beta configuration; $R^2$ is in the alpha configuration; $R^2$ is in the beta configuration; $A^1$ is in the alpha configuration; $A^2$ is in the beta configuration; or combinations thereof.

One embodiment of the eighth aspect is a compound where $A^1$, $A^2$, $R^{12}$, and $X^1$ taken together have at least one carbon atom and one heteroatom. Further embodiments of the eighth aspect are compounds wherein: $Z^1$ is NH, or $NR_a$; $X^1$ is O or S; $X^1$ is $CH_2$, or two singly bonded H; $R^{12}$ is H, $C_{1-3}$ alkyl, $C_{1-3}$ haloalkyl, $C_{2-3}$ alkenyl, or $C_{2-3}$ alkynyl; $R^{12}$ is $C_{4-6}$ alkyl, $C_{4-6}$ haloalkyl, $C_{4-6}$ alkenyl, or $C_{4-6}$ alkynyl; where $A^1$, $A^2$, $R^{12}$, and $X^1$ taken together have at least one carbon atom and one heteroatom; where the fragment formula weight of $A^1$ is greater than the fragment formula weight of $A^2$ (e.g., by at least 30 or 60); where the fragment formula weight of $A^2$ is greater than the fragment formula weight of $A^1$ (e.g., by at least 15 or 50); or combinations thereof.

Embodiments of the ninth aspect are compounds wherein $A^1$ is a side chain of any naturally occurring α-amino acid; wherein $A^1$ has a fragment formula weight of at least 50 (e.g., 70, 100, or 120).

Synthesis

The syntheses disclosed herein are organized by structure groups. A person of skill will recognize that claims 1–4 are related to claims 14–17, and so on. The synthesis of the compounds in claims 1–4 rely primarily on the results reported by Uno, et al. in their enantiospecific syntheses of (+)-lactacystin from (R)-glutamate [Uno, et al., *J. Am. Chem. Soc.* (1994) 116:2139]. Note that in all schemes relating to claims 1–4 and 14–17, when a straight line is used to connect $A^1$ (or anything corresponding to $A^1$) to the rest of the molecule, a dashed line should be assumed. The straight line is used simply for clarity. In other word all $A^1$ are attached to the rest of the molecule on the "alpha," i.e., the bottom, face.) Compound A-1 (Scheme 1) serves as the starting material for all synthetic routes proposed in claim 2, for example. Thus, conversion of A-1 to A-2, in analogy to the above-mentioned work allows for introduction of $R^1$ via standard alkylation chemistry. In the cases where

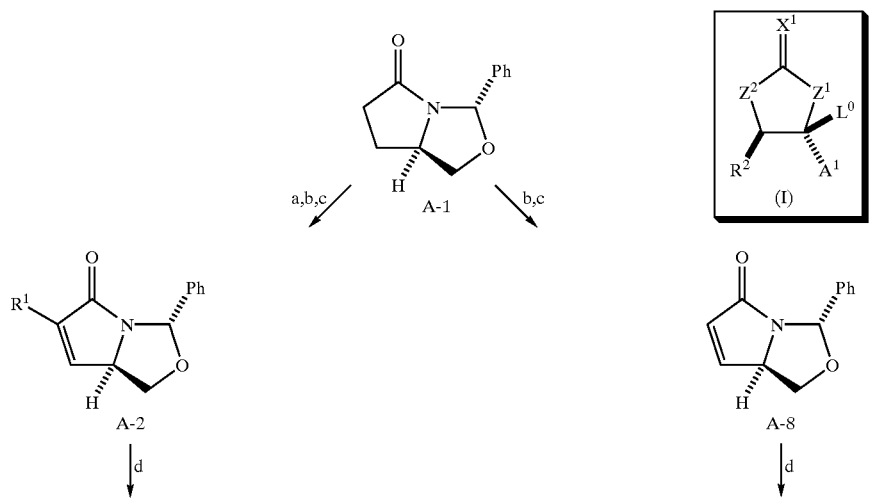

Scheme 1

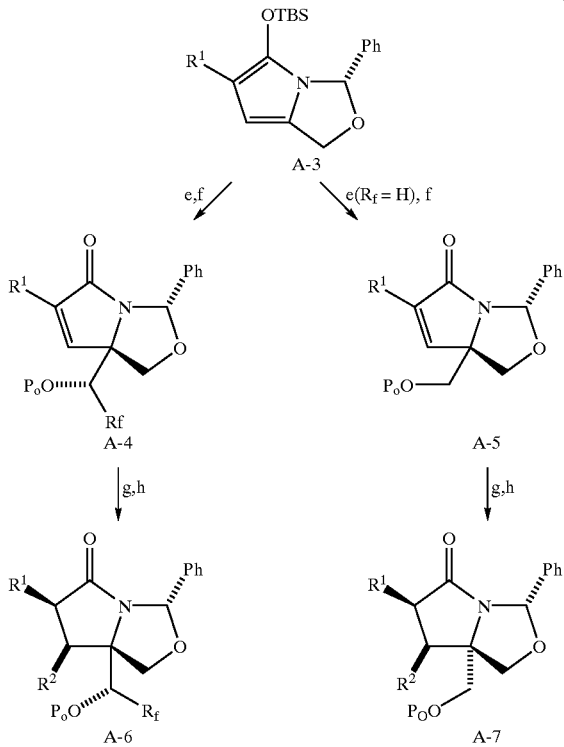
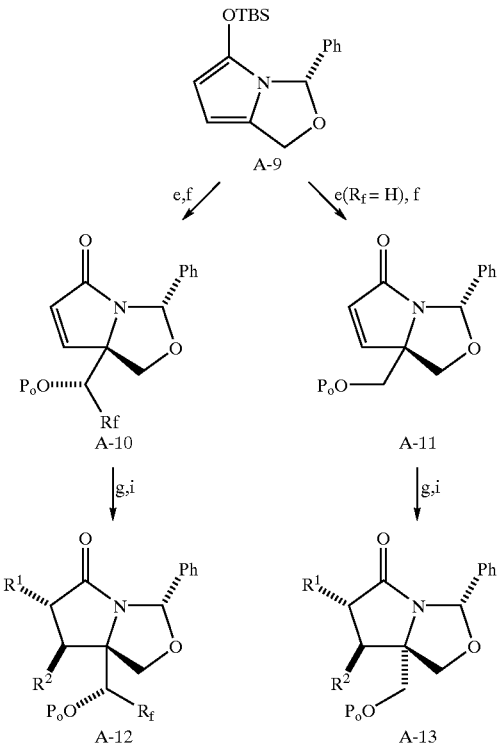

a) LDA; electrophile b) LDA; PhSeBr c) O₃; pyridine d) TBSOTf, 2,6-lutidine e) R_fCHO, SnCl₄, Et₂O f) Protect hydroxyl as P_oO g) Nucleophile corresponding to R² h) acidic water
i) Electrophile corrsponding to R¹

$R^1$ is hydroxyl, halide, —$SR_d$, or —$NR_dR_e$, wherein $R_d$ and $R_e$ each, independently, is selected from H, $C_{1-6}$ alkyl, $C_{1-6}$ haloalkyl, $C_{2-6}$ alkenyl, $C_{2-6}$ alkynyl, the electrophile in step b is, respectively, a N-arylsulfonyl-3-phenyloxaziridine [Davis, F. A. et al., *J. Org. Chem.* (1984), 49:3241], a N-halosuccinimide [Stotter, P. A. et al., *J. Org. Chem.* (1973) 38:2576], $R_d$ S—$SR_d$ or elemental sulfur [Zoretic, P. A. et al., *J. Org. Chem.* (1976) 41:3587] [Gassman, P. G. et al., *J. Org. Chem.* (1977) 42:3236], a N-arylsulfonylazide (followed by reduction of the azide to the primary amine and elaboration to $NR_dR_e$) [Evans, D. A. et al., *J. Am. Chem.* (1987) 109:6881]. If $R^1$ is labile or reactive, or both, a protecting group would be introduced at this point and removed at the end of the synthesis. The preparation of compounds of type A-2 is then completed with the two-step (steps b and c) process reported by Uno [Uno, et al., (1994)].

Introduction of $A^1$ is the next task. Uno [Uno, et al., (1994)] showed that under Lewis-acid mediated aldol addition conditions, $A^1$ is introduced with very high facial selectivity with respect to the bicyclic aminoacid derivative A-2. This carbon-carbon bond construction allows for the $A^1$ groups detailed in claim 2. Accordingly, conversion of A-2 to A-3, as described by Uno, followed by treatment of A-3 with $SnCl_4$ and an aldehyde ($R_fCHO$, where $R_f$ corresponds to H or to the rest of $A^1$), in diethylether yields aldol products A-4 (or A-5 if $R_f$ is H), following suitable protection of the hydroxyl group with a group designated here as $P_o$. [*Greene, et al., Protective Groups in Organic Synthesis*, 2nd ed., (1991)].

Introduction of $R^2$ by a stereoselective, conjugate nucleophilic addition to the unsaturated carbonyl system of A-4 or A-5, followed by quenching of the resulting enolate with acidic water gives access to compounds A-6 and A-7, respectively. This process is analogous to the "three-component coupling" strategy for prostaglandin synthesis of [Suzuki, et al. (1988)]. In this case, the three components are A-4 (or A-5), $R^2$, and a proton. The diastereomers shown for A-6 and A-7 are predicted to be the major ones based on several facts. The Uno synthesis [Uno, H., et al., (1994)1 used an $OsO_4$-catalyzed dihydroxylation of a compound similar to A-4 ($R^1$=methyl, $R_f$=iso-propyl) to introduce a hydroxyl group corresponding to $R^2$. This reaction proceeded with complete facial selectivity. Thus, in general, groups with appropriate reactivity (nucleophiles or electrophiles) similarly approach preferentially the "beta" face (from the top) of A-4 or A-5.

Quenching of the enolate with acidic water proceeds stereoselectively. In Suzuki's three-component coupling strategy, [Suzuki, et al., (1988)] the nucleophile and electrophile are introduced trans to each other. In our case, $R^2$ and the proton are introduced trans to each other. In the event that compounds in which $R^1$ and $R^2$ are trans to each other are desired, as depicted in compounds A-12 and A-13, a similar strategy has been devised.

The basic strategy has one exception to that detailed above: The order of introduction of $R^1$ and proton at the carbon alpha to the carbonyl is reversed. Thus, conversion of A-1 to A-9 is carried out using the same procedures as those for the preparation of A-3, omitting the alkylation step (step a). Elaboration of A-9 to A-10 and A-11 utilizes the same conditions as those which afford A-4 and A-5. Addition of $R^2$ still occurs from the top face, but the quenching step with an electrophile corresponding to $R^1$ now gives a trans relationship of $R^1$ and $R^2$, as shown in compounds A-12 and A-13.

Another advantage of these approaches to A-6, A-7, A-12, and A-13 is as follows. Should the quenching step introduce the electrophile (proton or $R^1$) cis to $R^2$ (opposite that predicted above), then one still has stereospecific routes to the desired compounds, except that A-4 and A-5 give A-12 and A-13, respectively, and A-10 and A-11 give A-6 and A-7.

Compounds in which $A^1$ is H are prepared by a different strategy (Scheme 2). For example, it has been shown that when $A^1$ is H, nucleophiles [Hanessian, et al., Synlett (1991) 10:222] and electrophiles [Griffart-Brunet, et al., Tet. Lett. (1991) 35:119] approach from the bottom face, cis to the hydrogen at $A^1$. Thus, the key to our strategy above is that the stereoselectivity of addition is reversed when $A^1$ is not H. The rapid preparation described below of compounds in which $A^1$ is H takes advantage of this reversal of stereoselectivity.

Thus, bromination of A-2 by standard methods [Caine, et al., J. Org. Chem. (1985) 50:2195] gives A-14, which is utilized in conjugate addition-elimination procedures to give compounds of type A-15. Since $A^1$ is H, catalytic hydrogenation of the olefin should install $R^1$ and $R^2$ in the desired cis configuration shown in compound A-16. Cleavage of the N,O-aminal may occur under such conditions, giving compound A-17. Such an occurrence is not disadvantageous since such a deprotection is the next step in the synthesis anyway. Compounds A-18 and A-19 are accessed by base-catalyzed epimerization of A-16 and A-17, respectively.

The above strategies allow for the preparation of compounds containing any and all $R^1$ and $R^2$ described in claims 2 and 15, with one exception: compounds where an additional ring is fused to the lactam ring (specifically, compounds in which $R^1$ is taken together with $R^2$, giving a bivalent moiety which forms a $C_{3-8}$ cycloalkyl, $C_{3-8}$ heteroaryl, $C_{3-8}$ heterocyclic radical, or $C_{6-12}$ aryl). Their preparation will be discussed below (Schemes 3 and 4). Note that while only carbocyclic systems are depicted in Schemes 3 and 4, both the alicyclic and heterocyclic (aromatic and non-aromatic in both cases) classes of compounds can be prepared in this manner by choice of the appropriate reagents. Further, all substitution patterns on these rings that are normally accessible by such processes are accessible by the methods proposed below. The simplest carbocyclic variants are shown for clarity and to illustrate the general strategy to these compounds.

The synthesis of these compounds relies on the diverse chemistry of cycloaddition [Carruthers, et al., Cycloaddition Reactions in Organic Synthesis (1990) and J. March, Advanced Organic Chemistry, (1992) pp. 826–877] to alpha-beta unsaturated olefins. Thus, as shown in Scheme 3, [1+2] processes (e.g. diazoinsertion, cyclopropanation, epoxidation, and aziridination) with compound A-20 (see Scheme 1 for preparation of compounds of this type, e.g. A-10 and A-11) gives access to compounds of type A-21. Compounds of type A-22 are prepared with a variety of [2+2] cycloaddition processes (e.g. photocycloadditions and ketene additions). 1,3-Dipolar cycloaddition chemistry ([3+2] cycladdtion reagents, such as nitrile oxides and azomethine ylides) prepares a wide variety compounds of the type A-23. The preparation of compounds of type A-24 is perhaps the most flexible and far-reaching of the cycloaddition chemistry because it relies on the Diels-Alder reaction, one of the most utilized and studied reactions in all of organic

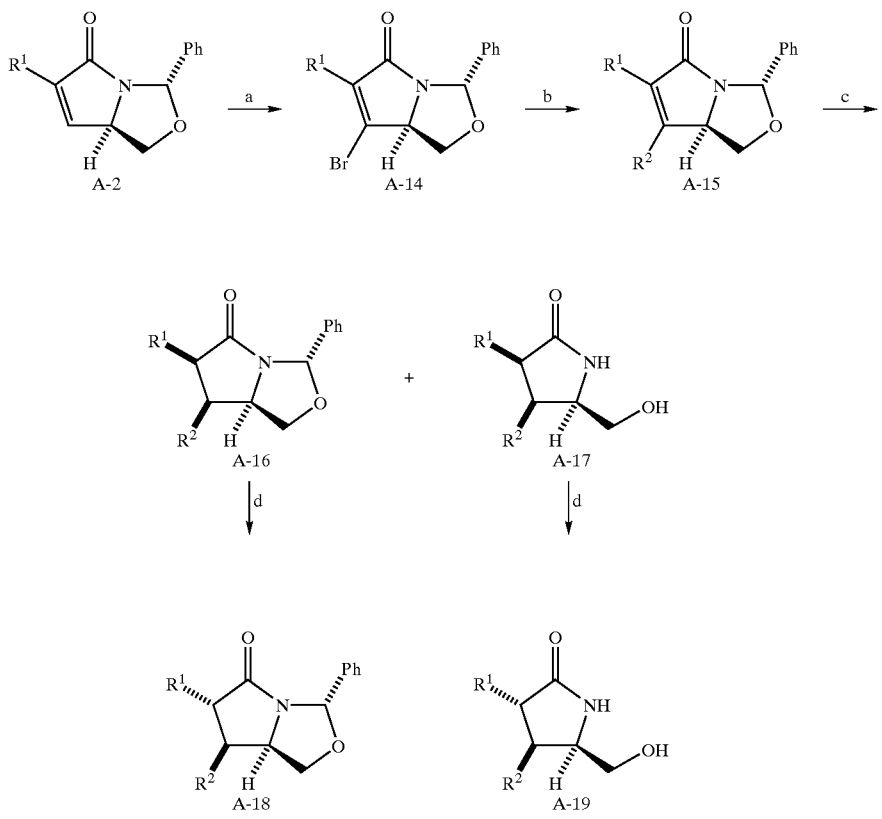

a) $Br_2$, $Et_3N$ b) Nucleophile corresponding to $R^2$; $H_3O^+$ c) $H_2$, Pd/C d) DBU, $CH_2Cl_2$

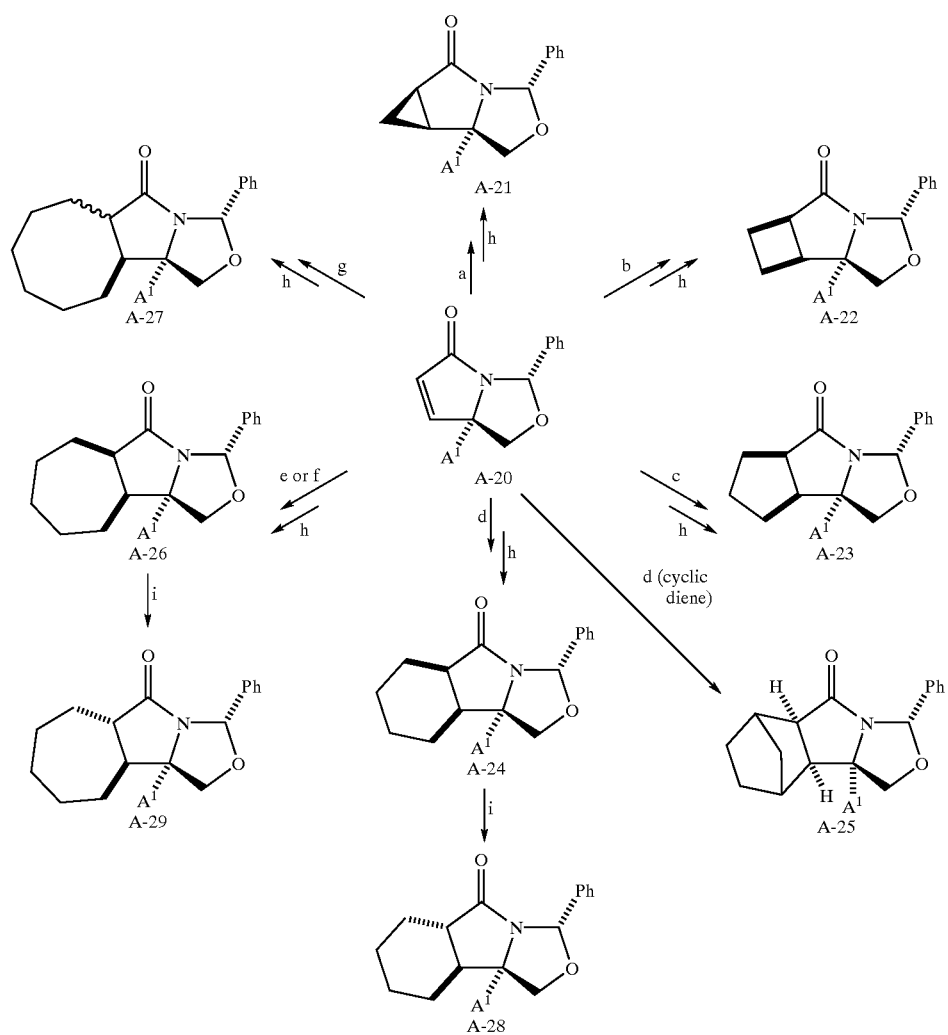
Scheme 3
a) epoxidation, Simmons-Smith, aziridination, etc. b) photocycloadditi on, ketene addition, etc. c) nitrile oxide, azomethine ylides, other [3+2] cycload ditions d) Diels-Alder cycloadditions, etc. e) [5+2] cycloadditions f) LG-$(CH_2)_5$-Nu g) LG-$(CH_2)_6$-Nu h) "functional group manipulation" i) DBU, $CH_2Cl_2$

Scheme 4

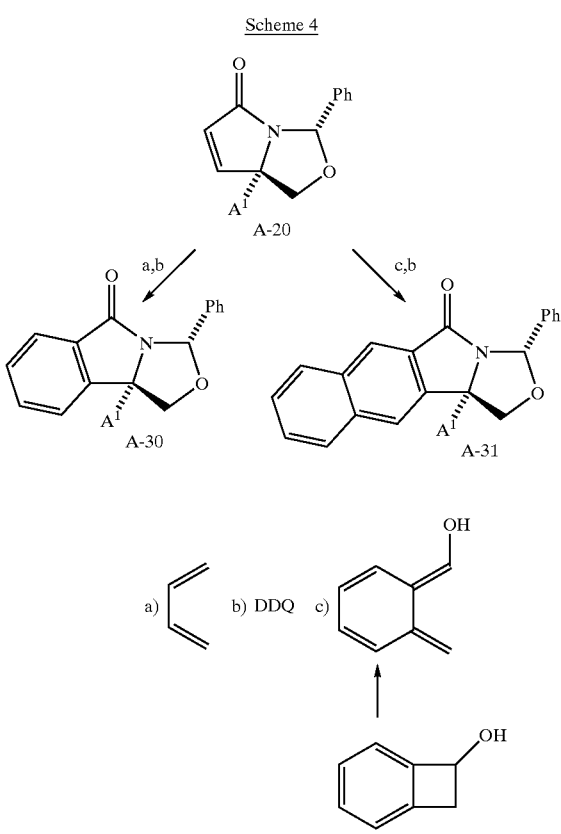

chemistry. The variety of compounds of type A-24 that are prepared by this method is far to great to detail; [Carruthers, (1990)] however, notably, bridged compounds (type A-25) are prepared by this method. [5+2] cycloadditions to give A-26 are less common, but some intriguing examples have been reported. [Wender, et al., *J. Org. Chem.* (1991) 56:6267 and Wender, et al., Tet. Lett. (1992) 32:6115].

While all these procedures introduce $R^1$ and $R^2$ cis to each other, base-catalyzed epimerization in the cases of A-24 and A-26 gives access to the trans-fused versions of these compounds, A-28 and A-29, respectively. (A-21, A-22, A-23, and A-25 can not be epimerized in this fashion, as these trans-fused rings suffer from much more ring strain than do the cis-fused systems.)

Cycloheptyl (A-26) and cyclooctyl (A-27) compounds are prepared with a slightly different process, one that is akin to that shown in Scheme 1. Fundamentally, one adds an nucleophile (abbreviated as "Nu") to A-20 which also has a leaving group (abbreviated as "LG") attached to the other end of the incoming nucleophile, separated by the necessary% number of atoms (5 in the case of A-26, 6 in the case of A-27). Thus, following the addition of the nucleophile, the resulting enolate displaces the leaving group, forming the ring. Alternatively, such a process is done stepwise in order to minimize undesired intramolecular side reactions of the nucleophile and electrophile. These and other methods for making cycloheptyl and cyclooctyl compounds from alpha-beta unsaturated carbonyl compounds have been reviewed in the chemical literature. [Petasis, N. A., et al., *Tetrahedron* (1992) 48:5757].

Aryl and heteroaryl compounds (e.g. compounds A-30 and A-31, Scheme 4) are prepared by [4+2] cycloaddition chemistry, followed by oxidation of the resultant cycloalkene or heterocycloalkene with dichlorodicyanoquinone (DDQ). [Pizey, N., *Synth. Reagents* (1977) 3:193–225]. In the case of compounds of type A-31, other types of dienes that are utilized are the hydroxyorthoxylylenes, formed by the ring opening reaction of hydroxybenzocyclobutenes. [Arnold, B. J., et al., *J. Chem. Soc.*, (1974) 409–415].

Thus, having prepared all the variations of $R^1$ and $R^2$, we turn now to the elaboration of these compounds to include all of the variations of $A^1$ (Scheme 5).

Based on the results of [Uno, et al., (1994)] and as shown in Scheme 1, Lewis-acid catalyzed aldol additions of A-3 to $R_fCHO$, followed by further elaboration, provide compounds of the type A-33 (Scheme 5) with the stereocenters in the configurations shown, including both configurations of $R^1$. (A straight bond (i.e. neither bold or dashed) is shown here to represent both diastereomers at this position.) Here we will focus on the stereochemistry of the secondary hydroxyl that is included in $A^1$, and related derivatives. While modification of conditions in the aldol addition (Scheme 1) reaction can provide the other diastereomer at this position, another method of inverting this center is to first oxidize to the ketone under standard conditions (e.g. Swern, Dess-Martin periodinane, etc.) and then reduce with the appropriate reducing agent (e.g. $NaBH_4$, etc.) whose identity is determined by screening a number of reductants. This two-step procedure provides compounds of type A-35. Analogously, reductive amination of ketone A-34 with an amine or hydroxylamine (represented in Scheme 5 as $R_nNH_2$) and sodium cyanoborohydride ($NaCNBH_3$) provides compounds of type A-36. The sense of stereochemical induction in this step can be altered by using a different reducing agent. Alternatively, by first preparing the

Scheme 5

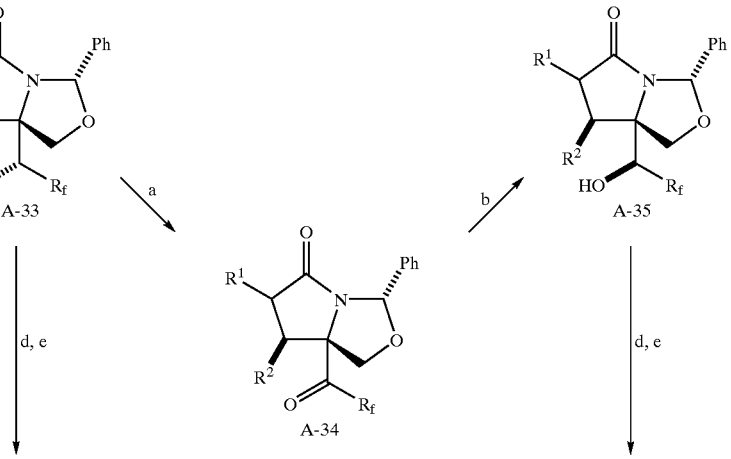

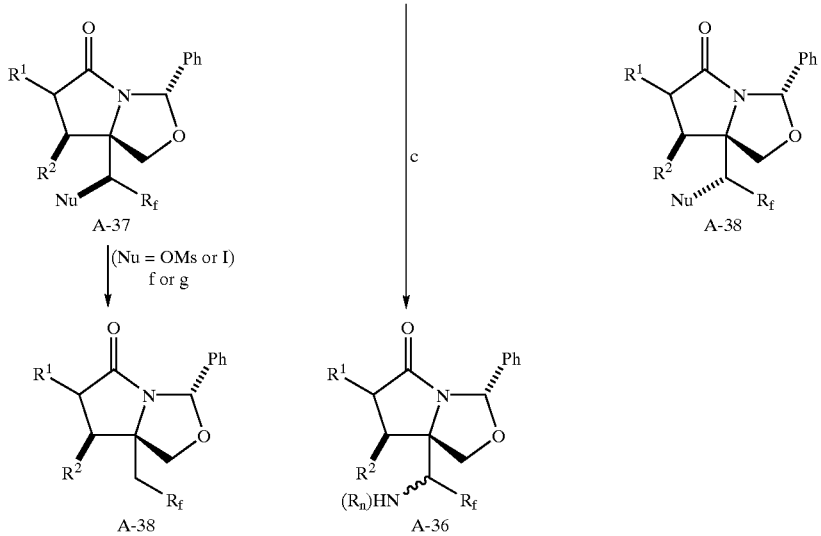

a) Dess-Martin periodinane b) NaBH₄, e.g. c) R$_n$NH$_2$, NaCNBH$_3$
d) MsCl, Et$_3$N e) Nucleophile f) LiEt$_3$BH g) Zn, HCl methanesulfonate ester ("mesylate") of A-33 or A-35, and then displacing the mesylate with a nucleophile (e.g. RNH$_2$, RS-, RO-, halide, hydroxylamine, Grignard reagents, etc.) one obtains a wide variety of A$^1$ derivatives with complete control of stereochemistry at the carbon corresponding to the secondary hydroxyl in A-33. Reduction of the mesylate (with lithium triethylborohydride (LiEt$_3$BH)) or of a halide (with, e.g., zinc in hydrochloric acid) provides compounds of the type A-38.

Another method to produce the various A$^1$ derivatives is depicted in Scheme 6. Compounds of the type A-39, which are prepared according to Scheme 1, are converted to those of type A-40 where X$_a$ is a halide or trifluoromethanesulfonate ester ("triflate"), for example, using standard functional group manipulation. Displacement of these leaving groups with nucleophiles gives another method for the preparation of compounds of type A-38. Subjecting iodide A-40 (X$_a$ is I) to metal-halogen exchange conditions (e.g. activated Mg metal or tert-butyllithium) provides nucleophiles to which a variety of nucleophiles can be added, providing yet another route to compounds of type A-38.

Another strategy for the preparation of a subset of compounds of type 33 is worth noting (Scheme 7). This strategy allows for the preparation of compounds of type A-33 for all R$^2$ discussed above and for all R$^1$ other than hydroxyl, halide, —SR$_d$, —NR$_d$R$_e$. Compounds of the type A-4, A-5, A-10, and A-11 as shown in Scheme 1 (represented as compound A-41 in Scheme 7), in which R$^1$ is attached to the lactam ring with a carbon-carbon bond, can be dihydroxylated to give compounds of type A-42, in which the hydroxyl groups have been added to the top face exclusively. [Uno, et al., (1994)] (The reasons for this stereoselectivity have been discussed above.) Following the procedure of [Uno, et al., Scheme 6

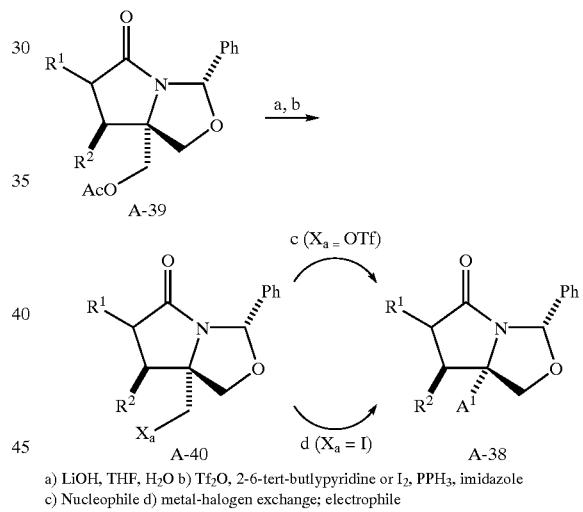

a) LiOH, THF, H$_2$O b) Tf$_2$O, 2-6-tert-butlypyridine or I$_2$, PPH$_3$, imidazole
c) Nucleophile d) metal-halogen exchange; electrophile Scheme 7

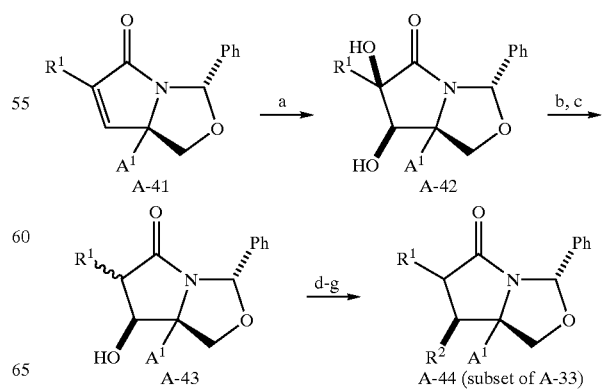

-continued a) OsO₄, NMO, water, acetone b) TCDI c) Bu₃SnH, AIBN d) seperate diastereomers
e) DEAD, Ph₃P, acetic acid f) conversion of acetate to leaving group g) nucleophil e corresponding to R²

(1994)] the tertiary hydroxyl can be removed selectively, yielding a mixture of $R_i$ diastereomers A-43, which can be separated by a variety of chromatographic methods. Mitsunobu inversion of the secondary hydroxyl, followed by displacement of a suitably derived leaving group by any nucleophile corresponding to $R^2$ (e.g. hydroxide, alkoxide, sulfide, Grignard reagents, amine, halide, etc.) gives compounds of the type A-44, which are a subset of compounds of the type A-33, and can therefore be elaborated into their corresponding $A^1$ derivatives as described above.

Thus, having provided viable routes to all variations of $R^1$, $R^2$, and now $A^1$ in claims 2 and 15, we now turn our attention to the installation of $X^1$, $L^1_1$ and $X^2$ (Scheme 8).

The compound of general structure A-45 can be converted to A-46 in a two-step process involving first catalytic hydrogenolysis or mild acidic hydrolysis [Corey, E. J., et al., *J. Am. Chem. Soc.* (1972), 94:6190] and then protection of the primary hydroxyl group as its tert-butyldimethylsilyl (TBS) ether under standard conditions. [Corey, E. J., et al., *J. Am. Chem. Soc.* (1992), 114:10677] N-Alkylation of the amide provides access to compounds A-47. [Challis, N., *The Chemistry of Amides*, (1970) 734–754]. (In the cases where $R_b$ is desired to be H, the amide can be blocked with a suitable protecting group that will be removed at the end of the synthesis. [Greene, T. W., et al., *Protective Groups in Organic Synthesis* (1991)].

Enamine A-48 can be prepared from A-47 under Tebbe olefination conditions. [Pine, S. H., et al., *J. Org. Chem.* (1985) 50:1212]. Thioamide A-49 can be prepared by treatment of A-47 with bis(tricyclohexyltin)sulfide and boron trichloride. [Steliou, K., et al., *J. Am. Chem. Soc.*, (1982) 104:3104]. Substituted enamines A-50 can be prepared

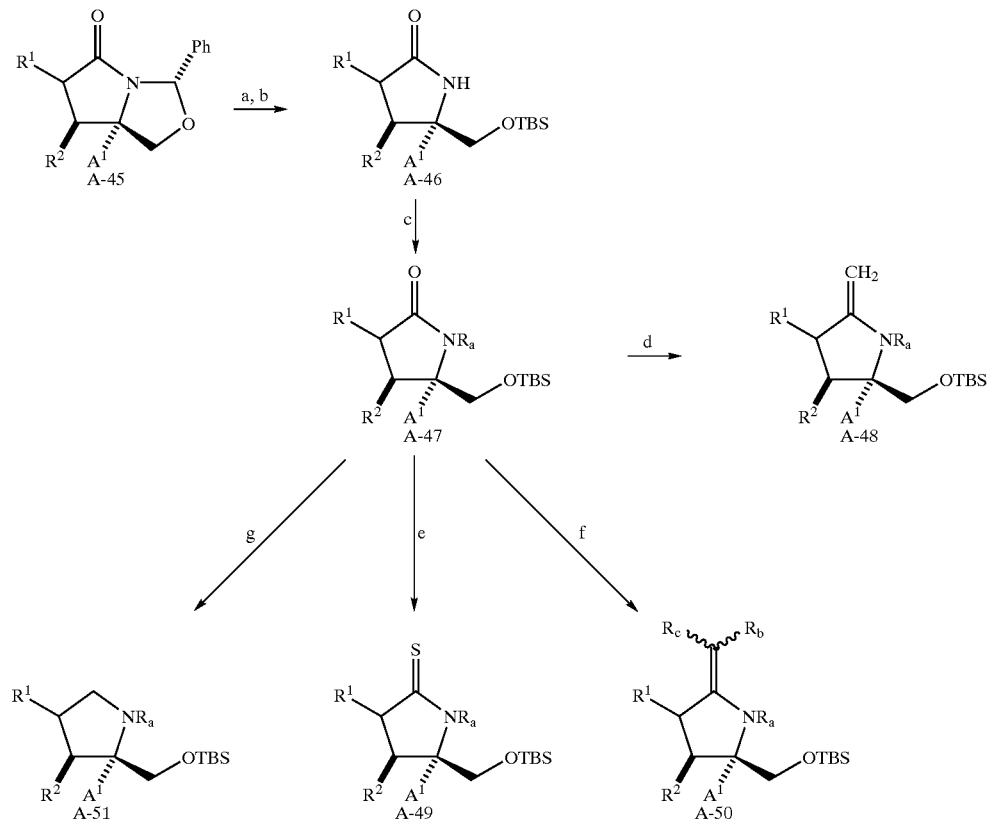

Scheme 8 a) H₂, Pd/C, H⁺ or HS(CH₂)₃SH, HCl, CF₃CH₂OH b) TBS-Cl, imidazole, DMF
c) NaH, electrophile corresponding to $R_a$, DMF d) Tebbe olefination
e) ((cyclohexyl)₃Sn)₂S, BCl₃ f) $R_cR_bC(H)(MgBr)$; H⁺ g) LiAlH₄, Et₂O h) Raney Ni by addition of the appropriate Grignard reagent or alkyllithium to A-47 or A-49, followed by acidic hydrolysis, and separation of the E and Z olefin isomers. [Aguerro, A., et al., *J. Chem. Soc., Chem. Commun.* (1986) 531 and Schrock, R. R., *J. Am. Chem. Soc.*, (1976) 98:5399, and Hansen, C., *J. Org. Chem.* (1973) 38:3074]. Pyrrolidines of type 51 can be prepared by reduction of A-47 with lithium aluminum hydride [March, J., *Advanced Organic Chemistry* (1992) 826–877 and Gaylord, J., *Reduction With Complex Metal Hydrides* (1956)] 544–636] or alternatively by reduction of A-49 with Raney nickel. [Belen'kii, W., *Chemistry of Organosulfur Compounds* 91990) 193–228].

Taken together, these procedures constitute a synthesis of compounds of the general structure A-52, which are converted to A-53 following, for example, the procedure of Uno, et al. [Uno, H., et al., (1994)] (Scheme 9). Compounds A-53 are converted to analogues A-54a via oxidation to the acid and coupling with $L^1$ (all of which can be prepared by standard methods) under the conditions utilized by Corey and Reichard [Corey, E. J., et al., (1002a)]. Sulfurization of these compounds with Lawesson's reagent [Cava, M. P., et al., *Tetrahedron* (1985) 41:5061] gives thiono analogues A-55a. Compounds A-54b are prepared via addition of a nucleophile (e.g. $CF_3$) [Francese, C., et al., *J. Chem. Soc., Chem. Commun* (1987) 642], corresponding to $L^2$ to the aldehydes A-54b followed by oxidation of the alcohol with Dess-Martin periodinane. [Linderman, R. J., et al., Tet. Lett. (1987) 28:4259]. Sulfurization of these compounds with Lawesson's reagent [Cava, M. P., et al., (1985)] gives thiono analogues A-55b. Epoxides of the type A-55c are prepared from A-53 or A-54b by the method of Johnson [Johnson, C. R., *Acc. Chem. Res.* (1973) 6:341], thus completing the synthesis of all the analogues detailed in this section.

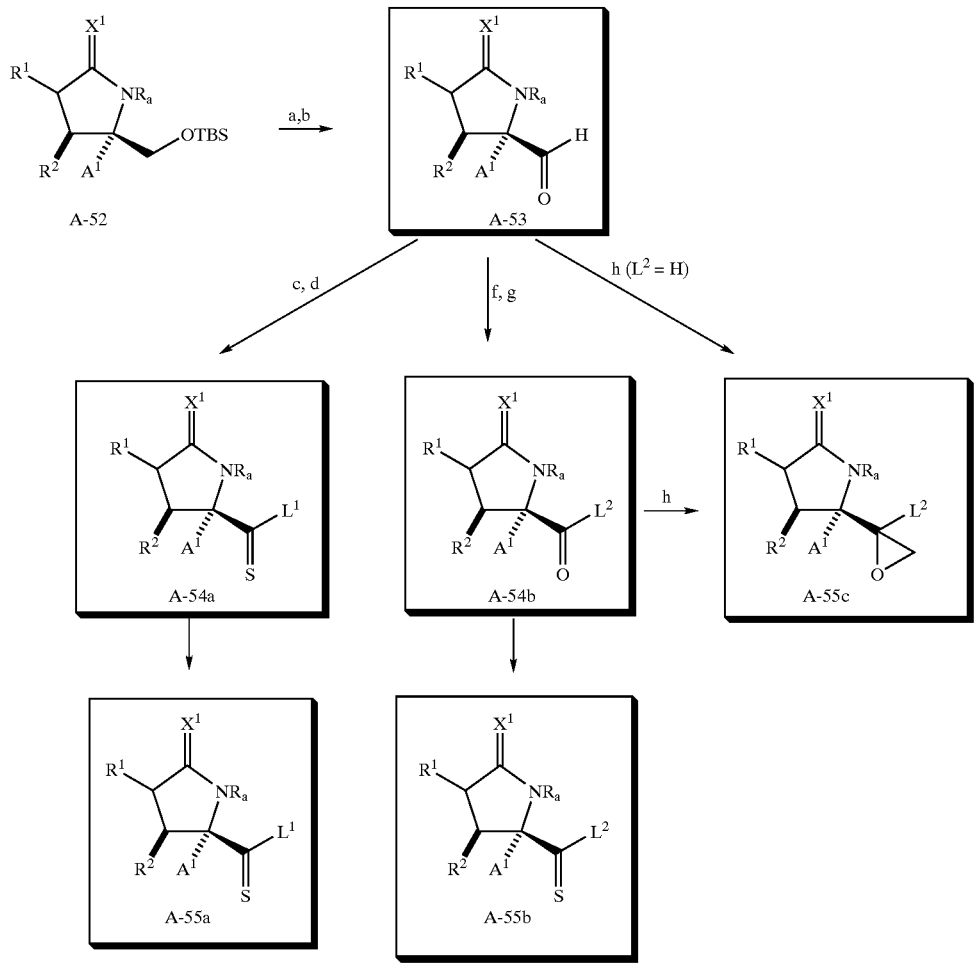

Scheme 9 a) TBAF, THF or HF, $CH_3CN$ or 1% HCl, MeOH b) $(COCl)_2$, DMSO, $Et_3N$, $CH_2Cl_2$
c) $NaClO_2$, pH 7, THF d) $L^1$—H, BOP-Cl e) Lawesson's reagent f) Nucleophile corresponding to $L^2$ g) Dess-Martin periodinane h) $Me_2(S^+)(O)CH_2^-$

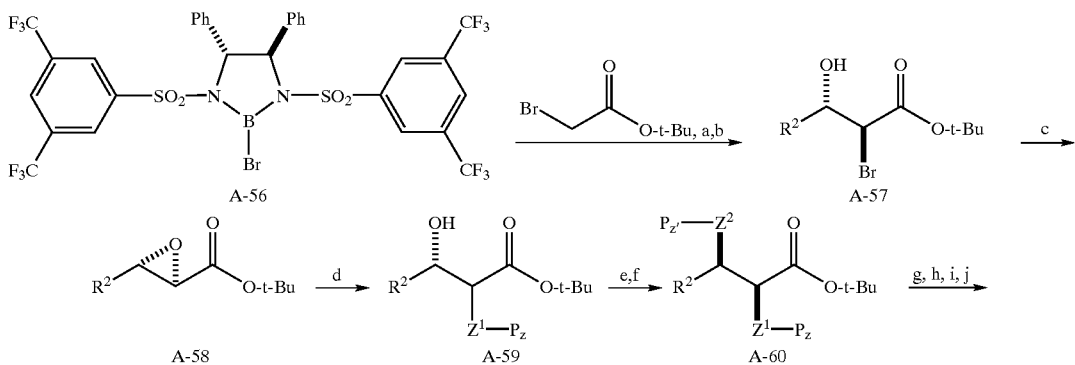

Scheme 10

-continued

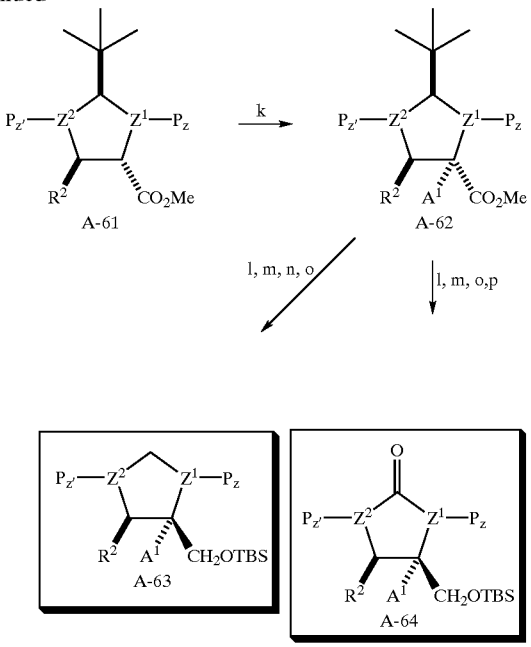

a) Et$_3$N, toluene b) R$_f$CHO c) K$_2$CO$_3$, MeOH, H$_2$O d) nucleophile corresponding to Z$^1$; protection of Z$^1$, if necessary e) TsCl, pyridine f) nucleophile corresponding to Z$^2$; protection of Z$^2$, if necessary g) deprotect P$_Z$ and P$_{z'}$, if necessary h) MeSO$_3$H, toluene i) CH$_2$N$_2$ j) (CH$_3$)$_3$CCHO, acid k) LiHMDS; electrophile corresponding to A$^1$ l) LiAlH$_4$ m) TBS-Cl, imidazole, DMF n) acidic water o) HCHO, acid p) CDl The preparation of the compounds covered by claims 4 and 17 relies primarily on the methods of Seebach and of Corey. Thus, as shown in Scheme 10, epoxides of the type A-58 are prepared according to the procedure of Corey, et al., [Corey, E. J., et al., (1992b)] from 61 via compound 62. R$^2$ is thus installed by choosing the appropriate aldehyde for the aldol reaction in step a. Corey [Corey, E. J., et al., (1992b)] showed that epoxides A-58 are opened stereospecifically to give A-59. Thus, Z$^1$ is installed by treating A-58 with a nucleophile corresponding to Z. (P$_z$ refers to a protecting group for Z$^1$.) Installation of Z2 is accomplished by conversion of the hydroxyl A-59 to a leaving group, for example, a tosylate, and displacement of the leaving group with a nucleophile corresponding to Z$^2$. (P$_z$, refers to a protecting group for Z$^2$).

The results of Seebach [Seebach, D., et al., *Helv. Chim. Acta.* (1987) 70:1194] are used in the next part of the synthesis. Conversion of A-60 to A-61 allows for enolization and alkylation with an electrophile corresponding to A$^1$, yielding A-62. Seebach showed that such alkylations give predominantly the diastereomer shown.

After reduction of the ester and protection of the resulting primary alcohol as the TBS ether, removal of the tert-butylmethylene protecting group, enables conversion to compounds of either the type A-63 (by treatment with, for example, formaldehyde and an acid catalyst) or the type A-64 (by treatment with, for example, CDI) is effected.

Compound is a key intermediate in the completion of the synthesis of the compounds in claims 4 and 17, (Scheme 11). Compounds of the type A-65 are prepared from A-64 under Tebbe olefination conditions. [Pine, S. H., et al., (1985)]. Compounds of the type A-66 are prepared by treatment of A-64 with bis(tricyclohexyltin)sulfide and boron trichloride. [Steliou, K., et al., (1982)]. Compounds of the type A-67 are prepared by addition of the appropriate Grigard reagent or alkyllithium to A-64 or A-66, followed by acidic hydrolysis, and separation of the E and Z olefin isomers. [Aguerro, A., et al., (1986) and Schrock, R. R., (1976), and Hansen, C., et al., (1973)]. Compounds of the type A-63, prepared in Scheme 10, are also prepared by reduction of A-64 with lithium aluminum hydride [March, J., (1992), and Gaylord, J. (1956)] or alternatively by reduction of A-66 with Raney nickel. [Belen'kii, W., (1990)].

Taken together, compounds of the type A-63, A-64, A-65, A-66, and A-67 are of the general class A-68, which are converted the general class of lactacystin analogues A-69 by fluoride deprotection of the TBS ether, oxidation of the resulting primary alcohol to the carboxylic acid, via the aldehyde analogues, in, for example, the two-step process shown, and coupling with L$^1$ using the method of Corey and Reichard, [Corey, E. J., et al., (1992a)] and removal of the protecting groups on Z$^1$ and Z$^2$ (if necessary). Lactacystin analogues A-71 are prepared by treating A-69 with Lawesson's reagent [Cava, M. P., et al., (1985)]. Analogues A-70 are also prepared from A-68 by fluoride deprotection of the TBS ether, oxidation of the resulting primary alcohol to the aldehyde, addition of nucleophile (e.g., CF$_3$) [Francese. C. et al., (1987)] Dess-Martin periodinane sulfurization with Lawesson's reagent (if desired) [Cava, M. P., oxidation (1985)], and deprotection of Z$^1$ and Z2, if necessary. Epoxides of the type A-72 are also prepared from A-68 by fluoride deprotection of the TBS ether, oxidation of the resulting primary alcohol to the aldehyde, addition of a nucleophile corresponding to L$^2$, Dess-Martin periodinane oxidation, dimethyloxosulfonium methylide, and deprotection of Z$^1$ and Z$^2$ (if necessary). Thus, the above strategy prepares all the compounds in claims 4 and 17.

Scheme 11
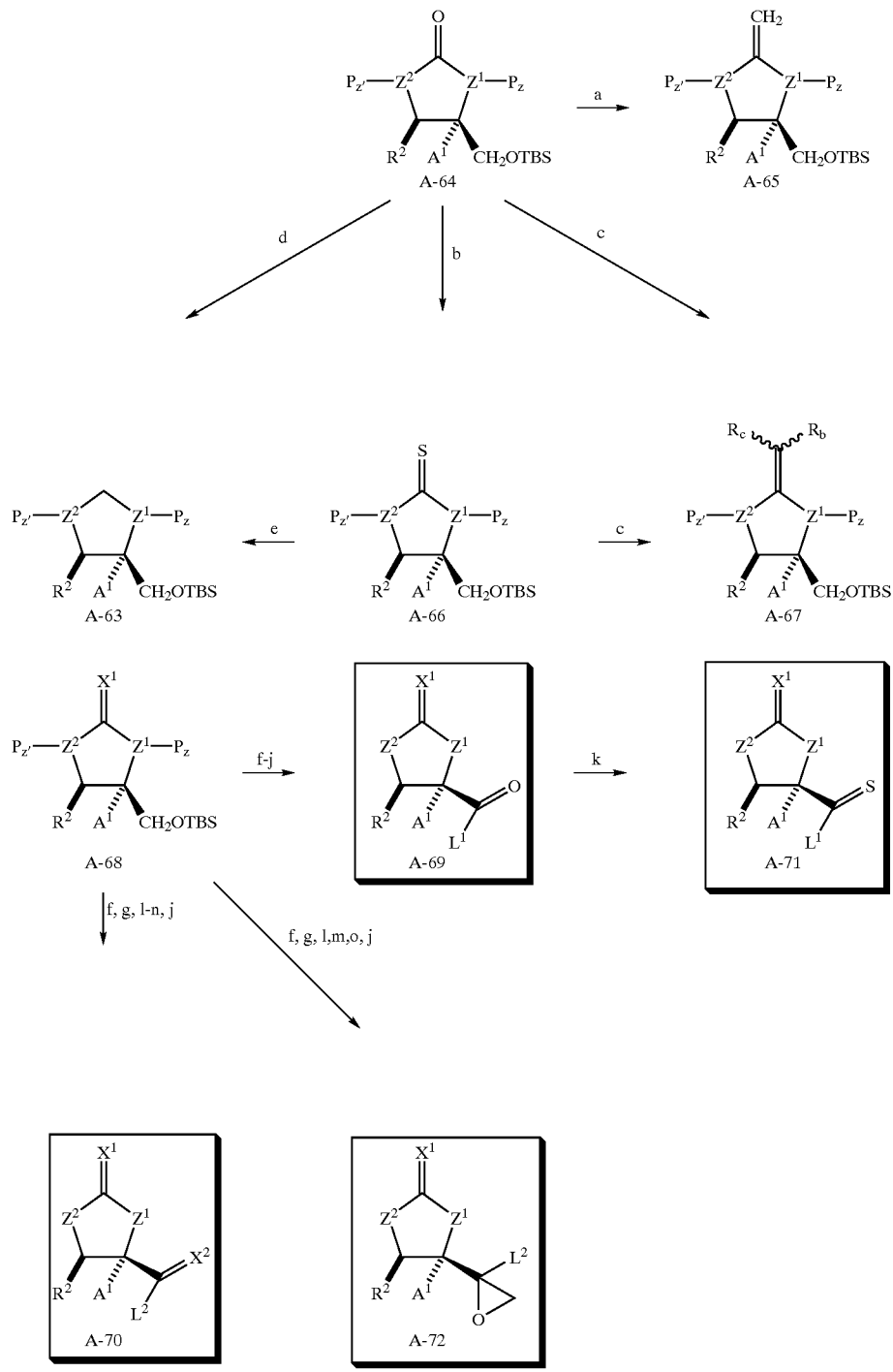
a) Tebbe olefination b) ((cyclohexyl)$_3$Sn)$_2$S, BCl$_3$ c) R$_c$R$_b$C(H)(MgBr); H$^+$ d) LiAlH$_4$, Et$_2$O
e) Raney Ni f) TBAF, THF g) Swem oxidation h) NaClO$_2$, Na$_2$HPO$_4$ i) L$^1$-H, BOP-Cl
j) deprotection, if necessary k) Lawesson's reagent l) Nucleophile co rreponding to L$^2$
m) Dess-Martin periodinane n) Step k, if desired o) Me$_2$(S$^+$)(O)CH$_2^-$ Scheme 12

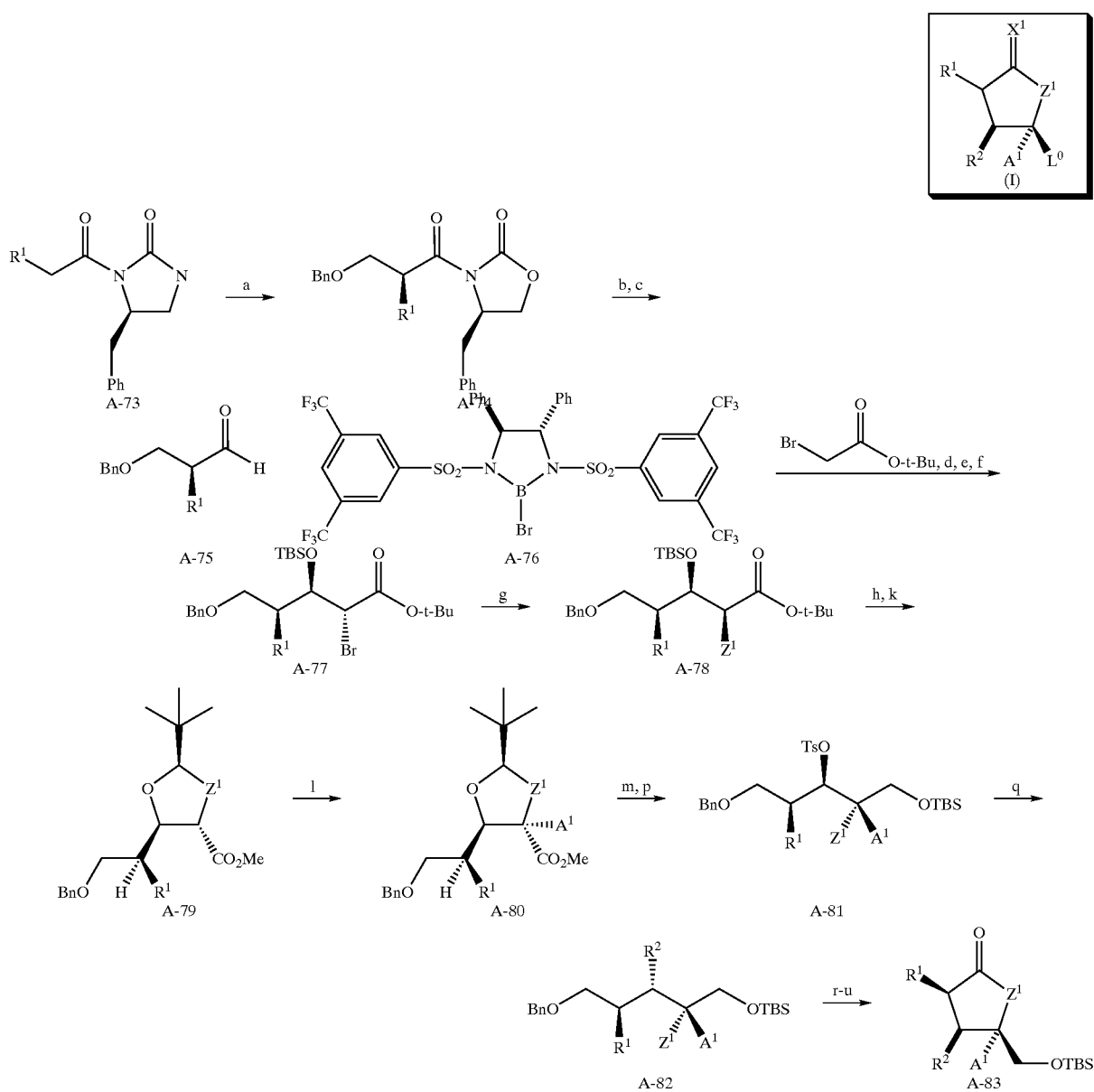

a) LDA; BnOCH₂Br b) LiAlH₄ c) Swern Oxidation d) Et₃N, toluene e) A-75 f) TBS-Cl, imidazole, DMF g) Nucleophile corresponding to $Z^1$ h) MeSO₃H i) CH₂N₂ j) TBAF, THF k) (CH₃)₃CCHO, acid catalyst l) LiHMDS, electrophile corresponding to $A^1$ m) LiAlH₄ n) TBS-Cl, imidazole, DMF o) deprotection p) TsCl, pyridine q) Nucleophile corresponding to $R^2$ r) H₂, Pd/C s) oxidation t) deprotect $Z^1$, if necessary u) cyclize (with DCC, for example)

The preparation of the compounds covered by claim 1 relies primarily on the methods of Evans and of Corey. Thus, as shown in Scheme 12, chiral oxazolidinones of the type A-73 are enolized and alkylated with benzyloxybromomethane, thereby installing $R^1$. [Evans, D. A., et al. J. Am. Chem. Soc., (1982) 104:1737]. (Only one configuration of $R^1$ is obtained in the reaction. The other configuration of $R^1$ is obtained by using the opposite enantiomer of the chiral oxazolidinone.) Conversion of A-74 to aldehydes of the type A-75, and chiral, boron-mediated (using A-76) aldol condensation with tert-butylbromoacetate gives [Corey, E. J., et al., (1992b)] a secondary alcohol that is protected as the tert-butyldimethylsilyl (TBS) ether to give compounds of the type A-77. Displacement of the bromide with a nucleophile [Corey, E. J., et al. (1992b)] corresponding to $Z^1$ yields A-78, which can be converted to compounds of the type A-79. As discussed above regarding claim 4, such compounds can be enolized and alkylated stereospecifically with electrophiles corresponding to A giving A-80. Standard functional group manipulation yields tosylates of the type A-81. Displacement of the tosylate with a nucleophile corresponding to $R^2$, [Hanessian, S., et al., J. Org. Chem. (1989) 54:5831] gives compounds of the type A-82, the primary alcohol of which is deprotected via, for example, catalytic hydrogenolysis, and cyclized to compounds A-83 after oxidation of the primary alcohol to the carboxylic acid.

As shown in Scheme 13, compounds of the type A-84, in which $R^1$ is in either the (R) or (S) configuration, are converted into a variety of $X^1$ variants. Compounds of the type A-85 are prepared from A-84 under Tebbe olefination conditions. [Pine, et al., (1985)] Compounds of the type A-86 are prepared by treatment of A-84 with

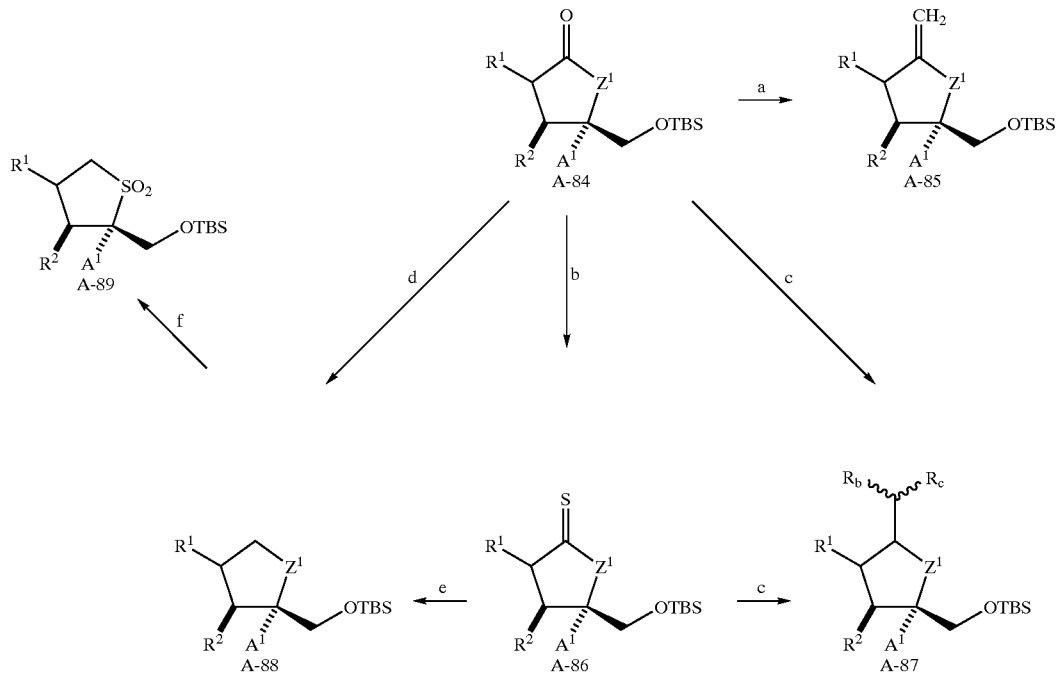

Scheme 13a a) Tebbe olefination b) ((cyclohexyl)$_3$Sn)$_2$S, BCl$_3$ c) R$_b$R$_c$C(H)(MgBr); H$^+$ d) LiAlH$_4$, Et$_2$O
e) Raney Ni f) KHSO$_5$ g) TBAF, THF h) Swern oxidation i) NaClO$_2$, NaH$_2$PO$_4$ j) L$^1$-H, BOP-Cl k) Lawesson's reagent

Scheme 13b

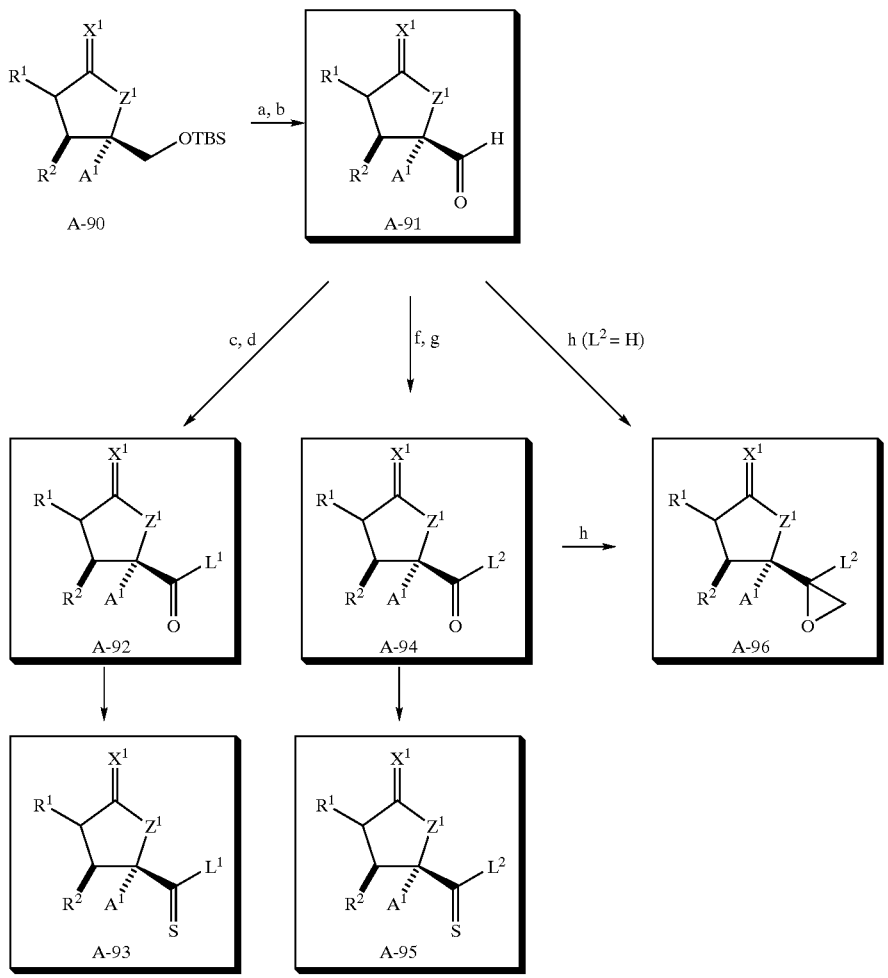

a) TBAF, THF or HF, CH$_3$CN or 1% HCl, MeOH b) (COCl)$_2$, DMSO, Et$_3$N, CH$_2$Cl$_2$
c) NaClO$_2$, pH 7, THF d) L$^1$-H, BOP-Cl e) Lawesson's reagent f) Nucleophile
corresponding to L$^2$ g) Dess-Martin periodinane h) Me$_2$(S$^+$)(O)CH$_2$$^-$ bis(tricyclohexyltin)sulfide and boron trichloride. [Stelious, K., et al., (1982)]. Compounds of thetype A-87 are prepared by addition of the appropriate Grignard reagent or alkyllithium to A-84 or A-86 followed by acidic hydrolysis, and separation of the E and Z olefin isomers. [Aguerro, A., et al., (1986), Schrock, R. R., (1976), and Hansen C., et al., (1973)]. Compounds of the type A-88 are prepared by reduction of A-84 with lithium aluminum hydride [March, J. (1992), and Gaylord, J., (1956)] or alternatively by reduction of A-86 with Raney nickel. [Belen'kii, W., (1990)]. When Z$^1$ is S in A-88, oxidation to the cyclic sulfone variants is effected with, for example, KHS05. [Trost, B. M., et al., Tet. Lett. (1981) 22:1287].

Taken together, compounds of the type A-84, A-85, A-86, A-87, A-88, and A-89 are of the general class A-90, which are converted analogues A-91, following for example, the procedure of Uno, et al. [Uno, H., et al., (1994)] (Scheme 13b). Compounds A-91 are converted to analogues A-92 via oxidation to the acid and coupling with L$^1$ (all of which can be prepared by standard methods) under the conditions utilized by Corey and Reichard. [Corey, E. J., et al., (1992a)]. Sulfurization of these compounds with Lawesson's reagent gives thiono analogues A-93. Compounds A-94.are prepared via addition of a nucleophile (e.g. CF$_3$) [Francese, C., et al., (1987)] corresponding to L$^2$ to the aldehydes A-91 followed by oxidation of the alcohol with Dess-Martin periodinane. Sulfurization of these compounds with Lawesson's reagent gives thiono analogues A-95. Epoxides of the type A-96 are prepared from A-91 or A-94 by the method of Johnson, thus completing the synthesis of all the analogues detailed in this section. Note: As above in all Schemes relating to claim 6, when a straight line is used to connect A$^2$ (or anything corresponding to A$^2$) to the rest of the molecule, a dashed line should be assumed. The straight line is used simply for clarity. All A$^2$ are attached to the rest of the molecule on the "alpha" face (i.e. the bottom face).

The proposed syntheses of all of the compounds listed in claim 5 rely on a key intermediate from Scheme 9. As shown in Scheme 14, compounds of type B-1 are analogous to a subset of compounds A-53, whose various preparations were described in Schemes 1, 2, and 5-8, and described in the accompanying text.

In order to prepare analog B-2, the method of Corey, et al. is utilized. [Corey, E. J., et al., Tet. Lett. (1993) 34:6971]. Sulfurization of B-2 with, for example, Lawesson's reagent [Cava, M. P., et al., (1985)] provides analogs B-3.

The preparation of compounds of type B-1 is summarized in Scheme 15. Thus the same starting material (A-1) as that used in Scheme 1 is elaborated to all of the compounds B-2 by the same methods as those used in Schemes 1, 2, 5, 6, and 8. There are then two possible general strategies for the conversion of these intermediates to B-2. The first is analogous to that detailed in Schemes 1, 2, 5, 6, 8, and 9, in which $Z^5$ (suitably activated or protected) serves as the inucleophile in the relevant reactions.

The other strategy, based on that shown in Scheme 7 is also depicted in Scheme 15. Thus, dihydroxylation of B-4 gives B-5, which is then be deoxygenated as before, giving B-6. Separation of the diastereomers, Mitsunobu inversion of the secondary hydroxyl, and displacement of a leaving group derived from the Mitsunobu product provides compounds of the type B-7, which are then elaborated to B-1 as described in Schemes 8 and 9.

Scheme 14

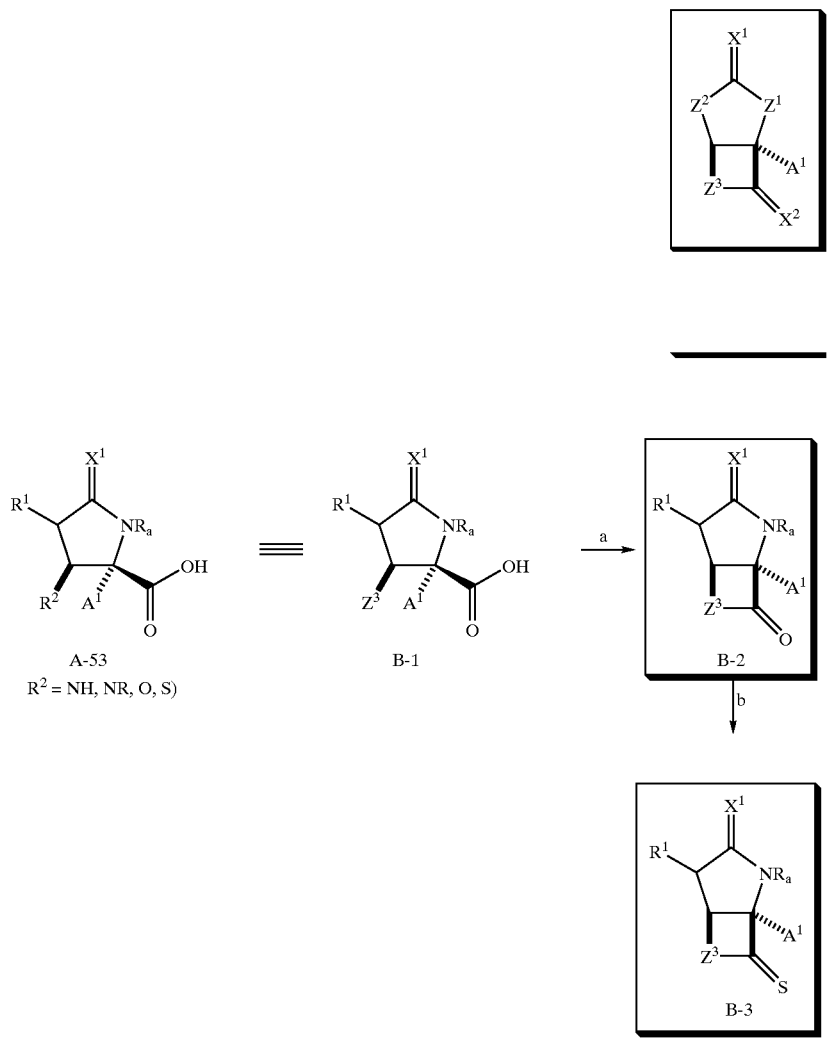

a) BOP-Cl b) Lawesson's reagent

Scheme 15

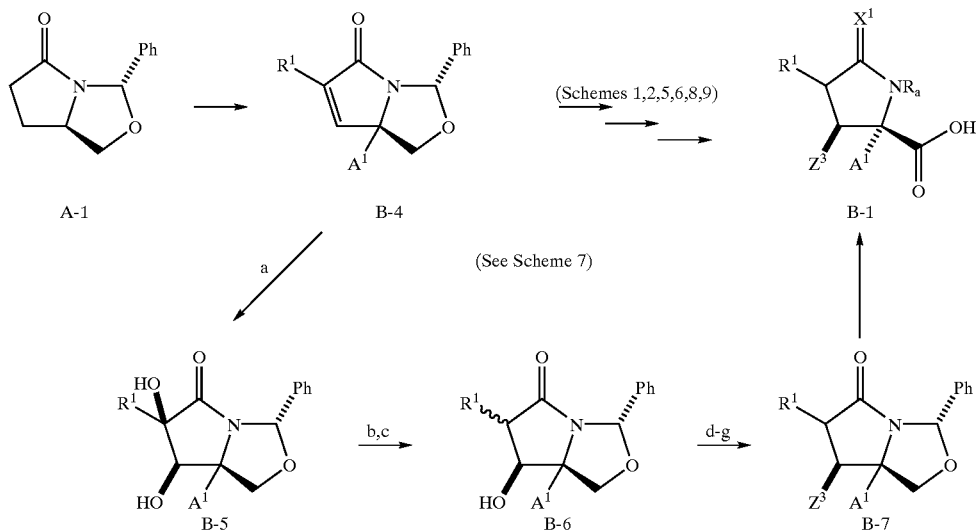

a) OsO4, NMO, water, acetone b) TCDI c) Bu3SnH, AIBN d) seperate diastereomers
e) DEAD, PPh3, acetic acid f) conversion of acetate to leaving group g) nucleophile
corresponding to $Z^3$, h) see Schemes 8 and 9

The proposed syntheses of all of the compounds listed in claim 5 rely on intermediate A-81 from Scheme 12. As shown in Scheme 16, compounds of type B-11 are analogous to a subset of compounds A-81, whose various preparations are illustrated in Scheme 12, and described in the accompanying text. Conversion of compounds of the type B-11 to B-12 is performed in analogy to Scheme 12. Compounds of the type B-13 are prepared from B-12 following the relevant steps in Schemes 13a and 13b.

In order to prepare analogs B-14, the method of Corey, et al. is utilized. [Corey, E. J., et al., (1993)] Sulfurization of B-14 with, for example, Lawesson's reagent [Cava, M. P., et al., (1985)] provides analogs B-15.

The preparation of the compounds covered by claim 7 relies on a key intermediate from Scheme 7. As shown in Scheme 21, compound C-1 is analogous to A-41, whose preparation is illustrated in Scheme 7 and described in the accompanying text. (There are no Schemes 17–20.) Following the work of Fuchs, [Hutchinson, D. K., et al., *J. Am. Chem. Soc.* (1987)] C-1 is treated sequentially with bis (benzyloxymethyl)lithiumcuprate and acidic water, giving compounds of the type C-2. Both configurations of $R^7$ can be accessed. See Schemes 1 and 2 for details. As in Scheme 8, mild acidic hydrolysis, protection of the primary hydroxyl, and alkylation or protection of the nitrogen gives compounds C-2.

Deprotection of the benzyl group by, for example, catalytic hydrogenolysis followed by displacement of the derived tosylate with a nucleophile corresponding to $Z^7$, accesses compounds C-3, in which $Z^7$ is protected, if necessary. Elaboration to carboxylic acids C-4 follows the same set of reactions in Schemes 8 and 9, allowing the preparation of all $X^9$ variants. Deprotection of $Z^7$, if

Scheme 16

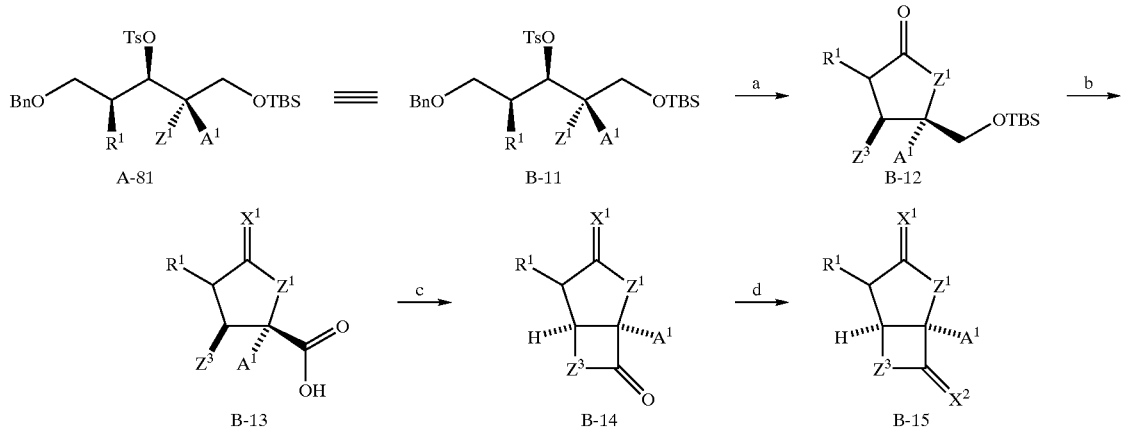

a) See Scheme 12 b) See Scheme 13b c) BOP-Cl d) Lawesson's reagent

-continued

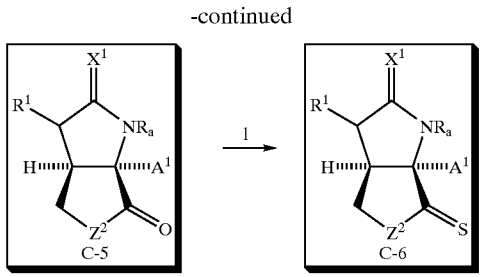

a) (BNOCH$_2$)$_2$CuLi; acidic water b) See also Scheme 1 for cases in which A$^1$ is H.
c) HCl, HS(CH$_2$)$_3$SH, CF$_3$CH$_2$OH d) See Scheme 8 e) H$_2$, Pd/C f) TsCl, pyridine
g) Nucleophile corresponding to Z$^2$ h) Protection of Z$^2$, if necessary i) See Schemes 8 and 9 j) deprotection of Z$^2$, if necessary k) DCC l) Lawesson's reagent

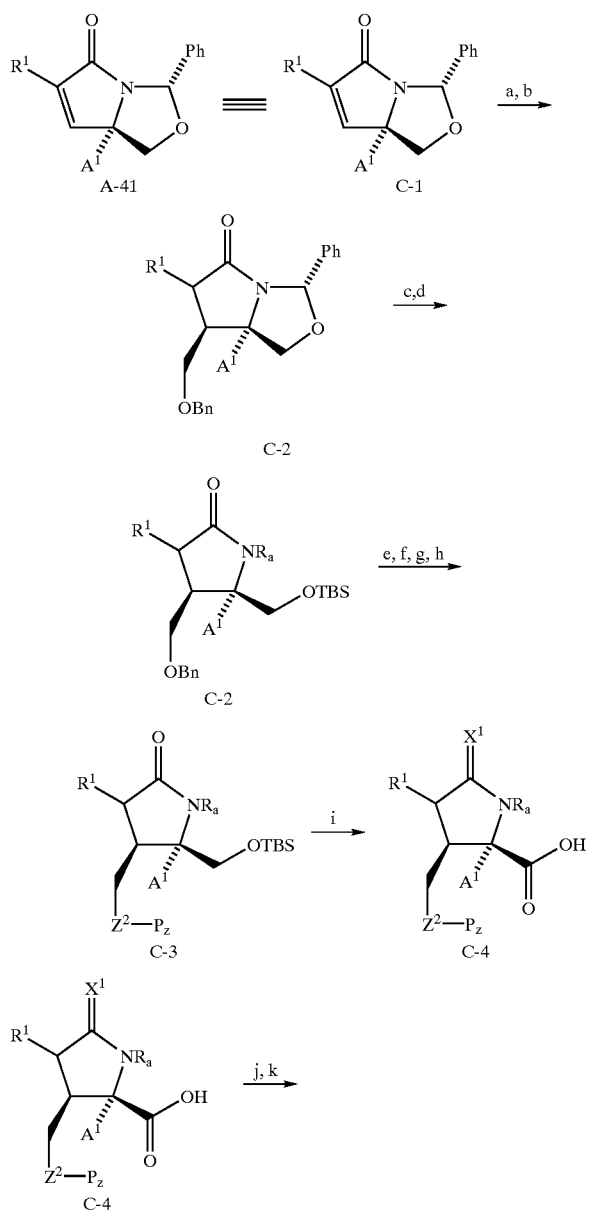

necessary, followed by cyclization with, for example, DCC, yields bicyclic structures C-5 which if desired are sulfurized with Lawesson's reagent [Cava, M. P., et al., (1985)] to give C-6.

The preparation of the compounds covered by the right-hand structure in claim 7 relies on a key intermediate from Scheme 9. As shown in Scheme 22, compound C-11 is analogous to a subset, defined by Z$^7$, of the class of compounds A-52, whose preparation is illustrated in Schemes 1–8, and described in the accompanying text. Deprotection of the primary hydroxyl with, for example, TBAF in THF and oxidation via, for example, under Swern oxidation conditions to the aldehydes C-12. Homologation of the aldehyde with, for example, the phosphorous ylide derived from triphenylmethoxymethylphosphonium chloride [Jamison, T. F., et al., *J. Am. Chem. Soc.*, (1994) 116:5505] yields enolethers of the type C-13, which are converted to carboxylic acids C-14 with acidic hydrolysis and oxidation of the resulting aldehyde with, for example, buffered NaClO$_2$ oxidation. [Corey, E. J., et al., (1992a)].

Deprotection of Z$^7$, if necessary, followed by cyclization with, for example, DCC, [Klausner, Y. S., et al., *Synthesis* (1972) 453] yields bicyclic structures C-15 which if desired are sulfurized with Lawesson's reagent [Cava, M. P., (1985)] to give C-16.

The preparation of the compounds covered by claims 8 and 21 relies primarily on the boron-enolate mediated asymmetric aldol procedures of Evans [Evans, D. A., et al., *J. Am. Chem. Soc.*, (1981) 103:2127] and on the results of studies on intramolecular radical cyclizations. [Curran, D. P., *Comprehensive Organic Synthesis*, (1991) 4:779–831].

Esters C-21 (Scheme 23), prepared by standard methods, are deprotonated and then alkylated with benzyloxy- Scheme 22
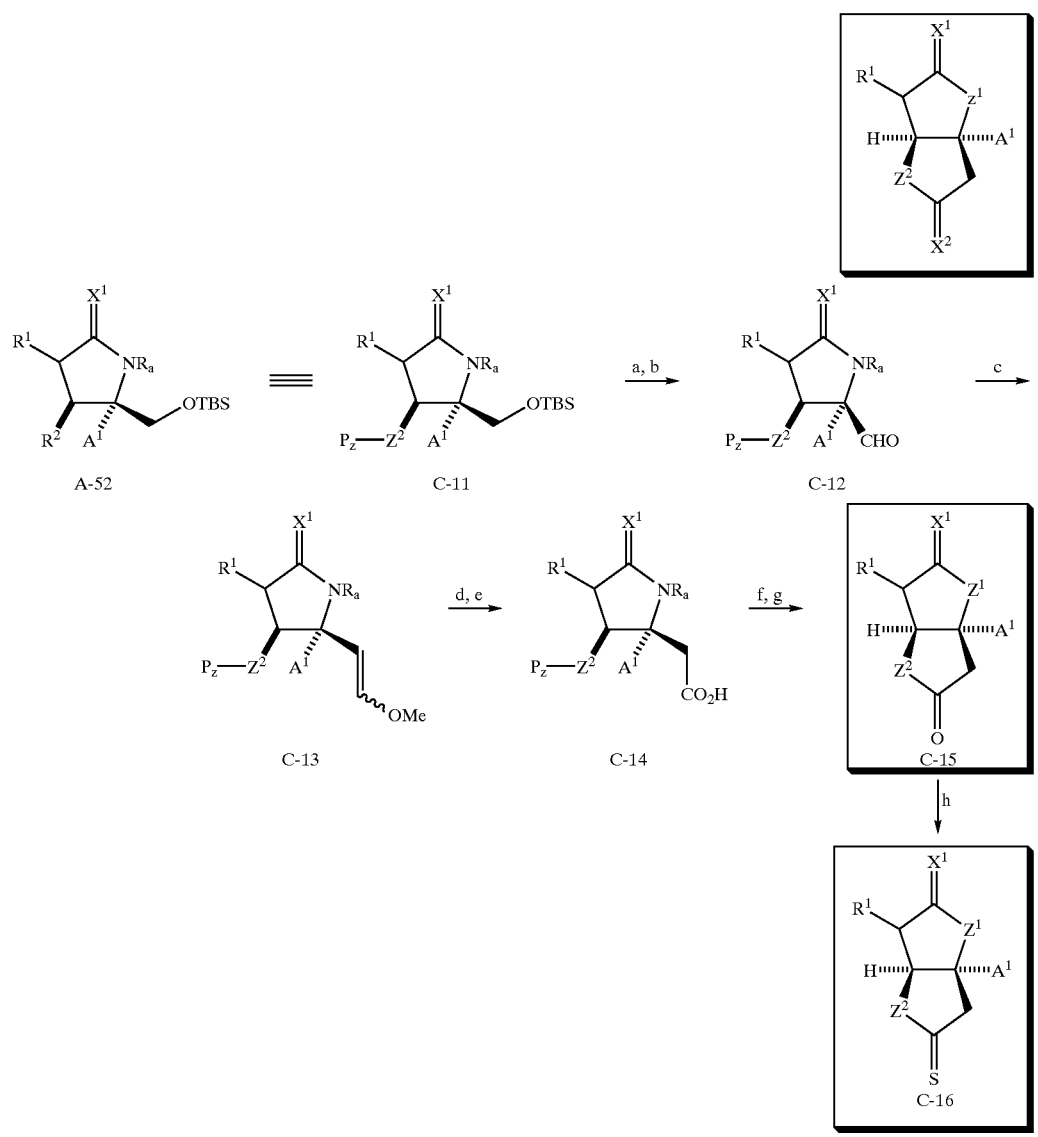
a) TBAF, THF b) Swern oxidation c) Ph₃P═C(H)(OCH)₃
d) HCl, H₂O, THF e) NaClO₂, NaH₂PO₄ f) remove P$_z$, if necessary
g) DCC h) Lawesson's reagent
Scheme 23
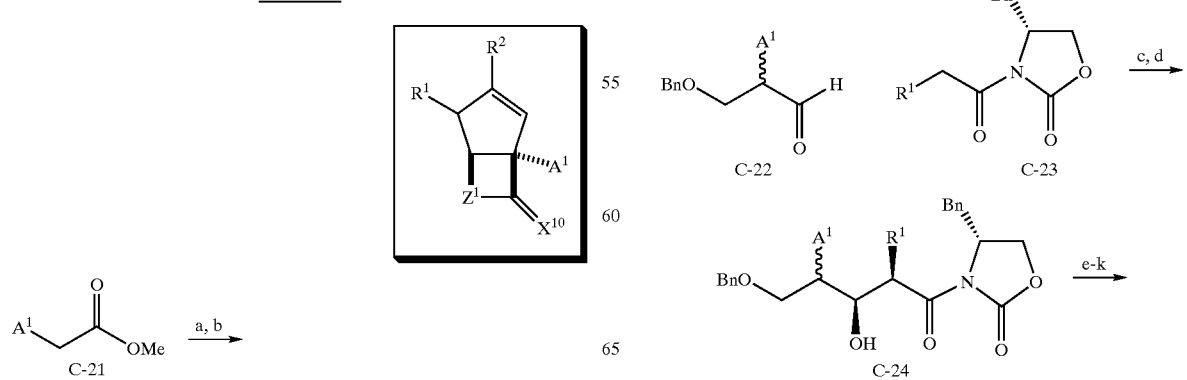

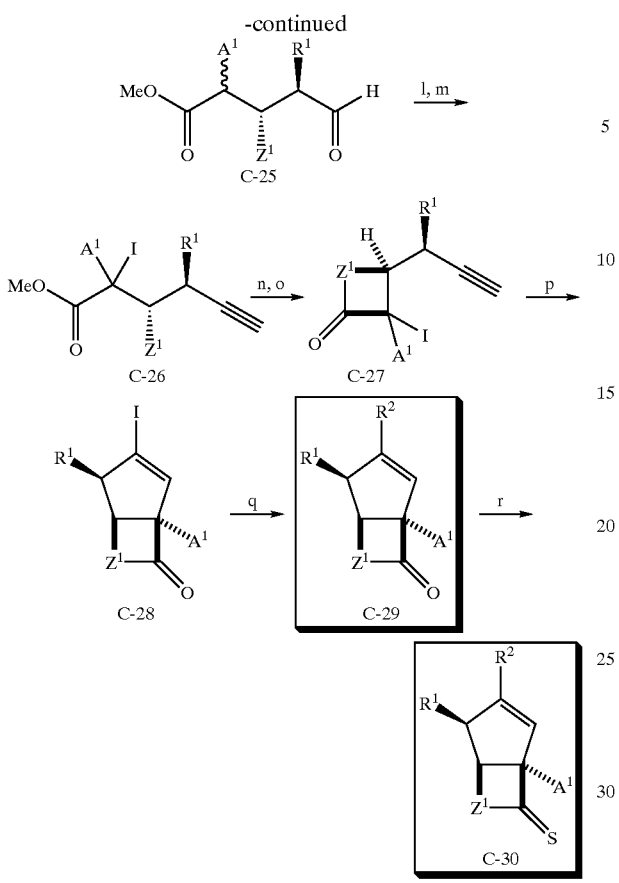

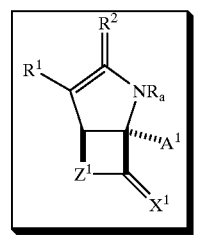

Scheme 24

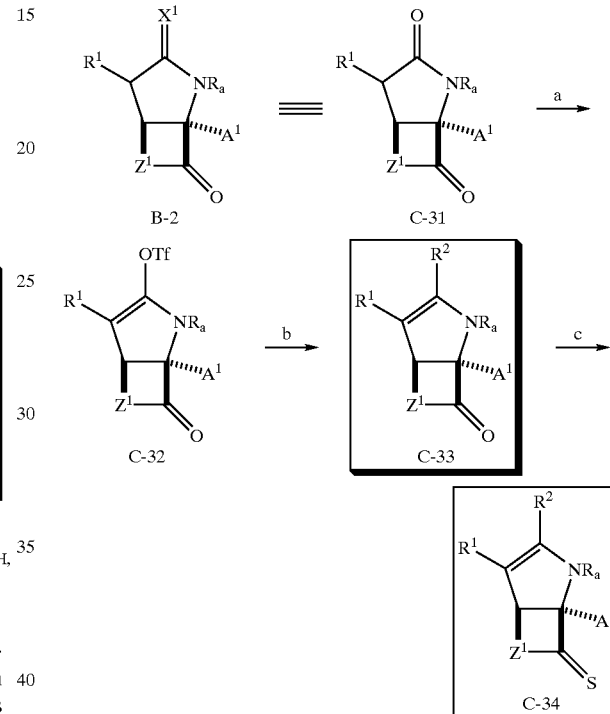

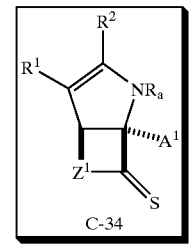

a) LDA; BnOCH$_2$Br b) DIBAL-H c) Bu$_2$BOTf, Et$_3$N d) C-22 e) TsCl, pyridine f) Nucleophile corresponding to Z$^1$ g) H$_2$, Pd/C h) Swern oxidation i) NaClO$_2$, NaH$_2$PO$_4$ j) CH$_2$N$_2$ k) LiAlH$_4$; Swern oxidation l) Base, Gilbert reagent m) LDA; TMS-Cl; I$_2$ n) LiOH, THF, water o) BOP-Cl p) (Bu$_3$Sn)$_2$, hν q) (Ph$_3$P)$_4$Pd, R$^2$-M r) Lawesson's reagent bromomethane and reduced with DIBAL-H to give aldehydes C-22 as a racemic mixture. Addition of C-22 to an boron enolate derived from chiral oxazolidinone imides C-23 [Evans, D. A., et al., (1981)] yields C-24 as a mixture of A$^3$ diastereomers. The configurational identity of the other two new stereocenters is established in this reaction and is not affected by the configuration of A$^3$.

Conversion to aldehydes C-25 in a six-step procedure (for example, tosylation of the secondary hydroxyl, displacement with a nucleophile corresponding to Z$^7$, catalytic hydrogenolysis of the benzyl group, oxidation of the alcohol to the carboxylic acid and esterification) allows for preparation of the substrate for the intramolecular radical cycloaddition. Thus, treatment of the aldehyde with the Gilbert reagent [Gilbert, J. C., et al., *J. Org. Chem.* (1982) 47:1837] and replacement of the enolizable hydrogen with iodine gives an acetylenes C-26, which, after deprotection of Z$^7$, if necessary, and cyclization with, for example, BOP-Cl, affords C-27.

Exposure of C-27 to atom-transfer, intramolecular radical cyclization conditions [Curran, D. P., et al., *Tet. Lett.* (1987) 28:2477 and Curran, D. P., et al., *J. Org. Chem.* (1989) 54:3140] gives compounds C-28. This reaction deserves further comment. The stereochemistry of A$^1$ and the iodine atom are inconsequential because the radical generated from the iodine can interconvert under the reaction conditions. Further, only one of the radical diastereomers will be able to cyclize—that giving the cis-4,5 ring system depicted, because the trans-4,5 suffers from much greater ring strain.

This cyclization is favored for two other reasons. First, it is a 5-endo-dig type cyclization and therefore favored according to Baldwin's rules for cyclization.

a) LiHMDS; PhN(Tf)$_2$ b) (Ph$_3$P)$_4$Pd, LiCl, R$^2$-M c) Lawesson's reagent

[Baldwin, J. E., *J. Chem. Soc., Chem. Commun.* (1976) 734]. Second, the atom transfer conditions used are ideal because the resulting vinylic radical is very reactive and is rapidly quenched by the iodine radical. [Curran, D. P., et al., *J. Am. Chem. Soc.*, (1986) 108:2489].

Elaboration of C-28 to C-29 is accomplished using, for example, standard Stille [Stille, J. K., *Angew. Chem., Int. Ed. Engl.* (1986) 25:504] or Heck [Heck, R. F., *Comprehensive Organic Synthesis*, (1991) 4:833–863] type coupling conditions using a suitable metallic derivative (M is, e.g., tributylstannyl) of R$^9$. Sulfurization with Lawesson's reagent [Cava, M. P., et al., (1985)] gives compounds C-30, thus completing the preparation of all the compounds claimed in claims 8 and 21.

The preparation of the compounds covered by claims 9 and 22 relies primarily on intermediate B-2, whose preparation is described in Schemes 13a, 13b and 14 and discussed in the accompanying text. As shown in Scheme 24, C-31 is deprotonated with a suitable base, and the resulting enolate is treated with, for example, the triflate source PhN(Tf)$_2$ [McMurry, J. E., et al., *Tet. Lett.* (1983) 24:979]. The vinyl triflates C-32 are treated with, for example, a catalytic amount of (Ph$_3$P)$_4$Pd and a suitable metallic derivative [Stille, J. K. (1986) and Heck, R. F. (1991)] (M is, e.g., tributylstannyl) of R$^9$, giving analogues C-33, which can be treated with Lawesson's reagent [Cava, M. P., et al., (1985)]

gives compounds C-34, thus completing the preparation of all the compounds in this section.

The preparation of the compounds covered by claims 10 and 23 relies primarily on intermediate A-38, whose preparation is illustrated in Schemes 1, 5, and 6, and discussed in the accompanying text. Compounds of the type C-41 (Scheme 25) can therefore be prepared with either the The preparation of the compounds covered by claims 11 and 24 follows the strategy illustrated in Schemes 1, 3, 4, 5, 8, and 9, and described in the accompanying text. Thus, as shown in Scheme 26, C-51, being analogous to A-2 is elaborated to C-52 following the same methods used in Scheme 1 using an aldehyde containing $A^5$ and a protected form of $Z^7$ in either the (R) or (S) configuration. Protection

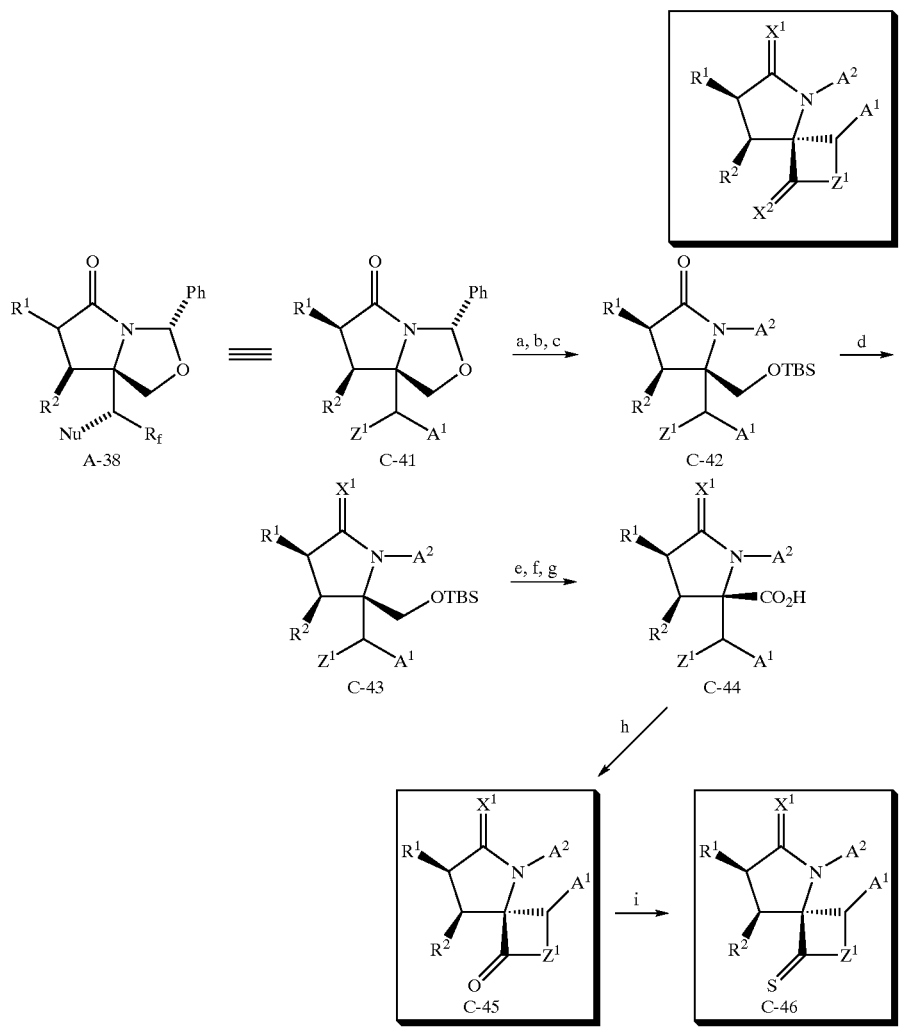

a) HCl, HS(CH$_2$)$_3$SH, CF$_3$CH$_2$OH b)TBS-Cl, imidazole,DMF c) base; electrophile corresponding to $A^2$ d) See scheme 8 e) TBAF, THF f) Swern Oxidation g) NaClO$_2$, NaH$_2$PO$_4$ h) BOP-Cl i) Lawesson's reagent (R) or (S) configuration of $Z^7$ by following the procedures illustrated in Schemes 1–6, and discussed in the accompanying text.

Mild acidic hydrolysis of C-41, [Corey, E. J., et al., (1992a)] followed by protection of the primary hydroxyl [Corey, E. J., et al., (1972)] allows for installation of $A^4$ via standard alkylation procedures, [Challis, N. (1970)] giving C-42. Elaboration of these intermediates to C-43 is performed as described for the analogous compounds in Scheme 8. Deprotection of the primary hydroxyl allows for oxidation to the carboxylic acids C-44, which are cyclized with, for example, BOP-Cl, giving analogues C-45, which can be treated with Lawesson's reagent [Cava, M. P., et al., (1985)] gives compounds C-46, thus completing the preparation of all the compounds in claims 10 and 23.

of the secondary hydroxyl gives compounds C-52, [Corey, E. J., et al., (1972)] which can be treated with a nucleophile corresponding to $R^9$ and subsequent quenching with acidic water, giving C-53. The reasons governing the indicated stereoselectivity of the nucleophilic addition and aqueous quenching have been discussed in the text accompanying Scheme 1.

Deprotection and subsequent conversion of the secondary hydroxyl to the tosylate allows for introduction of $A^3$ via displacement of the tosylate with a nucleophile corresponding to $A^3$ to give compounds of the type C-54.

Scheme 26

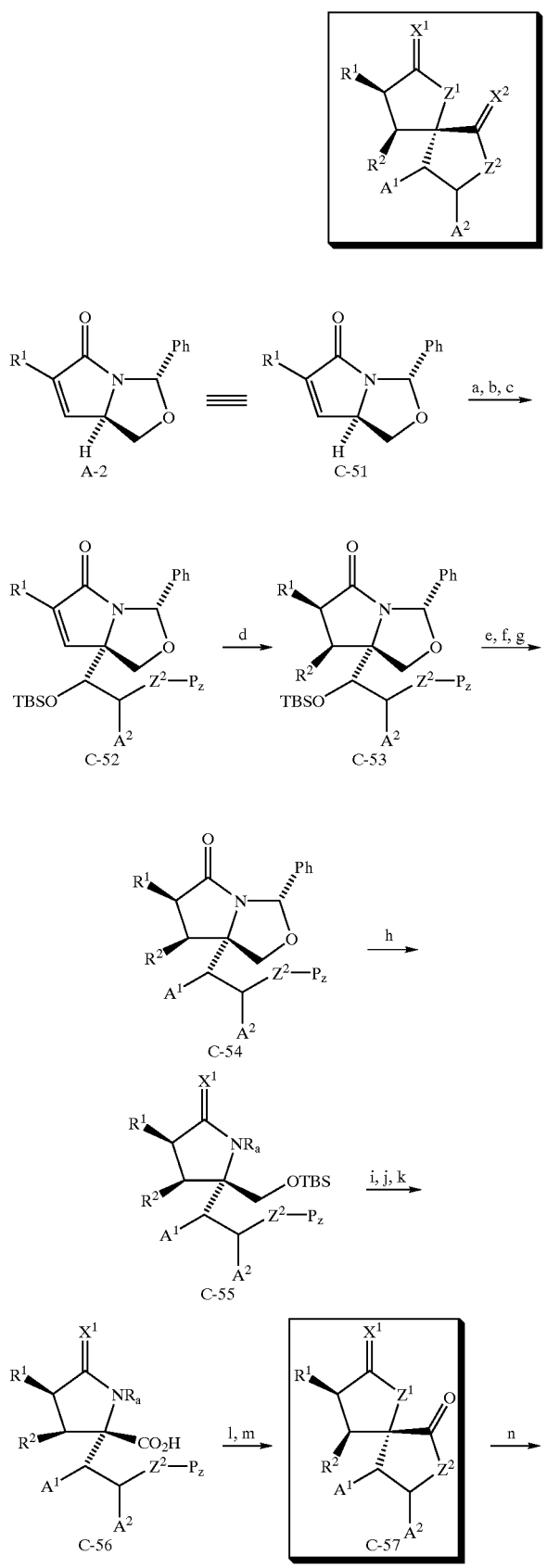

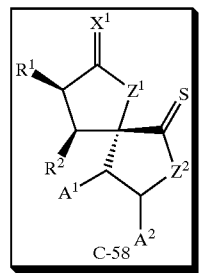

a) TBS-OTf, 2,6-lutidine b) [(A²)(Z²-P_z)]CHCHO, SnCl₄, Et₂O c) TBS-Cl, imidazole, DMF d) Nucleophile corresponding to R²; acidic water e) TBAF, THF f) TsCl, pyridine g) Nucleophile corresponding to A¹ h) See Scheme 8 i) TBAF, THF j) Swern oxidation k) NaClO₂, NaH₂PO₄ l) deprotect Z², if necessary m) DCC n) Lawesson's reagent

[Hanessian, S., (1980)]. Elaboration of these compounds to C-55 is performed with the methods illustrated in Scheme 8 and described in the accompanying text. Deprotection of the primary hydroxyl allows for oxidation to the carboxylic acids C-56, which are cyclized with, for example, DCC, [Klausner, Y. S., et al., (1972)] following deprotection of $Z^7$, if necessary, to give analogues C-57. Sulfurization with Lawesson's reagent [Cava, M. P., (1985)] gives compounds C-58, thus completing the preparation of all the compounds in 11 and 24.

The preparation of the compounds covered by claim 12 and 25 relies primarily on the results of Lubell, et al., *J. Org. Chem.*, 1990 55:3511. Thus, as shown in Scheme 27, L-serine (C-61) is converted to ketones C-62 by known procedures. (PhFl is an abbreviation of 9-phenyl-9-fluorenyl.) Standard Wadsworth-Emmons olefination of C-62 yields either C-63 or C-64, or a mixture thereof. The composition of the product mixture is of no consequence, since both olefin isomers yield the same diastereomer in the next reaction.

Thus, a cuprate reagent derived from $A^1$ approaches from the back face of both C-63 or C-64 since the very bulky PhFl group blocks the other face completely, giving C-65 as the major diastereomer. C-65 is converted to C-66 in a five-step procedure (reduction of the methyl ester to the aldehyde and protection as the dimethyl acetal, deprotection of the oxazolidinone, and oxidation of the primary alcohol to the carboxylic acid.)

As depicted in Scheme 28, DCC-mediated coupling, for example, of C-66 with an amine, yields amides C-67. Taken together, C-66 and C-67 comprise the general class of compounds C-88. The PhFl group is removed by catalytic hydrogenolysis, and the free amine alkylated with an Scheme 27
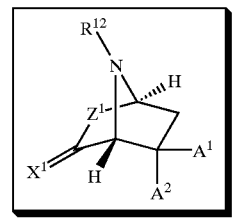
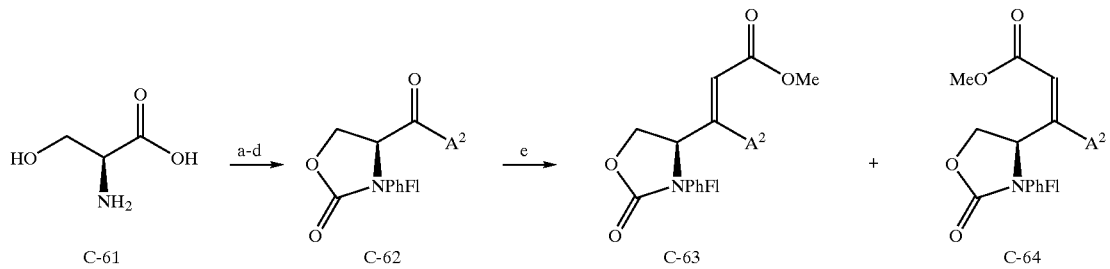
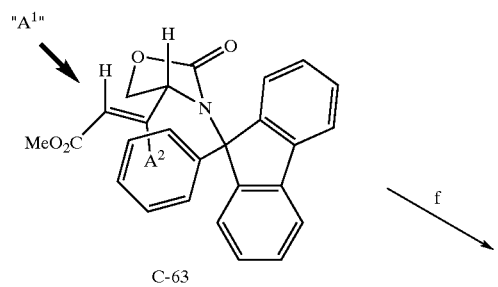
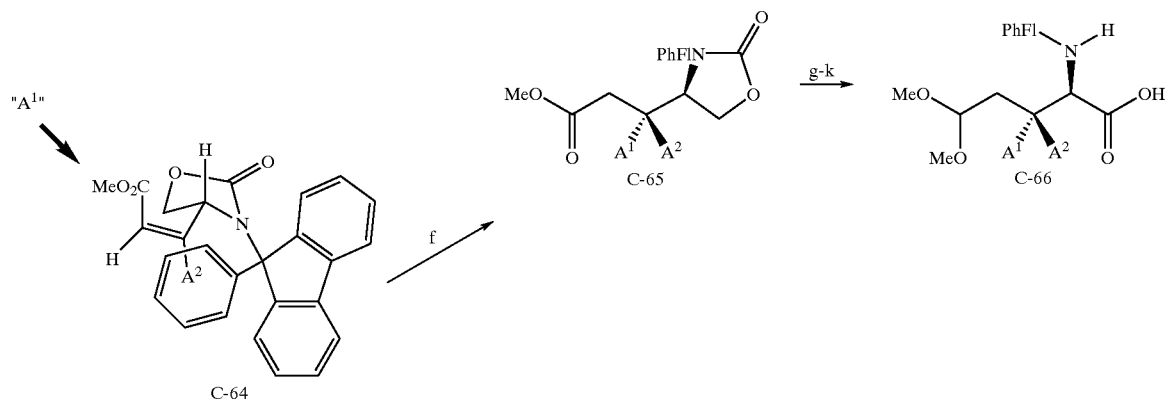
a-c) See Lubell, et. al. d) $A^2$MgBr, THF; acidic water e) (MeO)$_2$PCH$_2$CO$_2$Me, NaH
f) ($A^1$)$_2$CuLi g) DIBAL-H h) MeOH, TsOH i) KOH, EtOH, reflux j) Swern oxidation
k) NaClO$_2$, NaH$_2$PO$_4$

Scheme 28

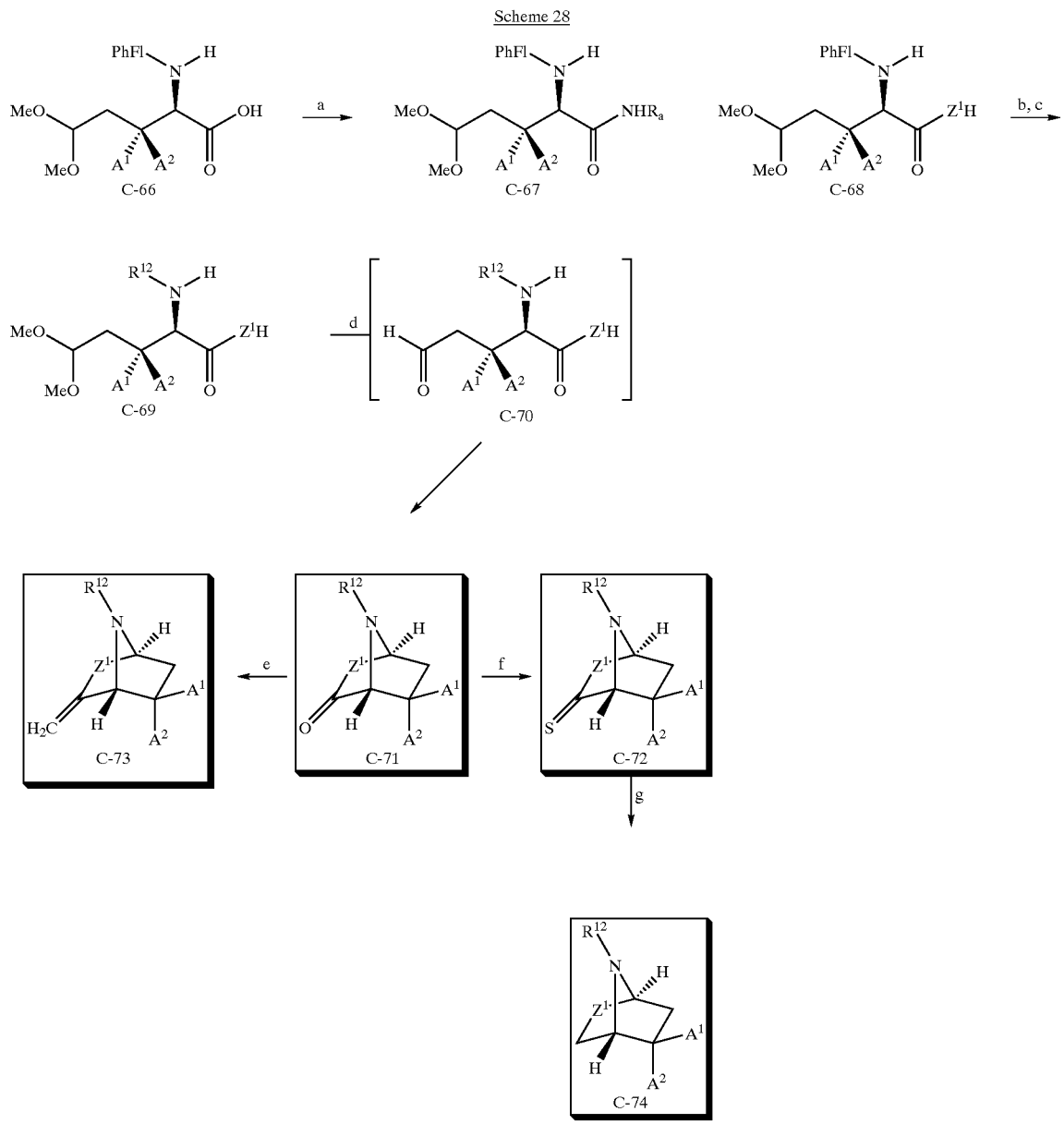

a) $H_2NR_a$, DCC b) $H_2$ Pd/C c) base, electrophile corresponding to $R^{12}$ d) TsOH, acetone e) Tebbe olefination f) Lawesson's reagent g) Raney Ni electrophile corresponding to $R^{12}$ (reductive amination with an or ketone and $NaCNBH_3$ is another option) to give compounds C-69. Acidic hydrolysis of the dimethyl acetal yields intermediate aldehyde C-70, which cyclizes to analogues C-73.

Tebbe olefination of C-71 provides compounds C-73. Treatment of C-71 with Lawesson's reagent provides compounds C-72, which can be desulfurized with Raney Nickel to give compounds C-74, thus completing the synthesis of all the compounds in claims 12 and 25.

The preparation of the compounds covered by claims 13 and 26 relies primarily on the results of Dener, et al., *J. Org. Chem.*, 1993, 58:1159, and on those of Evans et al., *J. Am. Chem. Soc.*, 1981, 103:2127. Thus, as shown in Scheme 29, D-aspartic acid (C-81) is protected and alkylated with an electrophile corresponding to $A^6$ to give compounds C-82, with the major diastereomer to be that shown. Dener et al., *J. Org. Chem.*, 1993, 58:1159. (PhFl is an abbreviation of 9-phenyl-9-fluorenyl.) Site-specific DIBAL-H reduction (owing to the extreme size of the PhFl group) affords aldehyde C-83.

A diastereoselective boron-mediated aldol addition is the next step. Following the procedure of Evans, et al., *J. Am. Chem. Soc.*, (1981) 103:2127, one obtains C-85, after TBS protection of the secondary hydroxyl. The oxazolidinone is removed with lithium hydroperoxide, the PhFl group removed with catalytic hydrogenolysis, and lactam formation accomplished under, for example, DCC conditions, to give C-86. Removal of the TBS group with TBAF and lactone formation (Saponificaiton of the methyl ester with LiOH, followed by DCC coupling may be necessary.) yields C-87, which is elaborated to C-88 by alkylating the amide nitrogen with a nucleophile corresponding to $R_d$. Epimerization with

Scheme 29

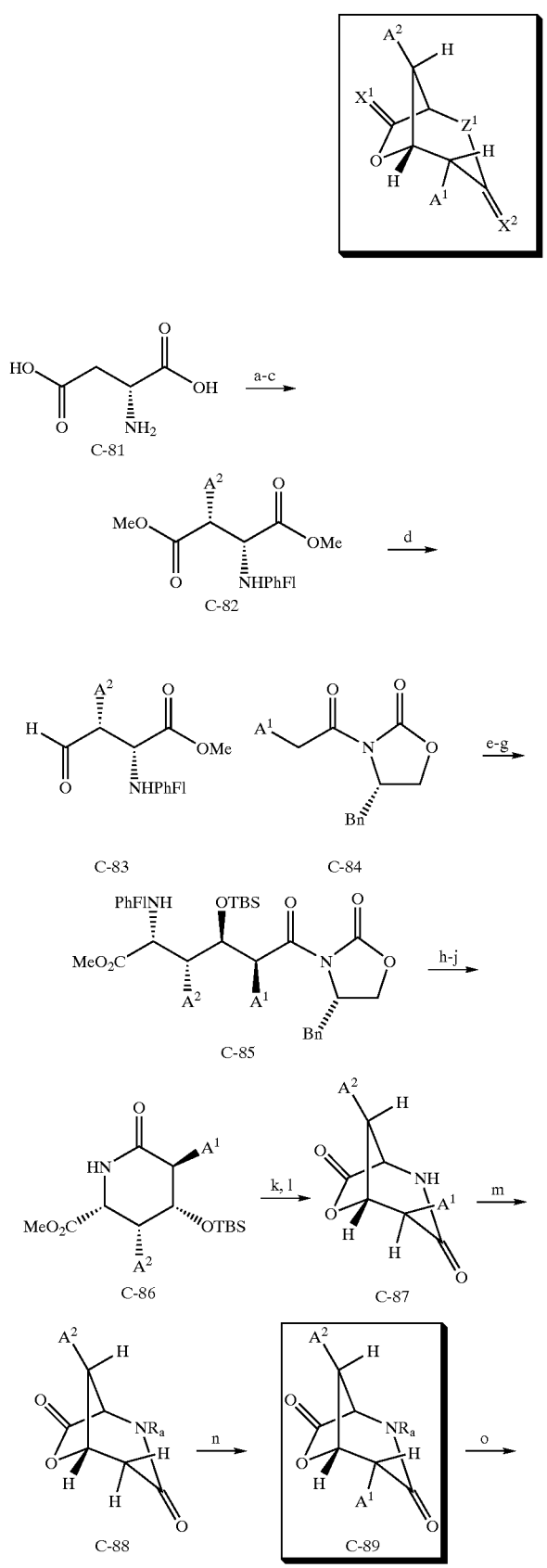

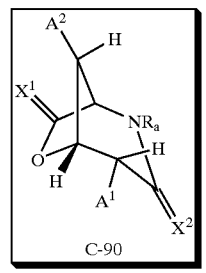

a-c) See Dener, et. al. d) DIBAL-H e) Bu₂OTf f) C-83 g) TBS-Cl, imidazole, DMF h) LiOOH, THF, H₂O i) H₂, Pd/C j) DCC k) TBAF, THF l) cyclize m) base, electrophile corresponding to $R_a$ n) DBU o) Lawesson's reagent DBU provides access to compounds C-89. Treatment of C-89 with Lawesson's reagent, Cava et al., *Tetrahedron*, 1985, 41: 5061, yields compounds C-90, thus completing the preparation of all compounds in this section.

Use

The disclosed compounds are used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB. Treating as used herein includes reversing, reducing, or arresting the symptoms, clinical signs, and underlying pathology of a condition in manner to improve or stabilize the subject's condition.

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa–32 kDa). The 25 kDa subunit has an N-terminal sequence of X-Gln-Asn-Pro-Met-X-Thr-Gly-Thr-Ser, which is identical to the β-subunit of human macropain. Kojima, S. et al., *Fed. Eur. Biochem. Soc.*, (1992) 304:57–60. The APP-processing enzyme cleaves at the Gln[15]-Lys[16] bond; in the presence of calcium ion, the enzyme also cleaves at the Met[1]-Asp[1] bond, and the Asp[1]-Ala2 bonds to release the extracellular domain of β-AP.

One embodiment, therefore, is a method of treating Alzheimer's disease, including administering to a subject an effective amount of a compound (e.g., pharmaceutical composition) having a formula disclosed herein. Such treatment includes reducing the rate of β-AP processing, reducing the rate of β-AP plaque formation, and reducing the rate of β-AP generation, and reducing the clinical signs of Alzheimer's disease.

Other embodiments of the invention relate to cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Proteasome inhibitors are useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736 (1994). Embodiments of the invention therefore encompass methods for: reducing the rate of muscle protein degradation in a cell, reducing the rate of intracellular protein degradation, reducing the rate of degradation of p53 protein in a cell, and inhibiting the growth of p53-related cancers). Each of these methods includes the step of contacting a cell (in vivo or in vitro, e.g., a muscle in a subject) with an effective amount of a compound (e.g., pharmaceutical composition) of a formula disclosed herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50–p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes. Palombella et al., *Cell* (1994) 78:773–785. Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β. Palombella et al., (1994). Some embodiments of the invention include methods of affecting the level of expression of IL-2, MHC-I, IL-6, IFN-β or any of the other previously-mentioned proteins, each method including administering to a subject an effective amount of a compound of a formula disclosed herein.

NF-κB also participates in the expression of the cell adhesion genes that encode E-selectin, P-selectin, ICAm, and VCAM-1, Collins, T., *Lab. Invest.* (1993) 68:499–508. One embodiment of the invention is a method for inhibiting cell adhesion (e.g., cell adhesion mediated by E-selectin, P-selectin, ICAm, or VCAM-1), including contacting a cell with (or administering to a subject) an effective amount of a compound (e.g., pharmaceutical composition) having a formula disclosed herein.

NF-κB also binds specifically to the HIV-enhancer/promoter., When compared to the Nef of mac239, the HIV regulatory protein Nef of pbj14 differs by two amino acids in the region which controls protein kinase binding. It is believed that the protein kinase signals the phosphorylation of I-κB, triggering IκB degradation through the ubiquitin-proteasome pathway. After degradation, NF-κB is released into the nucleus, thus enhancing the transcription of HIV. Cohen, J., *Science*, (1995) 267:960. Two embodiments of the invention are a method for inhibiting or reducing HIV infection in a subject, and a method for decreasing the level of viral gene expression, each method including administering to the subject an effective amount of a compound of a formula disclosed herein.

Complexes including p50 are rapid mediators of acute inflammatory and immune responses. Thanos, D. and Maniatis, T., *Cell* (1995) 80:529–532. Intracellular proteolysis generates small peptides for presentation to T-lymphocytes to induce MHC class I-mediated immune responses. The immune system screens for autologous cells that are virally infected or have undergone oncogenic transformation. Two embodiments of the invention are a method for inhibiting antigen presentation in a cell, including exposing the cell to a compound of a formula described herein, and a method for suppressing the immune system of a subject (e.g., inhibiting transplant rejection), including administering to the subject an effective amount of a compound of a formula described herein.

Certain proteasome inhibitors block both degradation and processing of ubiquitinated NF-κB in vitro and in vivo. Proteasome inhibitors also block IκB-α degradation and NF-κB activation, Palombella, et al.; and Traenckner, et al., *EMBO J.* (1994) 13:5433–5441. One embodiment of the invention is a method for inhibiting IκB-α degradation, including contacting the cell with a compound of a formula described herein. A further embodiment is a method for reducing the cellular content of NF-κB in a cell, muscle, organ, or subject, including contacting the cell, muscle, organ, or subject with a compound of a formula described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Other embodiments of the invention are methods for affecting cyclin-dependent eukaryotic cell cycles, including exposing a cell (in vitro or in vivo) to a compound of a formula disclosed herein. cyclins are proteins involved in cell cycle control. The proteasome participates in the degradation of cyclins. Examples of cyclins include mitotic cyclins, G1 cyclins, (cyclin B). Degradation of cyclins enables a cell to exit one cell cycle stage (e.g., mitosis) and enter another (e.g., division). It is believed all cyclins are associated with $p34^{cdc2}$ protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis. Ciechanover, A., *Cell*, (1994) 79:13–21. Inhibition of the proteasome inhibits cyclin degradation, and therefore inhibits cell proliferation (e.g., cyclin-related cancers). Kumatori et al., *Proc. Natl. Acad. Sci. USA* (1990) 87:7071–7075. One embodiment of the invention is a method for treating a proliferative disease in a subject (e.g., cancer, psoriasis, or restenosis), including administering to the subject an effective amount of a compound of a formula disclosed herein. The invention also encompasses a method for treating cyclin-related inflammation in a subject, including adminstering to a subject an effective amount of a compound of a formula described herein.

Additional embodiments are methods for affecting the proteasome-dependent regulation of oncoproteins and methods of treating or inhibiting cancer growth, each method including exposing a cell (in vivo, e.g., in a subject or in vitro) to a compound of a formula disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of a compound of a formula disclosed herein.

A tripeptide aldehyde protease inhibitor (benzyloxycarbonyl (Z)-Leu-Leu-leucinal induces neurite outgrowth in PC12 cells at an optimal concentration of 30 nM, Tsubuki et al., *Biochem. and Biophys. Res. Comm.* (1993) 196:1195–1201. Peptide aldehydes have been shown to inhibit the chymotryptic activity of the proteasome. Vinitsky, et al., 1992, Tsubuki et al., 1993. One embodiment of the invention is a method of promoting neurite outgrowth, including administering to the subject a compound of a formula disclosed herein.

Finally, the disclosed compounds are also useful as diagnostic agents (e.g., in diagnostic kits or for use in clinical laboratories) for screening for proteins (e.g., enzymes, transcription factors) processed by the proteasome. The disclosed compounds are also useful as research reagents for specifically binding the X/MB1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Lactacystin-can be used to determine whether a cellular, developmental, or physiological process or output is regulated by the proteolytic activity of the proteasome. One such method includes obtaining an organism, an intact cell preparation, or a cell extract; exposing the organism, cell preparation, or cell extract to a compound of a formula disclosed herein; exposing the compound-exposed organism, cell preparation, or cell extract to a signal, and monitoring the process or output. The high selectivity of the compounds disclosed herein permits rapid and accurate elimination or implication of the proteasome in a given cellular, developmental, or physiological process.

Formulation and Administration

The methods of the invention contemplate treatment of animal subjects, such as mammals (e.g., higher primates, and especially humans). The invention encompasses pharmaceutical compositions which include novel compounds described herein, and pharmaceutical compositions which include compounds described and first recognized herein as proteasome inhibitors, such as lactacystin.

Pharmaceutically acceptable salts may be formed, for example, with 1, 2, 3, or more equivalents of hydrogen chloride, hydrogen bromide, trifluoroacetic acid, and others known to those in the art of drug formulation. Compounds of the invention can be formulated into pharmaceutical compositions by admixture with pharmaceutically acceptable non-toxic excipients and carriers. A pharmaceutical composition of the invention may contain more than one compound of the invention, and/or may also contain other therapeutic compounds not encompassed by the invention, such as anti-inflammatory, anti-cancer, or other agents. A compound of the invention may be administered in unit dosage form, and may be prepared by any of the methods well known in the pharmaceutical art, for example, as described in Remington's Pharmaceutical Sciences (Mack Pub. Co., Easton, Pa., 1980). The invention also encompasses a packaged drug, containing a pharmaceutical composition formulated into individual dosages and printed instructions for self-administration.

Compounds disclosed herein as proteasome inhibitors may be prepared for use in parenteral administration, particularly in the form of solutions or liquid suspensions; for oral administrations, particularly in the form of tablets or capsules; or intranasally, particularly in the form of powders, gels, oily solutions, nasal drops, aerosols, or mists. Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention may be obtained, in part, by use of biocompatible, biodegradable polymers of lactide, and copolymers of lactide/glycolide or polyoxyethylene/polyoxypropylene. Additional parental delivery systems include ethylene-vinyl acetate copolymer particles, osmotic pumps, implantable infusion systems, and liposomes. Formulations for inhalation administration contain lactose, polyoxyethylene-9-lauryl ether, glycocholate, or deoxycholate. Formulations for buccal administration may include glycocholate; formulations for vaginal administration may include citric acid.

The concentration of a disclosed compound in a pharmaceutically acceptable mixture will vary depending on several factors, including the dosage of the compound to be administered, the pharmacokinetic characteristics of the compound(s) employed, and the route of administration. In general, the compounds of this invention may be provided in an aqueous physiological buffer solution containing about 0.1–10% w/v of compound for parenteral administration. Typical dose ranges are from about 0.1 to about 50 mg/kg of body weight per day, given in 1–4 divided doses. Each divided dose may contain the same or different compounds of the invention. The dosage will be an effective amount depending on several factors including the overall health of a patient, and the formulation and route of administration of the selected compound(s).

The effective amount of the active compound used to practice the present invention for treatment of conditions directly or indirectly mediated by the proteasome varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as "effective amount".

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever. All publications cited herein are hereby incorporated by reference.

Example 1

Synthesis of [$^3$H] Lactacystin

Lactacystin was prepared from the β-lactone, which was tritiated by an oxidation-reduction sequence. Unlabeled β-lactone was oxidized at C9 to the ketone with the Dess-Martin periodinane in dichloromethane and then reduced with [$^3$H]NaBH$_4$ (NEN, 13.5 Ci/mmol) in 1,2-dimethoxyethane/1% H$_2$O to afford tritiated β-lactone along with its C9-epimer (2:3 ratio). The isomeric β-lactones were separated by HPLC (Rainin Microsorb SiO$_2$ column, 4.6× 100 mm, 10% i—Pr—OH in hexane) and reacted separately with N-acetylcysteine (0.5 M) and Et$_3$N (1.5 N) in CH$_3$CN to afford the lactacystin (9S) and its C9-epimer (9R), which were purified from their respective reaction mixtures by reverse-phase HPLC(TSK ODS-80T$_m$ column, 4.6×250 mm, 10% CH$_3$CN/0. 1% CF$_3$CO$_2$H in H$_2$O).

Example 2

Fluorography of Crude Cell and Tissue Extracts

Crude Neuro 2A extracts (~11 μg total protein/lane) and crude bovine brain extracts (~54 μg total protein/lane) were treated as follows: (1) 10 μM [³H]lactacystin; (2) 10 μM [³H]lactacystin and 1 mM cold lactacystin; (3) 10 μM [³H]lactacystin; (4) 10 μM [³H]lactacystin and 1 mM cold lactacystin; (5) 10 μM [³H]lactacystin and 1 mM cold β-lactone; (6) 10 μM [³H]lactacystin and 1 mM cold phenylacetyl lactacystin; (7) 10 μM [³H]lactacystin and 1 mM cold lactacystin amide; (8) 10 μM [³H]lactacystin and 1 mM cold dihydroxy acid; (9) 10 μM [³H]lactacystin and 1 mM cold 6-deoxylactacystin; (10) 10 ;M [³H]lactacystin and 1 mM cold (6R,7S)-lactacystin (6-epi, 7-epi); (11) 10 μM [³H]lactacystin and 1 mM cold des(hydroxyisobutyl) lactacystin. Crude extracts from Neuro2A neuroblastoma cells or bovine brain were incubated in the presence of 10 μM [³H]lactacystin in the presence or absence of 1 mM cold competitor (added simultaneously) for 24 h at room temperature, followed by SDS-polyacrylamide gel electrophoresis (0.75-mm-thick 12% polyacrylamide gel). The gel was stained in 0.1% Coomassie brilliant blue R-250, 12% acetic acid, 50% MeOH, and then destained in 12% acetic acid, 50% MeOH, followed by impregnation with EN³HANCE (NEN) and precipitation of the fluor with water. The gel was dried on Whatman filter paper in a gel dryer at 65° C. for 30 min and then exposed to Kodak SB film at −78° C.

Example 3

Separation of Purified Protein Complex (20S proteasome)

Bovine brain was frozen in liquid $N_2$. A total of two kg of brain was dry homogenized in a Waring blender for one minute. All operations were performed at 4° C., except as noted. The following buffer (6 liters total) was then added (pH 7.7): 18.25 mM $K_2HPO_4$, 6.75 mM $KH_2PO_4$, 0.27 M sucrose, 2 mM EDTA, 2 mM EGTA, 25 mM NaF, 5 mM tetrasodium pyrophosphate, 5 μg/ml each of leupeptin and pepstatin A, and 5 mM β-mercaptoethanol. The tissue was wet homogenized in the Waring blender for two minutes. The homogenate was centrifuged at 5,000 g for 15 min and then at 12,000 g for 30 min. Ammonium sulfate was added to the supernatant to 50% saturation, and the sample spun at 10,000 g for 20 min. The 50–60% saturation ammonium sulfate fraction, containing the lactacystin-binding activity as determined by SDS-PAGE and fluorography of samples incubated with radioactive compound, was then dialyzed overnight against 20 mM MES-NaOH, pH 5.6, 5 mM β-mercaptoethanol, followed by SP-sepharose chromatography (Pharmacia SP-sepharose, fast flow; 120-ml bed volume column) with 20 mM MES-NaOH, pH 5.6, 5 mM fi-mercaptoethanol and an NaCl gradient from 0–0.3 M (500-ml gradient; flow rate=2 ml/min).

After pooling and diluting the relevant fractions, the pH was adjusted to 8 with 1 M Tris-HCl, pH 8. Q-sepharose chromatography (Pharmacia Q-sepharose, fast flow; 16-ml bed volume column) was performed with 20 mM Tris-HCl, pH 8, 5 mM β-mercaptoethanol and a NaCl gradient from 0–0.5 M (120-ml gradient; flow rate=1 ml/min). The relevant fractions were pooled, concentrated, and then applied to a Pharmacia Superose 6 gel filtration column (10 mM Tris-HCl, 1 mM EDTA, pH 8, 5 mM β-mercaptoethanol; flow rate=0.5 ml/min), with the lactacystin-binding activity corresponding to a single high molecular weight peak. This peak was isolated and treated with 10 μM [³H]lactacystin or 10 μM [³H]β-lactone for 24 h at 25° C. Trifluoroacetic acid (TFA) was added to 0.1%, and the sample was allowed to stand at room temperature for 20 min. Reverse-phase HPLC was then carried out at room temperature using a Vydac C4 column (300 Å/4.6×150 mm) with 20–40% acetonitrile/ 0.1% TFA over 10 min and then 40–55% acetonitrile/0.1% TFA over 30 min (flow rate=0.8 ml/min). An IN/US β-RAM in-line scintillation detector was used to monitor radioactivity.

The lactacystin-binding proteins were purified from bovine brain, and both were found to reside in the same high-molecular weight protein complex by gel-filtration chromatography. Treatment of the complex with [³H] lactacystin did not cause its dissociation, and the radioactivity uniquely comigrated with the complex. The molecular weight of the complex was estimated to be 700 kDa, and SDS-PAGE revealed that it consisted of numerous proteins with molecular weights of 24–32 kDa. Edman degradation of blotted protein revealed the sequences of several proteasome subunits in the ~24 kDa band, leading to a tentative identification of the complex as the 20S proteasome. After the complex was treated with [³H]lactacystin and subjected to reverse-phase HPLC to separate the proteasome subunits, eleven to twelve distinct peaks were resolved. However, the radioactivity was associated exclusively with the first two peaks, and predominantly with the second. These first two peaks were judged to be homogeneous by Coomassie blue staining of SDS-polyacrylamide gels and by sequencing of tryptic fragments, while some of the subsequently eluting, larger peaks were clearly not homogeneous. The ratio of counts incorporated into the first peak versus the second peak varied with the batch of protein, the length of incubation, and the ligand. The first peak is labeled more slowly, and the degree of labeling of the first peak relative to the second is greater with [3H]lactacystin than with the [³H]β-lactone at any given time. A one or two hour reaction with [³H]β-lactone results in only trace labeling of the first peak, while a 24 hour reaction with [³H]β-lactone or [³H] lactacystin results in significant labeling of this peak. The selectivity runs opposite to the relative chemical reactivity of the two compounds, and this finding suggests that the N-acetylcysteine moiety of lactacystin may facilitate recognition by this secondary protein. The first peak to elute from the reverse-phase HPLC column contained only a ~32 kDa protein, which corresponded to the 32 kDa secondary lactacystin-binding protein identified earlier.

Example 4

Amino Acid Sequence of Purified Bovine Lactacystin-binding Proteins

Purified 20S proteasome (purified as described in Example 3) was incubated for 24 h at room temperature with 10 μM lactacystin in 10 mM Tris-HCl, 1 mM EDTA (pH 8). The solution was then diluted tenfold with 20% aqueous acetonitrile containing 0.1% trifluoroacetic acid (TFA) and allowed to stand at room temperature for 5 min. Reverse-phase HPLC was then performed at room temperature using a Vydac C4 column (100 Å/4.6×150 mm) with 20–40% acetonitrile/0.1% TFA over ten minutes and then 40–55% acetonitrile/0.1% TFA over 30 min to elute the proteasome subunits (flow rate=0.8 ml/min). Peaks were collected based on ultraviolet light absorbance at 210 and 280 nm, with the primary lactacystin-modified protein being the second to elute off the column and the secondary lactacystin-binding protein being the first. Protein from repeated injections was pooled, lyophilized and subjected to Edman degradation following tryptic digestion and reverse-phase HPLC separation of tryptic fragments. The putative lactacystin-modified residue was identified by adding subunit X/MB1 isolated from [³H]lactacystin-treated proteasome to a sample that had been treated with unlabeled lactacystin, and then isolating and sequencing radioactive tryptic fragments. At one position, the phenylthiohydantoin-amino acid derivative was not identifiable, indicating possible modification of the residue.

Sequences from direct N-terminal sequencing and from tryptic fragments derived from the primary bovine lactacystin-binding protein aligned with sequences of human proteasome subunit X (predicted from the cDNA clone), and human IMP7-E2 (predicted from the exon 2-containing cDNA clone). Sequence 1 (from direct N-terminal sequencing) is also aligned with sequences of Saccharomyces cerevisiae Pre-2 (predicted from the genomic clone) and Thermoplasma acidophilum β-subunit (predicted from the cloned gene). The N-terminal heptapeptide corresponds to the tryptic fragment that appears to contain a lactacystin-modified N-terminal threonine residue. The threonine at this position also corresponds to the putative N-termini of the mature, processed forms of all the homologs listed. Upper-case letters denote high confidence sequence, while lower case letters indicate lower confidence assignments.

7.5, 1 mM EDTA was incubated at 25° C. in the presence of lactacystin or lactacystin analogs in DMSO or MeOH [not exceeding 5% (v/v)]. Aliquots for fluorescence assay were removed at various times following addition of compound and diluted in 10 mM Tris-HCl, pH 7.5, 1 mM EDTA containing fluorogenic peptide substrates (100 μM final). Suc-LLVY-AMC, Cbz-GGR-pNA and Cbz-LLE-pA (AMC=7-amido-4-methylcoumarin; PNA=β-naphthylamide) were used to assay for the chymotrypsin-like, trypsin-like and peptidylglutamyl-peptide hydrolyzing activities, respectively.

Biological activity of compound refers to the ability of the compound to induce neurite outgrowth in Neuro 2A neuroblastoma cells and to inhibit cell cycle progression in MG-63 osteosarcoma cells.

TABLE 1

DIRECT N-TERMINAL SEQUENCES

| | | |
|---|---|---|
| 1. Direct N-terminal sequence of primary bovine lactacystin-binding protein | TTTLAFKFRHggIIA | SEQ ID NO: 1 |
| Human subunit X/MB1 | 5 TTTLAFKFRHGVIVA 19 | SEQ ID NO: 2 |
| Human LMP7-E2 | 74 TTTLAFKFQHGVIAA 88 | SEQ ID NO: 3 |
| S. cerevisiae Pre-2 | 76 TTTLAFRFQGGIIVA 90 | SEQ ID NO: 4 |
| T. acidopholum β-subunit | 9 TTTVGITLKDAVIMA 23 | SEQ ID NO: 5 |
| 2. Primary bovine lactacystin-binding protein | DAYSGGSVSLY | SEQ ID NO: 6 |
| Human subunit X | 171 DAYSGGAVNLYHVR 184 | SEQ ID NO: 7 |
| Human LMP7-E2 | 239 DSYSGGVVNMYHMK 252 | SEQ ID NO: 8 |
| 3. Primary bovine lactacystin-binding protein | VIEINPYLLGTMAGGAADCSF | SEQ ID NO: 9 |
| Human subunit X | 38 VIEINPYLLGTLAGGAADCQFWER 61 | SEQ ID NO: 10 |
| Human LMP7-E2 | 106 VIEINPYLLGTMSGCAADCQYWER 129 | SEQ ID NO: 11 |
| 4. Primary bovine lactacystin-binding protein | GYSYDLEVEEAYDLAR | SEQ ID NO: 12 |
| Human subunit X | 146 GYSDLEVEQAYDLAR 161 | SEQ ID NO: 13 |
| Human LMP7-E2 | 214 GYRPNLSPEEAYDLGR 229 | SEQ ID NO: 14 |

Sequences of tryptic fragments derived from the secondary lactacystin-binding protein aligned with N-terminal fragment sequence of human erythrocyte proteasome a chain and of rat liver proteasome chain.

TABLE 2

TRYPTIC FRAGMENT SEQUENCES

| | | |
|---|---|---|
| Secondary bovine lactacystin-binding activity | TTIAGVVYK DGIVLGADTR | SEQ ID NO: 15 |
| Human erythrocyte proteasome α chain | 1 XXIAGVVYK DGIVLGADTR 19 | SEQ ID NO: 16 |
| Rat liver proteasome chain 1 | 1 TTIAGVVYK DGI 12 | SEQ ID NO: 17 |

Sequence analysis of tryptic fragments derived from this protein showed it to be homologous to the proteasome a chain, a ~30 kDa protein identified in purified human erythrocyte proteasome and rat liver proteasome for which only an N-terminal fragment sequence exists. The second peak to elute contained only a ~24 kDa protein, the primary lactacystin-binding protein. Sequence from the N-terminus of the protein and from derived tryptic fragments showed high identity to the recently discovered 20S proteasome subunit X, also known as MB1, a homolog of the major histocompatibility complex (MHC)-encoded LMP7 proteasome subunit.

Example 5

Kinetics of Inhibition of 20S Proteasome Peptidase Activities

Experiments involving the proteasome were performed as follows: 20S proteasome (~5 ng/μl) in 10 mM Tris-HCl, pH

TABLE 3

Kinetics of Inhibition $K_{assoc} = K_{obs}/[I]\ (s^{-1}M^{-1})$

| Compound (concentration) | Biological activity of compound | Chymotrypsin-like activity (Suc-LLVY-AMC) | Trypsin-like activity (Cbz-GGR-βNA) | Peptidyl-glutamyl-peptide hydrolyzing activity (Cbz-LLE-βNA) |
|---|---|---|---|---|
| Lactacystin (10 μM) | + | 194 ± 15 | 10.1 ± 1.8 | |
| Lactacystin (100 μM) | + | | | 4.2 ± 0.6 |
| β-Lactone (1 μM) | + | 3059 ± 478 | | |
| β-Lactone (5 μM) | + | | 208 ± 21 | |
| β-Lactone (50 μM) | + | | | 59 ± 17 |
| Dihydroxy acid (100 μM) | – | No inhibition | No inhibition | No inhibition |
| Lactacystin amide (12.5 μM) | + | 306 ± 99 | | |
| Phenylacetyl lactacystin (12.5 μM) | + | 179 ± 19 | | |
| 6-Deoxylact-acystin (12.5 μM) | – | No inhibition | | |

TABLE 3-continued

Kinetics of Inhibition $$\text{K}_{assoc} = \text{K}_{obs}/[\text{I}] \ (\text{s}^{-1}\text{M}^{-1})$$

| Compound (concentration) | Biological activity of compound | Chymotrypsin-like activity (Suc-LLVY-AMC) | Trypsin-like activity (Cbz-GGR-βNA) | Peptidyl-glutamyl-peptide hydrolyzing activity (Cbz-LLE-βNA) |
|---|---|---|---|---|
| (6R,7S) Lactacystin (6-epi,7-epi) (12.5 μM) | – | No inhibition | | |
| Des(hydroxy-isobutyl)-lactacystin (12.5 μM) | – | No inhibition | | |

Example 6

Selectivity of Protease Inhibition

Experiments involving the other proteases were similar to Example 5, except that buffers used for incubation with lactacystin were as follows: β-Chymotrypsin: 10 mM Tris-HCL, pH 8, 1 mM EDTA (plus 100 μM Suc-LLVY-AMC for fluorescence assay); Trypsin: 10 mM Tris-HCL, pH 8, 20 mM $CaCl_2$ (plus 100 μM Cbz-GGR-PNA for assay); Calpain I: 20 mM Tris-HCL, pH 8, 1 mM $CaCl_2$, 1 mM DTT (plus 100 FM Suc-LLVY-AMC for assay); Calpain II: 20 mM Tris-HCL, pH 8, 10 mM $CaCl_{21}$ 1 mM DTT (plus 100 μM Suc-LLVY-AMC for assay); Papain: 50 mM MES-NaOH, pH 6.4, 1 mM DTT (plus 100 μM Cbz-RR-AMC for assay); Cathepsin B: 100 mM $KH_2PO_4$, pH 5.5, 2 mM EDTA, 1 mM DTT (plus 100 μM Cbz-RR-AMC for assay). Fluorescent emission at 460 nm with excitation at 380 nm was measured for AMC-containing substrates, and emission at 410 nm with excitation at 335 nm was measured for βNA-containing substrates. The fluorescence assays were conducted at 25° C., each experiment was performed at least three times, and values represent mean±standard deviation.

TABLE 4

Inhibition of Other Proteases

| Protease tested | Effect of lactacystin (100 μM) |
|---|---|
| α-Chymotrypsin | No inhibition |
| Trypsin | No inhibition |
| Calpain I | No inhibition |
| Calpain II | No inhibition |
| Papain | No inhibition |
| Cathepsin B | No inhibition |

The effects of lactacystin and the β-lactone on proteasame peptitase on activities using fluorogenic peptide substrates were assessed. All three peptidase activities were inhibited, irreversibly in the case of the trypsin-like and chymotrypsin-like activities and reversibly in the case of the PGPH activity. The apparent second-order rate constant for association of each inhibitor with the enzyme, $k_{assoc}$, was determined for each of the activities (Table 1A). Lactacystin inhibits the chymotrypsin-like activity the fastest ($k_{assoc}$= 194±15 $M-1_s$-1), the trypsin-like activity 20-fold more slowly, and the PGPH activity 50-fold more slowly. The fact that the inhibition kinetics are different for the three activities lends further support to the notion that the activities are due to separate active sites. The β-lactone displays the same rank order but inhibits each activity 15–20 times faster than does lactacystin itself, in accord with the greater expected chemical reactivity of the β-lactone. It is also possible that, upon initial binding to the protein target, the lactacystin thioester is cyclized in a rate-limiting step to the β-lactone, which serves as an activated intermediate for attack by the nucleophile.

The reversibility of the inhibitory effects was assessed by measuring residual peptidase activity after removal of excess inhibitor by extensive serial dilution/ultrafiltration. The trypsin-like and chymotrypsin-like activities were still completely inhibited in the lactacystin-treated samples following dilution/ultrafiltration, implying very low $k_{off}$ of inhibitor from enzyme, whereas controls untreated with inhibitor maintained activity (data not shown). In the case of the PGPH activity, removal of the inhibitor was accompanied by a return of the catalytic activity; inhibition of the PGPH activity could be due to non-covalent association of lactacystin with the PGPH site or covalent association with turnover.

Previously, we had shown that the ability of analogs to cause neurite outgrowth in Neuro 2A cells was mirrored by their ability to inhibit cell-cycle progression in MG-63 osteosarcoma cells, and that modifications to the γ-lactam part of the molecule impared both activities whereas modifications of the N-acetylcysteine moiety had little effect [Fenteany, 1994 3135]. We therefore tested the ability of the analogs to inhibit the 20S proteasome, but as our supplies of these materials were insufficient to examine all three activities, we focused on the chymotrypsin-like activity, which is inhibited most rapidly by lactacystin. The same trends found in the biological studies were apparent: the biologically active compounds inhibited the chymotryptsin-like activity about as well as lactacystin itself, and the biologically inactive compounds did not inhibit this activity as all (Table 3). Modifications of the γ-lactam core of lactacystin mitigate its effect, but modifications of the N-acetylcysteine moiety do not.

Example 7

Assay of the Ability of Lactacystin (β-lactone form) can Block TNF-α Dependent Degradation of IκB-α in vivo Hela cells were plated onto 6-well plates in DME plus 10% fetal calf serum (3 mls/well). Cells were then pretreated with 0.125% DMSO 40 μM G132 (carbobenzoxyl-leucinyl-leucinyl-leucinal-H)(40 μM, lanes 103), or 5 μM β-lactone for one hour, followed by treatment with 1,000 U/ml TNF-α or phosphate buffered saline (PBS). Cells were harvested after 0 min, 20 min, or 40 min of further incubation at 37° C. Cells were then lysed in buffer containing NP-40 and protease inhibitors, and the proteins separated on a 10% SDS-polyacrylamide gel. The proteins were then transferred to nitrocellulose and probed with antibodies against the C-terminal 20 amino acids of human IκB-α.

Previous reports have shown that the inducible degradation of IκB is preceded by phosphorylation of the protein (Beg et al., 1993, Mol. Cell. Biol. 13:3301; Traenckner et al., 1994, EMBO J. 13:5433; Miyamoto et al., 1994, PNAS 91:12740; Lin et al., 1995, PNAS 92:552; DiDonato et al., 1995, Mol. Cell. Biol. 15:1302; and Alkalay et al., 1995, Mol. Cell. Biol. 15:1294). The phosphorylated IκB is then preferentially degraded, apparently by the proteasome (Palombella et al., 1994, Cell 78:773). Phosphorylation is evidenced by a slightly heavier shift in the electrophoretic mobility of IκB. IκB from cells induced with TNF show the requisite pattern of phosphorylation and degradation over time. Cells treated with PBS only show no change in the level or modification of IκB. As was reported previously, (Palombella et al, 1994), the peptide aldehyde proteasome inhibitor MG132 blocks the degradation of IκB and stabilizes the phosphorylated form. β-lactone also blocks degradation and stabilizes the phosphorylated form of IκB. These results indicate that lactacystin does not effect the TNF dependent signalling pathway that leads to the phosphorylation of IκB, but does block the degradation of the protein. Lactacystin inhibits the degradation of IκB after TNF induction of Hela cells, most likely by specifically blocking the action of the proteasome.

Example 8

Assay of the Effect of Lactacystin (β-lactone form) on the Proteasome Dependent p105 to p50 Processing in vivo COS cells were plated onto 100 mm dishes, then, with DEAE-Destran, either mock transfected, or transfected with 3 μg of pcDNA plasmid containing the human p105 CDNA. Forty-eight hrs after transfection, cells were pretreated for 1 hour with 0.5% DMSO, 50 μM calpain inhibitor II, 50 μM MG132, or 10 μM β-lactone. Cells were then pulse labelled with 250 uCi/plate of $^{35}$S-methionine/cysteine for 15 minutes, and either harvested immediately or followed by a 2 hour chase with excess unlabelled methionine and cysteine. Cells were then lysed with SDS/Tris, and proteins were immunoprecipitated with anti-p5o antibodies (recognize the N-terminal half of the p105 protein). These proteins were then separated on a 10% SDS-polyacrylamide gel, which was then fixed, dried, and exposed to autoradiographic film.

An analysis of the proteins isolated immediately after the pulse-labelling period reveals significant amounts of labelled p105 protein and very little p50. After the 2 hour chase period, the levels of p105 were reduced, and a new band that corresponds to p50 protein is apparent, as was expected (Fan and Maniatis, 1991, *Nature* 354:395; Palombella et al., 1994, *Cell* 78:773). Pretreatment of cells with calpain inhibitor II has no effect on the processing of p105 to p50 (lane 4). However, treatment of cells with the peptide aldehyde proteasome inhibitor MG132 completely blocks the appearance of p50 (lane 5), as has been reported previously (Palombella et al., 1994). Low levels of β-lactone (10 μM) have only a slight effect on the level of p50, but higher concentrations (50 μM) result in the complete inhibition of the processing of p105 to p50. Lactacystin efficiently blocks the proteasome dependent procession of p105 to p50 in vivo.

Example 9

Neurite Outgrowth Assay

Compounds are dissolved in the minimal amount of methanol (MeOH) or dimethyl sulfoxide (DMSO) required for solubilization. No more than 0.1% solvent is present in any assay. When necessary, solutions are evaporated to dryness and resuspended in cell culture medium to their final concentrations before use.

Neuro 2A, IMR-32, PC12, and MG-63 cells are obtained from the American Type Culture Collection. Neuro 2A and IMR-32 cells are cultured in Eagle's minimal essential medium (MEM) containing 10% (vol/vol) fetal bovine serum (FBS). PC12 cells are grown in RPMI 1640 medium containing 10% (vol/vol) horse serum and 5% FBS, and MG-63 cells are cultured in RPMI 1640 containing 10% FBS.

Neuro 2A cells are plated at a density of $1\times10^4$ cells per 1 ml per well in 12-well polystyrene dishes (22-mm-diameter flat-bottom wells) and are grown for 24 h in MEM with 10% FBS prior to any treatment. In the relevant experiments, nocodazole, cytochalasin B, or cycloheximide is added 3 h before addition of lactacystin. In the serum deprivation experiments, cells are switched to serum-free MEM 24 h after plating and, when relevant, incubated another 24 h before addition of lactacystin and subsequently maintained in serum-free conditions.

Example 10

Cell Cycle Analysis

MG-63 cells are plated at $7.5\times10^4$ cells per 3 ml per 25-cm$^2$ flask and grown for 24 h in RPMI containing 10% FBS. These subconfluent MG-63 cultures are synchronized in $G_0/G_1$ by changing the medium to RPMI containing 0.2% FBS and incubating for 64 h. This is followed by stimulation and incubating for 64 h. This is followed by stimulation with 2 ml of RPMI containing 10% FBS and addition of compounds. Neuro 2A cells are grown to ~$2\times10^7$ in 175-cm$^2$ flasks in MEM with 10% FBS. Mitotic cells are harvested by shaking for 5 min at 100 rpm on a rotary shaker. The detached cells are replated at $1.5\times10_5$ cells per 2 ml per 25-cm$^2$ flask and incubated for 30 min to allow for reattachment prior to addition of lactacystin. Cells are harvested for cell cycle analysis 21 h after stimulation in the case of the MG-63 cells and 20 h after replating in the case of the Neuro 2A cells and then were processed for flow cytometry. DNA histograms are obtained using a Becton Dickinson FACScan flow cytometer.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating inflammation, comprising administering to a patient in need of such treatment an effective amount of a compound of formula

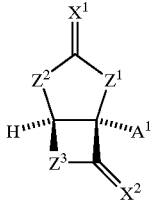

wherein $Z^1$ is O, S, $SO_2$, NH, or $NR_a$, $R_a$ being $C_{1-6}$ alkyl;

$X^1$ is O, S, $CH_2$, two singly bonded H, $CH(R_b)$ in the E or Z configuration, or $C(R_b)$ $(R_c)$ in the E or Z configuration, each of $R_b$ and $R_c$, independently, being $C_{1-6}$ alkyl, $C_{6-12}$ aryl, $C_{3-8}$ cycloalkyl, $C_{3-8}$ heteroaryl, $C_{3-8}$ heterocyclic radical, or halogen, provided that when $Z^1$ is $SO_2$, $X^1$ is two singly bonded H;

$Z^2$ is $CHR^1$ in the (R) or (S) configuration, $R^1$ being H, $C_{1-6}$ alkyl, $C_{1-6}$ haloalkyl, $C_{2-6}$ alkenyl, $C_{2-6}$ alkynyl, hydroxyl, halogen, a side chain of a naturally occurring α-amino acid, $OR_d$, $SR_d$, or $NR_dR_e$, each of $R_d$ and $R_e$, independently, being H, $C_{1-6}$ alkyl, $C_{1-6}$ haloalkyl, $C_{2-6}$ alkenyl, or $C_{2-5}$ alkynyl;

$Z^3$ is O, S, NH, or $NR_1$, wherein R is $C_{1-6}$ alkyl;

$X^2$ is O or S; and $A^1$ is H, the side chain of any naturally occurring α-amino acid, or is of the following formula,

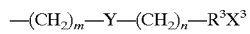

wherein Y is O, S, C=O, C=S, —(CH=CH)—, vinylidene, —C=$NOR_h$, —C=$NNR_iR_{i'}$, sulfonyl, methylene, $CHX^4$ in the (R) or (S) configuration, or deleted, $X^4$ being halogen, methyl, halomethyl, $OR_h$, $SR_h$, $NR_iR_{i'}$, —NR ($OR_h$), or —$NR_i(NR_iR_{i'})$, wherein $R_h$ is selected from H, $C_{1-6}$ alkyl, $C_{1-6}$ haloalkyl, $C_{2-6}$ alkenyl, and $C_{2-6}$ alkynyl, and each of $R_i$ and $R_{i'}$, independently is selected from H, $C_{1-6}$ alkyl, $C_{1-6}$ haloalkyl, $C_{2-6}$ alkenyl, $C_{2-6}$ alkynyl, and $C_{1-10}$ acyl; m is 0, 1, 2, or 3, and n is 0, 1, 2, or 3; and $R^3$ is straight chain or branched $C_{1-8}$ alkylidene, straight chain or branched $C_{1-8}$ alkylene, $C_{3-10}$ cycloalkylidene, $C_{3-10}$ cycloalkylene, phenylene, $C_{6-14}$ arylalkylidene, $C_{6-14}$ arylalkylene, or deleted, and $X^3$ is H, hydroxyl, thiol, carboxyl, amino, halogen, ($C_{1-6}$ alkyl) oxycarbonyl, ($C_{7-14}$ arylalkyl)oxycarbonyl, or $C_{6-14}$ aryl; or $R^3$ and $X^3$ taken together are the side chain of any naturally occurring α-amino acid.

2. The method according to claim 1, wherein $Z^1$ is NH or $NR_a$.

3. The method according to claim 1, wherein $X^2$ is O.

4. The method according to claim 2, wherein $X^2$ is O.

5. The method according to claim 2, wherein $X^2$ is O.

6. The method according to claim 2, wherein $Z^1$ is NH.

7. The method according to claim 4, wherein $Z^3$ is O.

8. The method according to claim 4, wherein $A^1$ is $-(CH_2)_m-Y-(CH_2)_n-R^3X^3$ and Y is $CHX^4$ in the (R) or (S) configuration.

9. The method according to claim 7, wherein $A^1$ is $-(CH_2)_m-Y-(CH_2)_n-R^3X^3$ and Y is $CHX^4$ in the (R) or (S) configuration.

10. The method according to claim 9, wherein Y is $CHX^4$ in the (S) configuration.

11. The method according to claim 4, wherein $Z^2$ is $CHR^1$ in the (R) configuration.

12. The method according to claim 8, wherein Y is $CHX^4$ in the (S) configuration and $X^3$ is H.

13. The method according to claim 12; wherein m and n are each 0.

14. The method according to claim 12, wherein $Z^2$ is $CHR^1$ in the (R) configuration.

15. The method of claim 1, wherein the compound is lactacystin β-lactone.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 15 amino acids

```
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 1:

Thr Thr Thr Leu Ala Phe Lys Phe Arg His Gly Gly Ile Ile Ala
1               5                   10                  15

(2) INFORMATION FOR SEQ ID NO: 2:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 2:

Thr Thr Thr Leu Ala Phe Lys Phe Arg His Gly Val Ile Val Ala
1               5                   10                  15

(2) INFORMATION FOR SEQ ID NO: 3:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 3:

Thr Thr Thr Leu Ala Phe Lys Phe Gln His Gly Val Ile Ala Ala
1               5                   10                  15

(2) INFORMATION FOR SEQ ID NO: 4:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 4:

Thr Thr Thr Leu Ala Phe Arg Phe Gln Gly Gly Ile Ile Val Ala
1               5                   10                  15

(2) INFORMATION FOR SEQ ID NO: 5:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 5:

Thr Thr Thr Val Gly Ile Thr Leu Lys Asp Ala Val Ile Met Ala
1               5                   10                  15

(2) INFORMATION FOR SEQ ID NO: 6:

(i) SEQUENCE CHARACTERISTICS:
```

(A) LENGTH: 11 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 6:

Asp Ala Tyr Ser Gly Gly Ser Val Ser Leu Tyr
1               5                   10

(2) INFORMATION FOR SEQ ID NO: 7:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 7:

Asp Ala Tyr Ser Gly Gly Ala Val Asn Leu Tyr His Val Arg
1               5                   10

(2) INFORMATION FOR SEQ ID NO: 8:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 8:

Asp Ser Tyr Ser Gly Gly Val Val Asn Met Tyr His Met Lys
1               5                   10

(2) INFORMATION FOR SEQ ID NO: 9:

(i) SEQUENCE CHARACTERISTICS:
            (A) LENGTH: 21 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 9:

Val Ile Glu Ile Asn Pro Tyr Leu Leu Gly Thr Met Ala Gly Gly Ala
1               5                   10                  15

Ala Asp Cys Ser Phe
            20

(2) INFORMATION FOR SEQ ID NO: 10:

(i) SEQUENCE CHARACTERISTICS:
            (A) LENGTH: 24 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 10:

Val Ile Glu Ile Asn Pro Tyr Leu Leu Gly Thr Leu Ala Gly Gly Ala
1               5                   10                  15

```
Ala Asp Cys Gln Phe Trp Glu Arg
            20
```

(2) INFORMATION FOR SEQ ID NO: 11:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 11:

```
Val Ile Glu Ile Asn Pro Pro Tyr Leu Leu Gly Thr Met Ser Gly Cys
1               5                   10                  15
Ala Ala Asp Cys Gln Tyr Trp Glu Arg
            20                  25
```

(2) INFORMATION FOR SEQ ID NO: 12:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 12:

```
Gly Tyr Ser Tyr Asp Leu Glu Val Glu Glu Ala Tyr Asp Leu Ala Arg
1               5                   10                  15
```

(2) INFORMATION FOR SEQ ID NO: 13:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 13:

```
Gly Tyr Ser Asp Leu Glu Val Glu Gln Ala Tyr Asp Leu Ala Arg
1               5                   10                  15
```

(2) INFORMATION FOR SEQ ID NO: 14:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 14:

```
Gly Tyr Arg Pro Asn Leu Ser Pro Glu Glu Ala Tyr Asp Leu Gly Arg
1               5                   10                  15
```

(2) INFORMATION FOR SEQ ID NO: 15:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear -continued (ii) MOLECULE TYPE: protein (xi) SEQUENCE DESCRIPTION: SEQ ID NO: 15:

```
Thr Thr Ile Ala Gly Val Val Tyr Lys Asp Gly Ile Val Leu Gly Ala
1               5                  10                 15

Asp Thr Arg
```

(2) INFORMATION FOR SEQ ID NO: 16:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 16:

```
Xaa Xaa Ile Ala Gly Val Val Tyr Lys Asp Gly Ile Val Leu Gly Ala
1               5                  10                 15

Asp Thr Arg
```

(2) INFORMATION FOR SEQ ID NO: 17:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 17:

```
Thr Thr Ile Ala Gly Val Val Tyr Lys
1               5
```